(12) United States Patent
Goodson, Jr. et al.

(10) Patent No.: US 7,511,065 B2
(45) Date of Patent: Mar. 31, 2009

(54) MIXED LINEAGE KINASE MODULATORS

(75) Inventors: Theodore Goodson, Jr., Indianapolis, IN (US); Mary Margaret Mader, Fishers, IN (US); John Eldon Toth, Indianapolis, IN (US); Arindam Chatterjee, Fishers, IN (US); Jason Scott Sawyer, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 671 days.

(21) Appl. No.: 10/535,061

(22) PCT Filed: Nov. 12, 2003

(86) PCT No.: PCT/US03/35036

§ 371 (c)(1),
(2), (4) Date: May 12, 2005

(87) PCT Pub. No.: WO2004/048383

PCT Pub. Date: Jun. 10, 2004

(65) Prior Publication Data

US 2008/0113977 A1    May 15, 2008

Related U.S. Application Data

(60) Provisional application No. 60/428,322, filed on Nov. 21, 2002.

(51) Int. Cl.
*C07D 487/04* (2006.01)

(52) U.S. Cl. .................. 514/338; 514/314; 514/406; 546/167

(58) Field of Classification Search .............. 514/314, 514/338, 406; 546/167
See application file for complete search history.

(56) References Cited

U.S. PATENT DOCUMENTS

| 6,262,074 | B1 | 7/2001 | Otten et al. |
| 6,262,269 | B1 | 7/2001 | Hayes et al. |
| 6,391,874 | B1 | 5/2002 | Cockerill et al. |
| 7,087,626 | B2 * | 8/2006 | Beight et al. ............. 514/338 |

FOREIGN PATENT DOCUMENTS

| EP | 0 531 901 | 3/1993 | |
| WO | WO 98/34115 | 8/1998 | |
| WO | WO 01/85686 | 11/2001 | |
| WO | WO 02/26713 | 4/2002 | |
| WO | WO 02/094833 | 11/2002 | |
| WO | WO02/094833 A1 * | 11/2002 | ............. 514/183 |

* cited by examiner

*Primary Examiner*—Kamal A Saeed
*Assistant Examiner*—Valerie Rodriguez-Garcia
(74) *Attorney, Agent, or Firm*—Danica Hostettler; Alexander Wilson

(57) ABSTRACT

The present invention provides a compound of the formula: (Formula I); or a pharmaceutically acceptable salt thereof, pharmaceutical compositions comprising an effective amount of a compound of Formula I in combination with a suitable carrier, diluent, or excipient, and methods for treating physiological disorders, particularly congestive heart disease, comprising administering to a patient in thereof an effective amount of a compound of Formula I.

8 Claims, No Drawings

MIXED LINEAGE KINASE MODULATORS

This application is a national stage entry of PCT/US03/35036 filed on Nov. 12, 2003 which claims priority benefit of U.S. Provisional Application No. 60/428,322 filed on Nov. 21, 2002.

BACKGROUND OF THE INVENTION

Mixed lineage kinases (MLKs) are a family of serine/threonine protein kinases that function in a cascade of phosphorylation reactions to control the activity of specific mitogen activated protein kinases (MAPKs). Gallo and Johnson, *Nature Reviews;* 3: 663-664 (2002). MLKs act as MAPK-kinase kinases (MAPKKKs) to activate, for example, the stress activated protein kinase/c-Jun N-terminal kinase (SAPK/JNK) and p38 kinase pathways, through phosphorylation of MAPK kinases (MKKs). Bloem et al., *J. Mol. Cell. Cardiol.;* 33: 1739-1750, (2001). SAPK/JNK and p38 kinase are specific MAPKs that, like other eukaryotic MAPKs, are activated in response to a multitude of stimuli including exposure to inflammatory cytokines, hormones, and growth factors as well as cellular stresses such as heat shock, inhibition of protein glycosylation, and exposure to ultraviolet irradiation. Fanger et al., *Curr. Opin. Genet. Dev.;* 7(1): 67-74 (1997).

Three subfamilies of MLKs have been previously identified and grouped on the basis of domain arrangements and sequence homology within their catalytic domains. The MLKs (MLK1-MLK4) contain an amino-terminal SRC homology domain (SH3), followed sequentially by a catalytic kinase domain, a leucine zipper region, and a Cdc42/Rac-interactive binding domain (CRIB Motif). MLK1-MLK4 share approximately 75% homology within their catalytic domains and approximately 65% homology from the SH3 domain to the CRIB motif. However, the carboxy terminus of each of these kinases diverge, indicating these regions may serve different regulatory functions. *Nature Reviews;* 3: 663-664 (2002). The duel leucine zipper bearing kinases (DLKs) represent the second family of MLKs and are characterized by a kinase domain followed by two leucine zipper motifs, separated by a 31 amino acid spacer. The catalytic domains of the two DLKs (DLK and leucine zipper kinase (LZK)) share approximately 87% sequence homology but again diverge in their carboxy terminus. The final subfamily of MLK is represented by zipper sterile α αmotif kinase (ZAK). ZAK shares homology with the other MLKs through the leucine zipper domain, but again diverges from the others at the carboxy terminus. *Nature Reviews;* 3: 663-664 (2002). While all of the MLKs have been shown to activate the c-Jun N-terminal kinase pathway, some have also been shown to activate the p38 kinase pathway as well. In addition, other MAPKKKs have been identified which activate the JNK and p38 kinase pathways, including MEK kinase; apoptosis inducing kinase 1 (ASK1); and transforming growth factor beta (TGFβ)-activated kinase (TAK1). *Nature Reviews;* 3: 663-664 (2002).

Congestive heart failure (CHF) is a complex disorder with several etiologies including hypertension, myocardial injury, and hemodynamic overload. One of the adaptive responses of the heart to these stresses is hypertrophy of the cardiac myocyte, characterized by altered gene transcriptional regulation, increased protein synthesis, and increased organization of the myofibril. This hypertrophy, in turn, may lead to remodeling of the heart and subsequent failure. *J. Mol. Cell. Cardiol;* 33: 1739-1750, (2001). Evidence suggests that activation of signal transduction pathways, including MAPK and stress activated protein kinase (SAPK/JNK) pathways contribute to hypertrophic changes in the heart. (See generally: Sugden et al., *J. Mol. Med.;* 76: 725-746, (1998); Force et al., *Gene Expression;* 7: 337-348, (1999); Ramirez et al., *J. Biol. Chem.;* 272: 14057-14061, (1997); Bogoyevitch; *Cardiovasc. Res.,* 45: 826- 842, (2000); Hines et al.; *J. Mol. Cell. Cardiol.,* 30: 485-494, (1998) and Clerk et al.; *Am. J. Cardiol.,* 83: 64H-69H, (1999)).

Recently, a novel MAPKKK, designated as MLK-7, was identified from a database mining effort of a cDNA library from human failed heart tissue. The cDNA encodes for a 55 kDa. protein with serine/threonine kinase activity when expressed and purified from insect cells. *J. Mol. Cell. Cardiol;* 33: 1739-1750, (2001) In addition, MLK-7 activates the SAPK/JNK1 pathway in rat neonatal cardiac myocytes and modulates fetal expression of marker genes for cardiac hypertrophy. Specifically, MLK-7 increased expression of atrial natruiretic factor (ANF) and decreased expression of α myosin heavy chain (αMHC) mRNAs in rat neonatal cardiac myocytes. Furthermore, MLK-7 also increased protein synthesis in cardiac myocytes as evidenced by increased [$^{14}$C] phenylalanine incorporation in MLK-7-infected cells. *J. Mol. Cell. Cardiol;* 33: 1739-1750, (2001). Taken together this data suggests that MLK-7 is implicated in the hypertrophy of cardiac myocytes that occurs in response to the various etiologies of congestive heart failure. Thus antagonists of MLK-7 activity may have utility in the treatment patients suffering from CHF.

Surprisingly, and in accordance with this invention, Applicants have discovered a series of dihydropyrrolopyrazole compounds of Formula I which are believed to be novel, as more fully described below, which are potent antagonists of the recently identified MLK-7. Such antagonists could be useful for the treatment of CHF and could therefore address a long felt need for a safe and effective treatment for CHF. The treatment of cardiovascular disorders is hereby furthered.

SUMMARY OF THE INVENTION

The present invention is directed to the discovery that dihydropyrrolopyrazole-derivative compounds of the present invention, as defined below, are antagonists of the mitogen activated protein kinase kinase kinase, MLK-7. Accordingly, the present invention provides a compound of the formula:

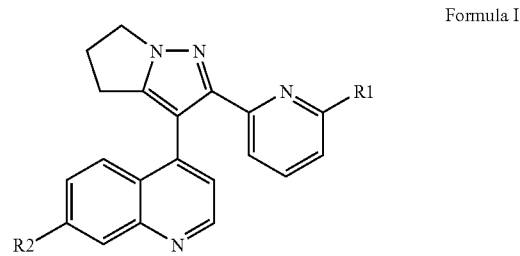

Formula I wherein,
R1 represents hydrogen, halo, or (C1-C4)alkyl; and
R2 represents:
(a) aryl;
(b) aryl optionally substituted one to three times with a substituent independently selected from the group consisting of:
(i) halo,
(ii) amino,
(iii) nitro, (iv) hydroxy,
(v) cyano,
(vi) $(C_1-C_4)$alkyl,
(vii) $(C_1-C_4)$alkoxy,
(viii) hydroxy$(C_1-C_4)$alkyl,
(ix) amino$(C_1-C_4)$alkyl
(x) hydroxy$(C_1-C_4)$alkoxy,
(xi) halo$(C_1-C_4)$alkoxy,
(xii) $(C_1-C_4)$alkoxy$(C_1-C_4)$alkoxy,
(xiii) trifluoromethyl,
(xiv) difluoromethyl,
(xv) trifluoromethoxy,
(xvi) difluoromethoxy,
(xvii) $(C_3-C_7)$cylcoalkyl,
(xviii) $COR^3$,
(xix) $(C_1-C_4)$alkyl-COR4,
(xx) amino$(C_1-C_4)$alkyl-COR4,
(xxi) hydroxy$(C_1-C_4)$alkyl-COR4
(xxii) $(C_1-C_4)$alkoxy-COR5,
(xxiii) —C(NH$_2$)=N—OH
(xxiv) NHSO$_2$R$^6$,
(xxv) SO$_2$R$^7$,
(xxvi) NHCOR$^8$,
(xxvii) SOR$^9$,
(xxviii) SR$^{10}$,
(xxix) CONHR$^{11}$,
(xxx) O—(CH$_2$)q-NR$^{12}$R$^{13}$, wherein q represents 1-4,
(xxxi) tetrazole,
(xxxii) methyltetrazole, and
(xxxiii) CONCH—NR$^{15}$R$^{16}$
(c) heterocycle;
(d) heterocycle optionally substituted one to three times with a substituent independently selected from the group consisting of:
(i) halo,
(ii) amino,
(iii) $(C_1-C_4)$alkyl,
(iv) $(C_1-C_4)$alkoxy,
(v) halophenyl$(C_1-C_4)$alkyl,
(vi) $(C_1-C_4)$alkyl-$(C_1-C_4)$alkoxycarbonyl,
(vii) CHO,
(viii) COR$^3$, or
(ix) SO$_2$R$^7$,
(e) benzofused heterocycle;
(f) benzofused heterocycle optionally substituted one or two times with a substituent independently selected from the group consisting of:
(i) halo,
(ii) amino,
(iii) $(C_1-C_4)$alkyl,
(iv) $(C_1-C_4)$alkoxy, and
(v) $(C_1-C_4)$alkylcarbonyl, or
(g) $(C_3-C_7)$cylcoalkyl;
R$^3$ represents independently at each occurrence amino, hydroxy, $(C_1-C_4)$alkyl, $(C_1-C_4)$alkoxy, NH—$(C_1-C_4)$alkylamine, N,N—$(C_1-C_4)$dialkylamine, or a heterocycle selected from the group consisting of:

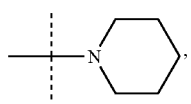
(a)

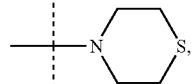
(b)

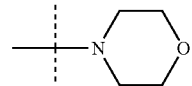
(c)

(d)
or

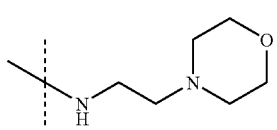
(e)

R$^4$ and R$^5$ represent independently at each occurrence amino, hydroxy, $(C_1-C_4)$alkyl, or $(C_1-C_4)$alkoxy;

R$^6$ and R$^7$ represent independently at each occurrence amino or (C1-C4)alkyl;

R$^8$ represents independently at each occurrence amino, $(C_1-C_4)$alkyl, or $(C_1-C_4)$alkoxy;

R$^9$ and R$^{10}$ represent independently at each occurrence (C1-C4)alkyl;

R$^{11}$ represents independently at each occurrence (C1-C4) alkyl or a substituent selected from the group consisting of:
(a) —(CH$_2$)$_n$—X—Y
(b) —CH(COR$^{14}$)—(CH$_2$)$_m$—X'—Y'

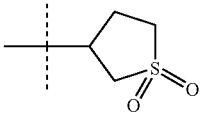
(c)

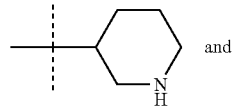
(d)
and

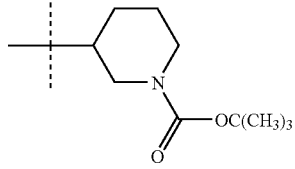
(e)

wherein,
n and m each independently represent 0-4;
X and X' represent independently at each occurrence —CO—, —CH$_2$—, —NH—, —S—, or —SO$_2$—; and
Y and Y' represent independently at each occurrence amino, hydroxy, $(C_1-C_4)$alkyl, $(C_1-C_4)$alkoxy, $(C_1-C_4)$alkoxycarbonyl, NH—$(C_1-C_4)$alkylamine, or N,N—$(C_1-C_4)$dialkylamine,
provided that where X or X' represents S, then Y or Y" is not amino or hydroxy;
R$^{12}$ and R$^{13}$ represent independently at each occurrence hydrogen or $(C_1-C_4)$alkyl, or R$^{12}$ and R$^{13}$ together with the nitrogen atom to which they are attached form a piperidino, pyrrolidino, morpholino or a methylpiperazino group;

$R^{14}$ represents independently at each occurrence hydroxy, amino, or $(C_1-C_4)$alkoxy; and $R^{15}$ and $R^{16}$ each represent independently at each occurrence hydrogen or $(C_1-C_4)$alkyl, or a pharmaceutically acceptable salt thereof.

In another embodiment, the present invention provides a method of treating or preventing congestive heart failure, comprising administering to a patient in need thereof an effective amount of a compound of Formula I, or a pharmaceutically acceptable salt thereof.

In addition, the present invention provides pharmaceutical compositions of compounds of Formula I, including the pharmaceutically acceptable salts and hydrates thereof, comprising a compound of Formula I in combination with a pharmaceutically acceptable carrier, diluent or excipient. This invention also encompasses novel intermediates, and processes for the synthesis of the compounds of Formula I.

In another embodiment, the present invention provides the use of a compound of Formula I for the manufacture of a medicament for treating or preventing congestive heart failure.

DETAILED DESCRIPTION OF THE INVENTION

The present invention provides compounds with affinity for the mitogen activated protein kinase kinase kinase designated as MLK-7, which could be used to antagonize or partially antagonize kinase activity and thereby influence physiological functions related to kinase levels and/or kinase activity. In this regard, such ligands are believed to be useful in treating or preventing physiological disorders susceptible to MLK7 modulation, particularly MLK-7 antagonism. Thus, methods for the treatment or prevention of physiological disorders susceptible to MAPKKK modulation, particularly MLK-7 antagonism, constitute an important embodiment of the present invention. As a particular aspect, the present invention provides compounds useful as MLK-7 modulators. As a more particular aspect, the present invention provides compounds useful as MLK-7 antagonists. Furthermore, compounds of Formula I are believed to be novel and, thus, to constitute yet another important embodiment of the present invention. In addition, compounds of the present invention may also exert antagonist activity at other MAPKKKs as well as inhibiting the action of other serine/threonine kinases such as the TGFβ receptors, Type I and Type II.

As will be understood by the skilled artisan, some of the compounds useful for the methods of the present invention may be available for prodrug formulation. Where used herein, the term "prodrug" refers to a compound of Formula I which has been structurally modified such that in vivo the prodrug is converted, for example, by hydrolytic, oxidative, reductive, or enzymatic cleavage, into the parent molecule ("drug") as given by Formula I. Such prodrugs may be, for example, metabolically labile ester derivatives of the parent compound where said parent molecule bears a carboxylic acid group. Conventional procedures for the selection and preparation of suitable prodrugs are well known to one of ordinary skill in the art.

It is also understood that many of the MAPKKK modulators of the present invention may exist as pharmaceutically acceptable salts and, as such, pharmaceutically acceptable salts are therefore included within the scope of the present invention. The term "pharmaceutically acceptable salt" where used herein, refers to salts of the compounds of Formula I, which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. It is further understood by the skilled reader that salt forms of pharmaceutical compounds are commonly used because they are often more readily crystallized, or more readily purified, than are the free bases. In all cases, the use of the pharmaceutical compounds of the present invention as salts is contemplated in the description herein. Hence, it is understood that where compounds of Formula I are capable of forming salts, the pharmaceutically acceptable salts are encompassed in the names provided herein.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, hydroiodide, dihydroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napththalene-2-sulfonate, mandelate and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

Where used herein, the term "stereoisomer" refers to a compound made up of the same atoms bonded by the same bonds but having different three-dimensional structures which are not interchangeable. The three-dimensional structures are called configurations. Where used herein, the term "enantiomer" refers to two stereoisomers whose molecules are nonsuperimposable mirror images of one another. The term "chiral center" refers to a carbon atom to which four different groups are attached. Where used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The compounds of the present invention may have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. All such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981.

The terms "R" and "S" where used herein are as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

Where used herein the term "Pg" refers to a suitable oxygen or nitrogen protecting group. Suitable oxygen or nitrogen protecting groups, where used herein, refers to those groups intended to protect or block the oxygen or nitrogen group against undesirable reactions during synthetic procedures. Whether the term "Pg", where used herein, represents an oxygen protecting group or a nitrogen protecting group will be readily apparent to the ordinarily skilled artisan. The suitability of the oxygen or nitrogen protecting group used will depend upon the conditions that will be employed in subsequent reaction steps wherein protection is required, and is well within the knowledge of one of ordinary skill in the art.

Commonly used nitrogen protecting groups are disclosed in Greene, "Protective Groups In Organic Synthesis," (John Wiley & Sons, New York (1981)). Suitable nitrogen protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha.,.alpha.-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Commonly used oxygen protecting groups are also disclosed in Greene (supra). Suitable oxygen protecting groups comprise alkyl groups such as methyl, ethyl, and the like; silyl groups such as t-butyldimethylsilyl, t-butyldiphenylsilyl, triisopropylsilyl, and the like, with t-butyldimethylsilyl being preferred. Other commonly used oxygen protecting groups include benzyl, 4-nitrophenyl methyl, benzoyl, and the like.

Where used herein the term "$(C_1-C_4)$alkyl" refers to a straight or branched, monovalent, saturated aliphatic chain of 1 to 4 carbon atoms and includes, but is not limited to, methyl, ethyl, n-propyl, isopropyl, n-butyl, isobutyl and the like.

Where used herein the term "$(C_1-C_6)$alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It is understood that the term "$(C_1-C_4)$alkyl" is included within the definition of "$(C_1-C_6)$alkyl".

Where used herein the term "$(C_1-C_{10})$alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. It is understood that the terms "$(C_1-C_4)$alkyl" and "$(C_1-C_6)$alkyl" are included within the definition of "$(C_1-C_{10})$alkyl".

Where used herein, the terms "Me", "Et", "Pr" "iPr", "Bu" and "t-Bu" refer to methyl, ethyl, propyl, isopropyl, butyl and tert-butyl respectively.

Where used herein, the term "$(C_1-C_4)$alkoxy" refers to an oxygen atom bearing a straight or branched, monovalent, saturated aliphatic chain of 1 to 4 carbon atoms and includes, but is not limited to, methoxy, ethoxy, n-propoxy, isopropoxy, n-butoxy, and the like. Where used herein the term "$(C_1-C_6)$alkoxy" refers to an oxygen atom bearing a straight or branched, monovalent, saturated aliphatic chain of 1 to 6 carbon atoms and includes, but is not limited to, methoxy, ethoxy, n-propoxy, isopropoxy, n-butoxy, n-pentoxy, n-hexoxy, and the like. It is understood that the term "$(C_1-C_4)$alkoxy" is included within the definition of "$(C_1-C_6)$alkoxy".

Where used herein, the term "amino$(C_1-C_4)$alkyl" refers to a straight or branched, monovalent, saturated aliphatic chain of 1 to 4 carbon atoms bearing an amino group attached to one of the carbon atoms.

Where used herein, the term "hydroxy$(C_1-C_4)$alkyl" refers to a straight or branched, monovalent, saturated aliphatic chain of 1 to 4 carbon atoms bearing a hydroxyl group attached to one of the carbon atoms. Where used herein, the term "hydroxy$(C_1-C_6)$alkyl" refers to a straight or branched, monovalent, saturated aliphatic chain of 1 to 6 carbon atoms bearing a hydroxyl group attached to one of the carbon atoms. It is understood that the term "hydroxy$(C_1-C_4)$alkyl" is included within the definition of "hydroxy$(C_1-C_6)$alkyl".

Where used herein, the term "hydroxy($C_1$-$C_4$)alkoxy" refers to an oxygen atom bearing a straight or branched, monovalent, saturated aliphatic chain of 1 to 4 carbon atoms with a hydroxyl group attached to one of the carbon atoms. Where used herein, the term "hydroxy($C_1$-$C_6$)alkoxy" refers to an oxygen atom bearing a straight or branched, monovalent, saturated aliphatic chain of 1 to 6 carbon atoms with a hydroxyl group attached to one of the carbon atoms. It is understood that the term "hydroxy($C_1$-$C_4$)alkoxy" is included within the definition of "hydroxy($C_1$-$C_6$)alkoxy".

Where used herein, the term "($C_1$-$C_4$)alkyl-($C_1$-$C_4$)alkoxy" refers to a straight or branched, monovalent, saturated aliphatic chain of 1 to 4 carbon atoms which has a ($C_1$-$C_4$)alkoxy group attached to the aliphatic chain. Where used herein, the term "($C_1$-$C_4$)alkoxy-($C_1$-$C_4$)alkoxy" refers to an oxygen atom bearing straight or branched, monovalent, saturated aliphatic chain of 1 to 4 carbon atoms which has a ($C_1$-$C_4$)alkoxy group attached to the aliphatic chain.

Where used herein, the term "($C_1$-$C_4$)alkyl-$COR^4$" refers to a straight or branched, monovalent, saturated aliphatic chain of 1 to 4 carbon atoms which has a $COR^4$ group attached to the aliphatic chain ($R^4$ being as defined elsewhere herein). Where used herein, the term "($C_1$-$C_4$)alkoxy-$COR^5$" refers to an oxygen atom bearing a straight or branched, monovalent, saturated aliphatic chain of 1 to 4 carbon atoms which has a $COR^5$ group attached to the aliphatic chain ($R^5$ being as defined elsewhere herein).

Where used herein, the term "amino($C_1$-$C_4$)alkyl-$COR^4$" refers to an amino($C_1$-$C_4$)alkyl group which has a $COR^4$ group attached to the aliphatic chain ($R^4$ being as defined elsewhere herein). The term "hydroxy($C_1$-$C_4$)alkyl-$COR^4$" refers to a hydroxy($C_1$-$C_4$)alkyl group which has a $COR^4$ group attached to the aliphatic chain ($R^4$ being as defined elsewhere herein).

Where used herein, the terms "halo", "halide" or "hal" of "Hal" refer to a chlorine, bromine, iodine or fluorine atom, unless otherwise specified herein.

Where used herein, the term "halo($C_1$-$C_4$)alkyl" refers to a straight or branched, monovalent, saturated aliphatic chain of 1 to 4 carbon atoms bearing one or more halo groups attached to one or more of the carbon atoms. Where used herein, the term "halo($C_1$-$C_6$)alkyl" refers to a straight or branched, monovalent, saturated aliphatic chain of 1 to 6 carbon atoms bearing one or more halo groups attached to one or more of the carbon atoms. It is understood that the term "halo($C_1$-$C_4$)alkyl" is included within the definition of "halo($C_1$-$C_6$)alkyl". Where used herein, the term "halo($C_1$-$C_4$)alkoxy" refers to an oxygen atom bearing a straight or branched, monovalent, saturated aliphatic chain of 1 to 4 carbon atoms bearing one or more halo groups attached to one or more of the carbon atoms. Where used herein, the term "halo($C_1$-$C_6$)alkoxy" refers to an oxygen atom bearing a straight or branched, monovalent, saturated aliphatic chain of 1 to 6 carbon atoms bearing one or more halo groups attached to one or more of the carbon atoms. It is understood that the term "halo($C_1$-$C_4$)alkoxy" is included within the definition of "halo($C_1$-$C_6$)alkoxy".

Where used herein, the term "halophenyl($C_1$-$C_4$)alkyl" refers to a straight or branched, monovalent, saturated aliphatic chain of 1 to 4 carbon atoms bearing phenyl group which is further substituted with a halo moiety. Examples of "halophenyl($C_1$-$C_4$)alkyl" include (4-chlorophenyl)methyl, (3-chlorophenyl)methyl, (4-chlorophenyl)ethyl, (3-chlorophenyl)ethyl, and the like Where used herein the term "($C_2$-$C_6$)alkenyl" refers to a straight or branched, monovalent, unsaturated aliphatic chain having from two to six carbon atoms and having a double bond. Typical ($C_2$-$C_6$)alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

Where used herein the term "($C_2$-$C_6$)alkynyl" refers to a straight or branched, monovalent, unsaturated aliphatic chain having from two to six carbon atoms and having a triple bond.

Where used herein, the term "aryl" refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

Where used herein, the term "aryl ($C_1$-$C_6$)alkyl" refers to a straight or branched, monovalent, saturated aliphatic chain of 1 to 6 carbon atoms which has an aryl group attached to the aliphatic chain. "aryl ($C_1$-$C_4$)alkyl" refers to a straight or branched, monovalent, saturated aliphatic chain of 1 to 4 carbon atoms which has an aryl group attached to the aliphatic chain. It is understood that the term "aryl ($C_1$-$C_4$)alkyl" is included within the definition of "aryl ($C_1$-$C_6$)alkyl". Examples of "aryl ($C_1$-$C_6$)alkyl" include:

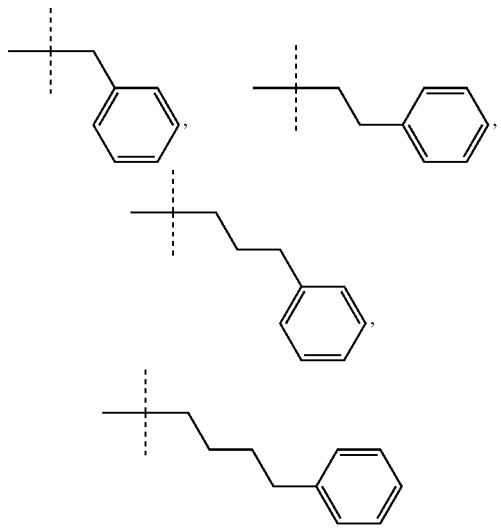

and the like.

Where used herein, the term "aryl($C_1$-$C_6$)alkoxy" refers to an oxygen atom bearing a straight or branched, monovalent, saturated aliphatic chain of 1 to 6 carbon atoms wherein said aliphatic chain, in turn, bears an aryl group.

Where used herein the term "($C_3$-$C_{10}$)cycloalkyl" refers to a saturated hydrocarbon ring structure composed of one or more fused or unfused rings containing from three to ten carbon atoms. Typical ($C_3$-$C_{10}$)cycloalkyl groups include cyclopropyl, cyclobutyl, cyclopentyl, cyclohexyl, cycloheptyl, cyclooctyl, adamantanyl, and the like. "($C_3$-$C_7$)cycloalkyl" refers to a saturated hydrocarbon ring structure composed of one or more fused or unfused rings containing from three to seven carbon atoms. It is understood that the definition of "($C_3$-$C_7$)cycloalkyl" is included within the definition of "($C_3$-$C_{10}$)cycloalkyl".

Where used herein, the term "($C_1$-$C_4$)alkyl-($C_3$-$C_7$)cycloalkyl" refers to a straight or branched, monovalent, saturated aliphatic chain of 1 to 4 carbon atoms which has a ($C_3$-$C_7$)cycloalkyl attached to the aliphatic chain. Included within the term "($C_1$-$C_4$)alkyl-($C_3$-$C_7$)cycloalkyl" are the following:

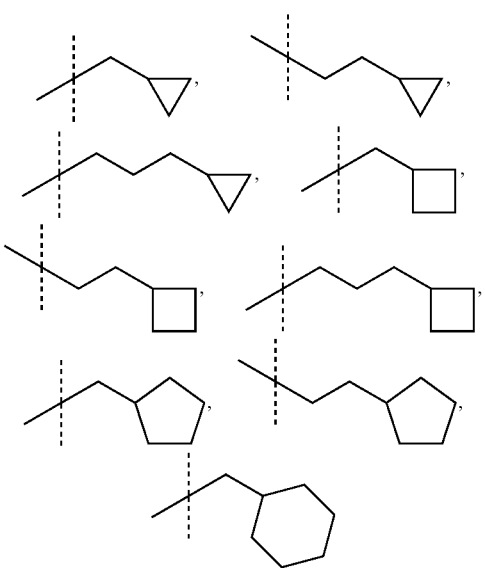

and the like.

Where used herein the term "(C$_3$-C$_7$)cycloalkoxy" refers to an oxygen atom bearing a saturated hydrocarbon ring structure composed of one or more fused or unfused rings containing from three to seven carbon atoms.

Where used herein, the term "(C$_1$-C$_4$) alkoxycarbonyl" refers to a carbonyl group having a (C$_1$-C$_4$)alkyl group attached to the carbonyl carbon through an oxygen atom. Examples of this group include t-butoxycarbonyl, methoxycarbonyl, ethoxycarbonyl and the like.

Where used herein, the term "(C$_1$-C$_4$)alkyl-(C$_1$-C$_4$) alkoxycarbonyl" refers to a straight or branched, monovalent, saturated aliphatic chain of 1 to 4 carbon atoms bearing a carbonyl group having a (C$_1$-C$_4$)alkyl group attached to the carbonyl carbon through an oxygen atom. Examples include methoxycarbonyl methyl, ethoxycarbonyl methyl, 2-methoxycarbonyl ethyl, and the like.

Where used herein, the term "(C$_1$-C$_4$)alkylcarbonyl" refers to a carbonyl group bearing a straight or branched, monovalent, saturated aliphatic chain of 1 to 4 carbon atoms attached to the carbonyl carbon.

Where used herein the term "heterocycle" refers to a saturated or unsaturated, five- or six-membered ring, which contains one to four heteroatoms selected from the group consisting of oxygen, sulfur, and nitrogen. It is understood that the remaining atoms are carbon and that the heterocycle may be attached at any point which provides for a stable structure. Examples of heterocycle groups include thiopheneyl, furanyl, tetrahydrofuryl, imidazolyl, pyrazolyl, pyrrolyl, thiazolyl, thiazolidinyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridazinyl, triazinyl, imidazolyl, dihydropyrimidyl, tetrahydropyrimdyl, pyrrolidinyl, piperidinyl, piperazinyl, pyrazolidinyl, pyrimidinyl, imidazolidimyl, morpholinyl, pyranyl, thiomorpholinyl, dioxo-thiomorpholinyl, and the like. Where used herein, the term "benzofused heterocyclic ring" refers to a saturated or unsaturated, five- or six-membered ring, which contains one to four heteroatoms selected from the group consisting of oxygen, sulfur, and nitrogen, and which is fused to a phenyl group. It is understood that the remaining atoms are carbon and that the benzofused heterocycle may be attached at any point on either the heterocyclic or phenyl ring which provides for a stable structure. Representative "benzofused heterocyclic rings" include benzoxazole, benzoimidazole, benzofuran, benzothiophene, benzo[1,3]-dioxolyl, benzothiazole, 2,2-dioxy-2,3-dihydro-1H-2λ$^6$-benzo[c]thiophene, azaindole, and indole.

Where used herein the term "NH(C$_3$-C$_7$)cycloalkyl" refers to an amino group substituted with a saturated hydrocarbon ring structure composed of one or more fused or unfused rings containing from three to seven carbon atoms.

Where used herein the term "N,N—(C$_1$-C$_4$)dialkylamine" refers to a nitrogen atom substituted with two independently selected straight or branched, monovalent, saturated aliphatic chains of 1 to 4 carbon atoms. Included within the term "N,N—(C$_1$-C$_6$)dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, and the like. "NH—(C$_1$-C$_4$) alkylamine" refers to a nitrogen atom substituted with a straight or branched, monovalent, saturated aliphatic chains of 1 to 4 carbon atoms. Included within the term "NH—(C$_1$-C$_4$) alkylamine" are —NH(CH$_3$), —NH(CH$_2$CH$_3$), —NH(CH$_2$CH$_2$CH$_3$), —NH(CH$_2$CH$_2$CH$_2$CH$_3$), and the like.

The designation " ◄■ " refers to a bond that protrudes forward out of the plane of the page.

The designation " ⦀ " refers to a bond that protrudes backward out of the plane of the page.

Where used herein, the term "mitogen activated protein kinase kinase kinase modulator" or "MAPKKK modulator" refers to a ligand which binds to any one of the mitogen activated protein kinase kinase kinases and either agonizes, antagonizes, partially agonizes, or partially antagonizes the kinase's activity. Where used herein, the term "mitogen activated protein kinase kinase kinase antagonist" or "MAPKKK antagonist" refers to a ligand which binds to any one of the mitogen activated protein kinase kinase kinases and either antagonizes, or partially antagonizes the kinase's activity. It is understood that the term "mixed lineage kinase-7 antagonist" or "MLK-7 antagonist" refers to an antagonist of the specific MAPKKK designated as "mixed lineage kinase-7" or "MLK-7" and is included within the meanings of "mitogen activated protein kinase kinase kinase modulator" or "mitogen activated protein kinase kinase kinase antagonist".

Where used herein the term "mixed lineage kinase-7" or "MLK-7" refers to the mitogen activated protein kinase kinase kinase, subtype 7, as described by Bloem et al, *J. Mol. Cell. Cardiol.*; 33: 1739-1750, (2001), of the larger class of mitogen activated protein kinase kinase kinases, which functions as a serine/threonine kinase to activate cellular signaling pathways.

Where used herein the term "congestive heart failure" (CHF) or "congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, myocardial injury, hemodynamic overload, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood. It is understood that the terms "diastolic congestive heart failure" and "systolic congestive heart failure" are included within the term "congestive heart failure" or "CHF".

As appreciated by one of skill in the art, physiological disorders may present as a "chronic" condition, or an "acute" episode. The term "chronic", where used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of physiological disorders contemplates both acute events and chronic conditions. In an acute event, compound is administered at the onset of symptoms and discontinued when the symptoms disappear. As described above, a chronic condition is treated throughout the course of the disease.

Where used herein the term "patient" refers to a mammal, such a mouse, gerbil, guinea pig, rat, dog or human. It is understood, however, that the preferred patient is a human. Where used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

Where used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as a MAPKKK modulator. Oral administration, however, is not the only route, nor even the only preferred route. Other preferred routes of administration include transdermal, percutaneous, pulmonary, intravenous, intramuscular, intranasal, buccal, sublingual, or intrarectal routes. Where the MAPKKK modulator is administered as a combination of compounds, one of the compounds may be administered by one route, such as oral, and the other may be administered by the transdermal, percutaneous, pulmonary, intravenous, intramuscular, intranasal, buccal, sublingual, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of Formula I are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, including the pharmaceutically acceptable salts and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

The following discussion provides typical procedures for preparing pharmaceutical compositions incorporating the compounds of the present invention. However, the following is in no way intended to limit the scope of the pharmaceutical compositions provided by the present invention.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

It is understood by one of ordinary skill in the art that the formulation procedures as described above can be readily applied to a method of treating physiological disorders susceptible to MAPKKK modulation or MLK-7 modulation, and particularly congestive heart failure.

Particular Aspects of the Compounds of the Invention

As discussed previously, compounds of Formula I are believed to be novel and, thus, to represent an important embodiment of the present invention. The following list sets out several groupings of particular substituents and particular variables of the compounds of Formula I. It will be understood that compounds of Formula I, or methods employing compounds of Formula I, having such particular substituents and variables represent particular aspects of the present invention. It will be further understood that each of these groupings may be combined with other provided groupings, to create still additional particular aspects of the present invention.

Thus, a particular aspect of the compounds of Formula I is one wherein:
(A) R1 represents hydrogen or methyl; or
(B) R1 represents hydrogen.
(C) R2 represents:
  (a) phenyl;
  (b) phenyl optionally substituted one to three times with a substituent independently selected from the group consisting of:
    (i) halo,
    (ii) amino,
    (iii) nitro,
    (iv) hydroxy,
    (v) cyano,
    (vi) $(C_1-C_4)$alkyl,
    (vii) $(C_1-C_4)$alkoxy,
    (viii) amino$(C_1-C_4)$alkyl
    (ix) hydroxy$(C_1-C_4)$alkoxy,
    (x) halo$(C_1-C_4)$alkoxy,
    (xi) $(C_1-C_4)$alkoxy$(C_1-C_4)$alkoxy,
    (xii) trifluoromethyl,
    (xiii) $(C_3-C_7)$cylcoalkyl,
    (xiv) $COR^3$,
    (xv) $(C_1-C_4)$alkyl-COR4,
    (xvi) $(C_1-C_4)$alkoxy-COR5,
    (xvii) $NHSO_2R^6$,
    (xviii) $SO_2R^7$,
    (xix) $NHCOR^8$,
    (xx) $SOR^9$,
    (xxi) $SR^{10}$,
    (xxii) $CONHR^{11}$, and
    (xxiii) $O-(CH_2)q-NR^{12}R^{13}$, wherein q represents 1-4;
  (c) thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl;
  (d) thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl optionally substituted one to three times with a substituent independently selected from the group consisting of:
    (i) halo,
    (ii) amino,
    (iii) $(C_1-C_4)$alkyl,
    (iv) $(C_1-C_4)$alkoxy,
    (v) $COR^3$, or
    (vi) $SO_2R^7$,
  (e) benzimidazole, benzofuran, benzothiophene, benzo[1,3]-dioxolyl, benzothiazole, 2,2-dioxy-2,3-dihydro-1H-2$\lambda^6$-benzo[c]thiophene, or indole;
  (f) benzimidazole, benzofuran, benzothiophene, benzo[1,3]-dioxolyl, benzothiazole, 2,2-dioxy-2,3-dihydro-1H-2$\lambda^6$-benzo[c]thiophene, and indole optionally substituted one or two times with a substituent independently selected from the group consisting of:
    (i) halo,
    (ii) amino,
    (iii) $(C_1-C_4)$alkyl, or
    (iv) $(C_1-C_4)$alkoxy,
  or (g) cyclohexyl;

(D) R2 represents:
 (a) phenyl;
 (b) phenyl optionally substituted one to three times with a substituent independently selected from the group consisting of:
  (i) halo,
  (ii) amino,
  (iii) nitro,
  (iv) hydroxy,
  (v) cyano,
  (vi) ($C_1$-$C_4$)alkyl,
  (vii) ($C_1$-$C_4$)alkoxy,
  (viii) amino($C_1$-$C_4$)alkyl
  (ix) hydroxy($C_1$-$C_4$)alkoxy,
  (x) halo($C_1$-$C_4$)alkoxy,
  (xi) ($C_1$-$C_4$)alkoxy($C_1$-$C_4$)alkoxy,
  (xii) trifluoromethyl,
  (xiii) ($C_3$-$C_7$)cylcoalkyl,
  (xiv) $COR^3$,
  (xv) ($C_1$-$C_4$)alkyl-COR4,
  (xvi) ($C_1$-$C_4$)alkoxy-COR5,
  (xvii) $NHSO_2R^6$,
  (xviii) $SO_2R^7$,
  (xix) $NHCOR^8$,
  (xx) $SOR^9$,
  (xxi) $SR^{10}$,
  (xxii) $CONHR^{11}$, and
  (xxiii) O—$(CH_2)_q$-$NR^{12}R^{13}$, wherein q represents 1-4;
 (c) thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl,;
 (d) thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl optionally substituted one to three times with a substituent independently selected from the group consisting of:
  (i) fluoro, bromo, or chloro,
  (ii) amino,
  (iii) ($C_1$-$C_4$)alkyl,
  (iv) ($C_1$-$C_4$)alkoxy,
  (v) $COR^3$, or
  (vi) $SO_2R^7$,
 (e) benzimidazole, benzofuran, benzothiophene, benzo[1,3]-dioxolyl, benzothiazole, 2,2-dioxy-2,3-dihydro-1H-2$\lambda^6$-benzo[c]thiophene, or indole;
 (f) benzimidazole, benzofuran, benzothiophene, benzo[1,3]-dioxolyl, benzothiazole, 2,2-dioxy-2,3-dihydro-1H-2$\lambda^6$-benzo[c]thiophene, and indole optionally substituted one or two times with a substituent independently selected from the group consisting of:
  (i) amino, or
  (ii) ($C_1$-$C_4$)alkyl
 or (g) cyclohexyl;
(E) R2 represents:
 (a) phenyl;
 (b) phenyl optionally substituted one to three times with a substituent independently selected from the group consisting of:
  (i) fluoro, bromo, or chloro,
  (ii) amino,
  (iii) nitro,
  (iv) hydroxy,
  (v) cyano,
  (vi) methyl, ethyl, propyl, butyl, i-butyl,
  (vii) methoxy or ethoxy,
  (viii) aminomethyl or aminoethyl,
  (ix) hydroxy methoxy or hydroxy ethoxy,
  (x) 2-fluoro ethoxy or 2-trifluoro ethoxy,
  (xi) methoxy ethoxy,
  (xii) trifluoromethyl,
  (xiii) cyclohexyl,
  (xiv) $COR^3$,
  (xv) ($C_1$-$C_4$)alkyl-COR4,
  (xvi) ($C_1$-$C_4$)alkoxy-COR5,
  (xvii) $NHSO_2R^6$,
  (xviii) $SO_2R^7$,
  (xix) $NHCOR^8$,
  (xx) $SOR^9$,
  (xxi) $SR^{10}$,
  (xxii) $CONHR^{11}$, and
  (xxiii) O—$(CH_2)_q$-$NR^{12}R^{13}$, wherein q represents 1-4;
 (c) thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl;
 (d) thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl optionally substituted one to three times with a substituent independently selected from the group consisting of:
  (i) fluoro, bromo, or chloro,
  (ii) amino,
  (iii) methyl,
  (iv) methoxy,
  (v) $COR^3$, or
  (vi) $SO_2R^7$;
 (e) benzimidazole, benzofuran, benzothiophene, benzo[1,3]-dioxolyl, benzothiazole, 2,2-dioxy-2,3-dihydro-1H-2$\lambda^6$-benzo[c]thiophene, or indole;
 (f) benzimidazole, benzofuran, benzothiophene, benzo[1,3]-dioxolyl, benzothiazole, 2,2-dioxy-2,3-dihydro-1H-2$\lambda^6$-benzo[c]thiophene, and indole optionally substituted one or two times with a substituent independently selected from the group consisting of:
  (i) amino, or
  (ii) methyl;
 or (g) cyclohexyl;
(F) R2 represents:
 (a) phenyl;
 (b) phenyl optionally substituted one to three times with a substituent independently selected from the group consisting of:
  (i) fluoro, bromo, or chloro,
  (ii) amino,
  (iii) nitro,
  (iv) hydroxy,
  (v) cyano,
  (vi) methyl, ethyl, propyl, butyl, i-butyl,
  (vii) methoxy or ethoxy,
  (viii) aminomethyl or aminoethyl,
  (ix) hydroxy methoxy or hydroxy ethoxy,
  (x) 2-fluoro ethoxy or 2-trifluoro ethoxy,
  (xi) methoxy ethoxy,
  (xii) trifluoromethyl,
  (xiii) cyclohexyl,
  (xiv) $COR^3$, wherein $R^3$ represents amino, hydroxy, ($C_1$-$C_4$)alkyl, ($C_1$-$C_4$)alkoxy, N,N—($C_1$-$C_4$)dialkylamine, or a heterocycle selected from the group consisting of:

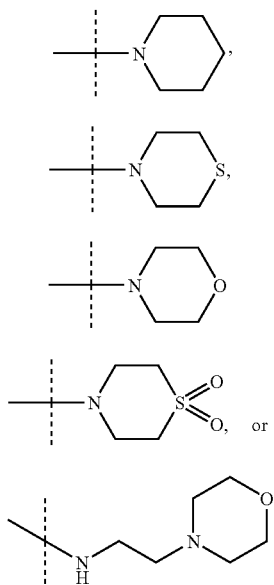

(xv) (C$_1$-C$_4$)alkyl-COR4, wherein R4 represents hydroxy, amino, or (C$_1$-C$_4$)alkoxy, (xvi) (C$_1$-C$_4$)alkoxy-COR5, wherein R5 represents hydroxy or amino, (xvii) NHSO$_2$R$^6$, wherein R6 represents (C1-C4)alkyl, (xviii) SO$_2$R$^7$, wherein R7 represents amino or (C1-C4)alkyl, (xix) NHCOR$^8$, wherein R8 represents methyl, (xx) SOR$^9$, wherein R9 represents methyl, (xxi) SR$^{10}$, wherein R10 represents methyl or ethyl, (xxii) CONHR$^{11}$, wherein R11 represents —(CH$_2$)n-X—Y, where n=0-2, X represents —S—, —CH$_2$—, —(CH$_2$)$_2$—, —NH—, —CO—, or —SO$_2$—, and Y represents amino, (C$_1$-C$_4$)alkyl, (C$_1$-C$_4$)alkoxycarbonyl, or NH— (C$_1$-C$_4$)alkylamine;

or wherein R11 represents CH(COR14)—(CH$_2$)m-X'—Y" where R14 represents hydroxy or (C$_1$-C$_4$)alkoxy, m=0-4, X' represents —S—, —CH$_2$—, —NH—, or —CO—, and Y' represents represents amino, hydroxy, (C$_1$-C$_4$)alkyl, or (C$_1$-C$_4$)alkoxycarbonyl; or wherein R11 represents a group selected from the following:

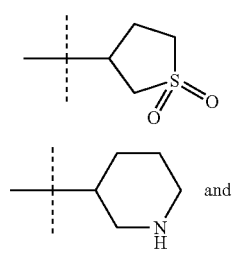

(xxiii) O—(CH$_2$)q-NR$^{12}$R$^{13}$, wherein q represents 1-3, R12 and R13 independently represent hydrogen or methyl or R12 and R13 together with the nitrogen to which they are attached form a piperidino, pyrrolidino, morpholino or a methylpiperazino group;

(c) thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl;

(d) thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl optionally substituted one to three times with a substituent independently selected from the group consisting of:
(i) fluoro, bromo, or chloro,
(ii) amino,
(iii) methyl,
(iv) methoxy,
(v) COR$^3$, wherein R3 represents hydroxy, (C$_1$-C$_4$) alkoxy or pyridine,
(vi) SO$_2$R$^7$, wherein R7 represents amino (e) benzimidazole, benzofuran, benzothiophene, benzo[1,3]-dioxolyl, benzothiazole, 2,2-dioxy-2,3-dihydro-1H-2λ$^6$-benzo[c]thiophene, or indole;

(f) benzimidazole, benzofuran, benzothiophene, benzo[1,3]-dioxolyl, benzothiazole, 2,2-dioxy-2,3-dihydro-1H-2λ$^6$-benzo[c]thiophene, and indole optionally substituted one or two times with a substituent independently selected from the group consisting of:
(i) amino, or
(ii) methyl;

or (g) cyclohexyl;

(G) The particular embodiments of any of groupings (C) through (F) wherein when R2 represents a substituted aryl or heterocycle, said aryl or heterocycle is substituted 1 or 2 times.

(H) The particular embodiments of any of groupings (C) through (F) wherein when R2 represents a substituted aryl or heterocycle, said aryl or heterocycle is substituted once.

(I) The particular embodiments of any of groupings (C) through (F) wherein when R2 represents a substituted benzofused heterocycle, said benzofused heterocycle is substituted once.

(J) R2 represents phenyl or phenyl optionally substituted one to three times with a substituent independently selected from the group consisting of:
(i) halo,
(ii) amino,
(iii) nitro,
(iv) hydroxy,
(v) cyano,
(vi) (C$_1$-C$_4$)alkyl,
(vii) (C$_1$-C$_4$)alkoxy, (viii) amino($C_1$-$C_4$)alkyl
(ix) hydroxy($C_1$-$C_4$)alkoxy,
(x) halo($C_1$-$C_4$)alkoxy,
(xi) ($C_1$-$C_4$)alkoxy($C_1$-$C_4$)alkoxy,
(xii) trifluoromethyl,
(xiii) ($C_3$-$C_7$)cylcoalkyl,
(xiv) $COR^3$,
(xv) ($C_1$-$C_4$)alkyl-COR4,
(xvi) ($C_1$-$C_4$)alkoxy-COR5,
(xvii) $NHSO_2R^6$,
(xviii) $SO_2R^7$,
(xix) $NHCOR^8$,
(xx) $SOR^9$,
(xxi) $SR^{10}$,
(xxii) $CONHR^{11}$, and
(xxiii) O—($CH_2$)q-$NR^{12}R^{13}$, wherein q represents 1-4,
(K) R2 represents phenyl or phenyl optionally substituted one to three times with a substituent independently selected from the group consisting of:
(i) fluoro, bromo, or chloro,
(ii) amino,
(iii) nitro,
(iv) hydroxy,
(v) cyano,
(vi) methyl, ethyl, propyl, butyl, i-butyl,
(vii) methoxy or ethoxy,
(viii) aminomethyl or aminoethyl,
(ix) hydroxy methoxy or hydroxy ethoxy,
(x) 2-fluoro ethoxy or 2-trifluoro ethoxy,
(xi) methoxy ethoxy,
(xii) trifluoromethyl,
(xiii) cyclohexyl,
(xiv) $COR^3$,
(xv) ($C_1$-$C_4$)alkyl-COR4,
(xvi) ($C_1$-$C_4$)alkoxy-COR5,
(xvii) $NHSO_2R^6$,
(xviii) $SO_2R^7$,
(xix) $NHCOR^8$,
(xx) $SOR^9$,
(xxi) $SR^{10}$,
(xxii) $CONHR^{11}$, and
(xxiii) O—($CH_2$)q-$NR^{12}R^{13}$, wherein q represents 1-4,
(L) R2 represents phenyl or phenyl optionally substituted one to three times with a substituent independently selected from the group consisting of:
(i) fluoro, bromo, or chloro,
(iii) amino,
(iv) nitro,
(v) hydroxy,
(vi) cyano,
(vii) methyl, ethyl, propyl, butyl, i-butyl,
(viii) methoxy or ethoxy,
(ix) aminomethyl or aminoethyl,
(x) hydroxy methoxy or hydroxy ethoxy,
(xi) 2-fluoro ethoxy or 2-trifluoro ethoxy,
(xii) methoxy ethoxy,
(xiii) trifluoromethyl,
(xiv) cyclohexyl,
(xiv) $COR^3$, wherein R3 represents amino, hydroxy, ($C_1$-$C_4$)alkyl, ($C_1$-$C_4$)alkoxy, N,N—($C_1$-$C_4$)dialkylamine, or a heterocycle selected from the group consisting of:

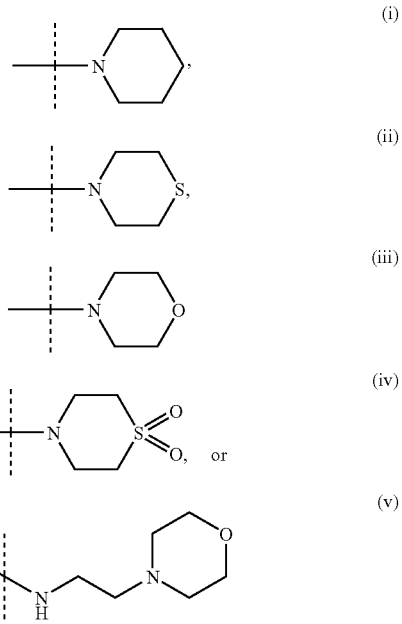

(xv) ($C_1$-$C_4$)alkyl-COR4, wherein R4 represents hydroxy, amino, or ($C_1$-$C_4$)alkoxy,
(xvi) ($C_1$-$C_4$)alkoxy-COR5, wherein R5 represents hydroxy or amino,
(xvii) $NHSO_2R^6$, wherein R6 represents (C1-C4)alkyl,
(xviii) $SO_2R^7$, wherein R7 represents amino or (C1-C4) alkyl,
(xix) $NHCOR^8$, wherein R8 represents methyl,
(xx) $SOR^9$, wherein R9 represents methyl,
(xxi) $SR^{10}$, wherein R10 represents methyl or ethyl,
(xxii) $CONHR^{11}$, wherein R11 represents —($CH_2$)n-X—Y, where n=0-2, X represents —S—, —$CH_2$—, —($CH_2$)$_2$—, —NH—, —CO—, or —$SO_2$—, and Y represents amino, ($C_1$-$C_4$)alkyl, ($C_1$-$C_4$)alkoxycarbonyl, or NH—($C_1$-$C_4$)alkylamine;
or wherein R11 represents CH(COR14)—($CH_2$)m-X'—Y" where R14 represents hydroxy or ($C_1$-$C_4$) alkyl, m=0-4, X' represents —S—, —$CH_2$—, —NH—, or —CO—, and Y' represents represents amino, hydroxy, ($C_1$-$C_4$)alkyl, or ($C_1$-$C_4$)alkoxycarbonyl; or wherein R11 represents a group selected from the following:

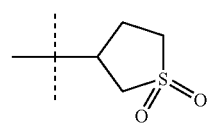

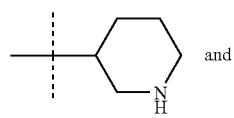

and

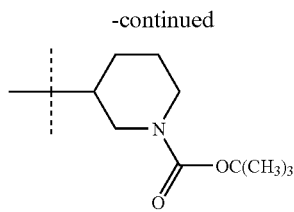

(xxiii) O—(CH$_2$)q-NR$^{12}$R$^{13}$, wherein q represents 1-3, R12 and R13 independently represent hydrogen or methyl or R12 and R13 together with the nitrogen to which they are attached form a piperidino, pyrrolidino, morpholino or a methylpiperazino group;

(M) R2 represents phenyl, 4-(N-acetylamino)phenyl, 2-hydroxyphenyl, 3-hydroxyphenyl, 4-hydroxyphenyl, 2-aminophenyl, 3-aminophenyl, 4-aminophenyl, 3-chlorophenyl, 4-chlorophenyl, 3-nitrophenyl, 4-nitrophenyl, 3-(methylsulfonylamino)phenyl, 4-(methylsulfonylamino)phenyl, 2-ethoxyphenyl, 3-ethoxyphenyl, 4-ethoxyphenyl, 4-methoxyphenyl, 4-fluoro-3-methylphenyl, 4-Fluoro-2-methylphenyl, 4-bromophenyl, 4-ethylsulfanylphenyl, 4-methylsulfanylphenyl, 4-cyanophenyl, 4-acetylphenyl, 2-carboxamidophenyl, 4-(2-carboxy-eth-1-yl)phenyl, 3,5-dichlorophenyl, 3,4-dichlorophenyl, 4-methoxy-3-methylphenyl, 3-amino-4-methylphenyl, 2-nitrophenyl, 3-(N-acetylamino)phenyl, 4-methanesulfinylphenyl, 4-methyl-3-nitrophenyl, 4-carboxyphenyl, 3,5-Bis-trifluoromethylphenyl, 3-carboxyphenyl, 2-carboxyphenyl, 4-isobutylphenyl, 4-carboxymethoxy phenyl, 4-methyl-3-nitro-phenyl, 4-cyclohexyl-phenyl, 4-fluorophenyl, 4-methoxyphenyl, 4-(2-hydroxy ethoxy)phenyl, 4-carboxymethylphenyl, 4-methanesulfonylphenyl, 4-(2-amino eth-1-yl)phenyl, 4-methylphenyl, 2-fluoro-4-aminophenyl, 3,5-bis carboxyphenyl, 3,5-bis methoxycarbonyl phenyl, 3-chloro-4-aminophenyl, 3-chloro-5-fluoro-4-hydroxyphenyl, 4,5-difluoro-3-hydroxyphenyl, 4-aminosulfonyl phenyl, 3-aminosulfonyl phenyl, 2-aminosulfonyl phenyl, 4-(2-methoxycarbonyl)eth-1-yl phenyl, 4-(2-carboxamido) eth-1-yl phenyl, 4-(2-(N,N-dimethylamino) ethoxy)phenyl, 4-(2-morpholin-4-yl-ethoxy)phenyl, 4-(2-Piperidin-1-yl-ethoxy)phenyl, 4-(2-Piperidin-1-yl-ethoxy)phenyl, 4-(2-Piperidin-1-yl-ethoxy)phenyl, 4-(3-(N,N-dimethylamino)propoxy)phenyl, 4-(3-Morpholin-4-yl-propoxy)phenyl, 4-(3-pyrrolidin-1-yl-propoxy)phenyl, 4-[3-(4-Methylpiperazin-1-yl)propoxy]phenyl, 4-carboxamido-methoxyphenyl, 4-(2-methoxyethoxy)phenyl, 4-(2-fluoroethoxy)phenyl, 4-(2-trifluoroethoxy)phenyl, 4-(N-(2-N-(tert-butoxycarbonyl)amino eth-1-yl)carboxamido)phenyl, 4-(piperidin-1-yl carbonyl)phenyl, 4-(thiomorpholin-4-yl carbonyl)phenyl, 4-(morpholin-4-carbonyl)phenyl, 4-(N-acetamido carboxamido)phenyl, 4-(N-(2-N,N-dimethylamino eth-1-yl)carboxamido)phenyl, 4-(N-(2-tert-butylsulfanyl-eth-1-yl)carboxamido)phenyl, 4-(N-(2-ethoxycarbonyl eth-1-yl)carboxamido)phenyl, 4-(N-(1,1-dioxo-tetrahydro-1λ6-thiophen-3-yl) carboxamido)phenyl, 4-(N-(1-tert-butoxycarbonyl piperidin-3-yl)carboxamido)phenyl, 4-(N-(5-N-tert-butoxycarbonylamino-1-tert-butoxycarbonyl pent-1-yl) carboxamido)phenyl, 4-(N-(2-(morpholin-4-yl)eth-1-yl)carboxamido)phenyl, 4-(1,1-dioxo-1λ6-thiomorpholin-4-yl)carbonyl phenyl, 4-(N-(2-methylsulfanyl-1-tert-butoxycarbonyl-eth-1-yl) carboxamido)phenyl, 4-(N-(1,3-bis-tert-butoxycarbonyl-prop-1-yl)carboxamido)phenyl, 4-(N,N-dimethylcarboxamido)phenyl, 4-(N-(2-ter-butoxycarbonyl-eth-1-yl)carboxamido)phenyl, 4-N-methylcarboxamido phenyl, 4-(N-(2-methylsulfonyl-eth-1-yl)carboxamido)phenyl, 4-(N—(N,N-dimethylamino)carboxamido)phenyl, 4-carboxamido phenyl, 4-(N-(2 amino-eth-1-yl)carboxamido)phenyl, 4-(N-(5-amino-1-carboxy-pent-1-yl)carboxamido)phenyl, 4-(N-piperidin-3-yl carboxamido)phenyl, 4-(N-(2-methylsufanyl-1-carboxy-eth-1-yl)carboxamido)phenyl, 4-(N-(1,3-bis carboxy-prop-1-yl)carboxamido) phenyl, or 4-(N-(2-carboxy eth-1-yl)carboxamido) phenyl;

(N) R2 represents thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, dioxo-thiomorpholinyl; or thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl optionally substituted one to three times with a substituent independently selected from the group consisting of:
(i) fluoro, bromo, or chloro,
(ii) amino,
(iii) (C$_1$-C$_4$)alkyl,
(vii) (C$_1$-C$_4$)alkoxy,
(viii) COR$^3$, and
(ix) SO$_2$R$^7$, (O) R$^2$ represents thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, dioxo-thiomorpholinyl; or thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl optionally substituted one to three times with a substituent independently selected from the group consisting of:
(i) fluoro, bromo, or chloro,
(ii) amino,
(vii) methyl,
(viii) methoxy,
(ix) COR$^3$, or
(x) SO$_2$R$^7$;

(P) R2 represents thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, dioxo-thiomorpholinyl; or thiopheneyl, furanyl, imidazolyl, pyrazolyl, pyrrolyl, thiazolyl, triazolyl, pyridinyl, pyrimidyl, pyrazinyl, pyridiazinyl, piperidinyl, piperazinyl, pyrimidinyl, or dioxo-thiomorpholinyl optionally substituted one to three times with a substituent independently selected from the group consisting of:
(i) fluoro, bromo, or chloro,
(ii) amino,
(iii) methyl,
(iv) methoxy,
(v) COR$^3$, wherein R3 represents hydroxy or (C$_1$-C$_4$) alkoxy,
(vi) SO$_2$R$^7$, wherein R7 represents amino, (Q) R2 represents thiophen-2-yl, thiophen-3-yl, pyridin-4-yl, pyridin-3-yl, furan-3-yl, furan-2-yl, thiazol-2-yl, pyrazin-2-yl, pyridin-2-yl, 1H-pyrrol-2-yl, 1H-pyrrol-3-yl, pyrimidin-2-yl, pyrimidin-5-yl, imidazol-1-yl, [1,2,4]triazol-1-yl, pyrazol-1-yl, [1,2,3]triazol-1-yl, piperidin-1-yl, 1,1-Dioxo-1λ6-thiomorph-olin-4-yl, piperazin-1-yl, 4-methylthiophen-2-yl, 6-carboxypyridin-2-yl, 5-fluoropyridin-2-yl, 6-methoxypyridazin-3-yl, 2-aminopyrimidin-5-yl, 5-aminosulfonyl thiophen-2-yl, or 4-tert-butoxycarbonyl piperazin-1-yl;

(R) R2 represents benzimidazole, benzofuran, benzothiophene, benzo[1,3]-dioxolyl, benzothiazole, 2,2-dioxy-2,3-dihydro-1H-2$\lambda^6$-benzo[c]thiophene, indole; or benzoimidazole, benzofuran, benzothiophene, benzo[1,3]-dioxolyl, benzothiazole, 2,2-dioxy-2,3-dihydro-1H-2$\lambda^6$-benzo[c]thiophene, or indole optionally substituted one or two times with a substituent independently selected from the group consisting of:
(i) amino, or
(ii) ($C_1$-$C_4$)alkyl (S) R2 represents benzimidazole, benzofuran, benzothiophene, benzo[1,3]-dioxolyl, benzothiazole, 2,2-dioxy-2,3-dihydro-1H-2$\lambda^6$-benzo[c]thiophene, indole; or benzoimidazole, benzofuran, benzothiophene, benzo[1,3]-dioxolyl, benzothiazole, 2,2-dioxy-2,3-dihydro-1H-2$\lambda^6$-benzo[c]thiophene, or indole optionally substituted one or two times with a substituent independently selected from the group consisting of:
(i) amino, or
(ii) methyl;

(T) R represents 1H-Indol-5-yl, Benzo[1,3]dioxol-5-yl, Benzo[b]thiophen-2-yl, Benzofuran-2-yl, 4-Benzo[b]thiophen-3-yl, 1H-Indol-2-yl, 2,2-Dioxy-2,3-dihydro-1H-2$\lambda^6$-benzo[c]thiophen-5-yl, 1H-benzoimidazol-2-yl, or 2-amino benzothiazol-6-yl; or (U) R2 represents cyclohexyl.

(V) The particular embodiments of any of groupings (J), (K), (L), (N), (O), or (P) wherein when R2 represents a substituted aryl or heterocycle, said aryl or heterocycle is substituted 1 or 2 times.

(W) The particular embodiments of any of groupings (J), (K), (L), (N), (O), or (P) wherein when R2 represents a substituted aryl or heterocycle, said aryl or heterocycle is substituted once.

(X) The particular embodiments of any of groupings (R) or (S) wherein when R2 represents a substituted benzofused heterocycle, said benzofused heterocycle is substituted once.

Compounds of Formula I can be chemically prepared, for example, by following the synthetic routes set forth in the Schemes and the Preparations and Examples below. However, the Schemes contained in the following discussion are not intended to be limiting to the scope of the present invention in any way. For example, the specific synthetic steps for the routes described herein may be combined in different ways, or with steps from different schemes, to prepare other compounds of Formula I. All substituents, unless otherwise indicated, are as previously defined. The reagents and starting materials are readily available to one of ordinary skill in the art. For example, certain reagents or starting materials can be prepared by one of ordinary skill in the art following procedures disclosed in Larock, R. C., *Comprehensive Organic Transformations*, $2^{nd}$ Ed., copyright 1999, John Wiley & Sons, pp 741-742; Miryaura, N.; Yanagi, T.; Suzuki, A. The Palladium-Catalyzed Cross Coupling Reaction of Phenylboronic Acid with Haloarenes in the Presence of Bases. *Synth. Commun.*, 1981, 513-518; Stanforth, S. P. *Tetrahedron*, 1998, 54, 263-303; Greene, T. W.; Wuts, P. G. M. *Protective Groups in Organic Synthesis* ($3^{rd}$ ed.); Wiley: New York, 1999; Ishiyama, T.; Murata, M.; Miyaura, N. *J. Org. Chem.* 1995, 60, 7508-7510; Lindley, J. *Tetrahedron* 1984, 40, 1433-1456; Wolfe, J. P.; Buchwald, S. L. *J. Org. Chem.* 1997, 62, 6066-6068; Furniss, B. S.; Hannaford, A. J.; Smith, P. W. G.; Tatchell, A. R. *Vogel's Textbook of Practical Organic Chemistry* ($5^{th}$ ed.); Longman, Essex, 1989; p 1077-1079; Bodanszky, M.; Bodanszky, A. *The Practice of Peptide Synthesis*; Springer Verlag: New York, 1984; Smith, D. L.; McCloskey J. A.; *J. Org. Chem.* 43, 2087-2088, 1978.

Other necessary reagents and starting material may be made by procedures which are selected from standard techniques of organic and heterocyclic chemistry, techniques which are analogous to the syntheses of known structurally similar compounds, and the procedures described in the Preparations and Examples, including any novel procedures.

The Preparations and Examples that follow further illustrate the invention and represent typical synthesis of the compounds of Formula I as described generally above. The reagents and starting materials are readily available to one of ordinary skill in the art. Where used herein, the following terms have the meanings indicated: "eq" or "equiv." refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether; "$PPh_3$" refers to triphenylphosphine; "DEAD" refers to diethyl azodicarboxylate; "RT" refers to room temperature; "Pd—C" refers to palladium over carbon; "$NaBH(Oac)_3$" refers to sodium triacetoxyborohydride; "Bn" refers to benzyl; "$BnNH_2$" refers to benzyl amine; "$H_2$" refers to hydrogen; "$CH_2Cl_2$" refers to dichloromethane; "HBTU" refers to O-Benzotriazol-1-yl-N,N,N',N'-tetramethyluronium hexafluorophosphate, "MPLC" refers to medium-pressure-liquid chromatography; "NMR" refers to nuclear magnetic resonance spectroscopy; "MS" refers to mass spectroscopy; "ES+" refers to positive mode electrospray ionization; and "M" refers to molecular weight.

Analytical Methods

The compounds of the present invention may be purified by methods known to one skilled in the art. These methods include crystallization, precipitation, normal phase silica gel chromatography and reverse-phase high-performance chromatography that is mass-guided and/or UV-guided. The purity of compounds is determined by LC/MS analysis.

The salt composition is determined by HPLC analysis. The HPLC system consists of a Shimadzu SCL-10A controller, SIL-10A auto injector, LC10AS pump, and a SPD-10A UV detector (Kyoto, Japan). The Prevail Organic Acid column (25 cm×4.6 mm I.D.) is obtained from Alltech Associates Inc. (Deerfield, Ill.). The HPLC operating conditions consist of a mobile phase comprising 0.2M KH2PO4 (no pH adjustment). The mobile phase flow rate is set at 1.5 mL/minute with sample injections of 10 µL. The UV detector is set at 195 nm and run time is 3 minutes. TFA is quantitated by linear regression of peak area response versus standards prepared at known TFA concentrations.

Enabling Chemistries: (Preparation of Intermediates)

Scheme 1

Synthesis of 5,6-dihydro-4H-pyrrolo[1,2-b]pyrazole derivatives

Scheme 1 depicts the synthesis of the dihydro-4H-pyrrolo [1,2-b]pyrazole core structure, substituted by heteroaromatics, preferably pyridine (with or without substitution) and quinoline. The quinoline may be substituted as well with a variety of aromatic or heterocyclic rings, specifically at the 7-position of the quinoline. In step A, a quinoline of Formula 2 can be prepared by reaction of an aniline with a vinyl ketone in the presence of an appropriate acid catalyst such as conc. $H_2SO_4$ in a suitable solvent such as dioxane. The resulting quinoline (step B) is sequentially treated with a strong base such as potassium hexamethyldisilazide, lithium hexamethyl-disilazide, or lithium diisopropyl amide at −78° C. in a suitable solvent such as tetrahydrofuran, and treated with a picolonic acid ester of Formula 3, such as methyl picolinate, which may be additionally substituted on the pyridine ring, to yield a methyl ketone of Formula 4. Condensation of the methyl ketone (step C) with 1-aminopyrrolidinone hydrochloride (Formula 5) provides an imine of Formula 6 under basic conditions at room temperature (pyridine/ethanol or sodium ethoxide in ethanol). The imine undergoes cyclization by treatment with base such as sodium hydride or cesium carbonate under standard conditions (step D) to yield the 5,6-dihydro-4H-pyrrolo[1,2-b]pyrazole (Formula 7) with appropriate pyridyl and quinolinyl substitution.

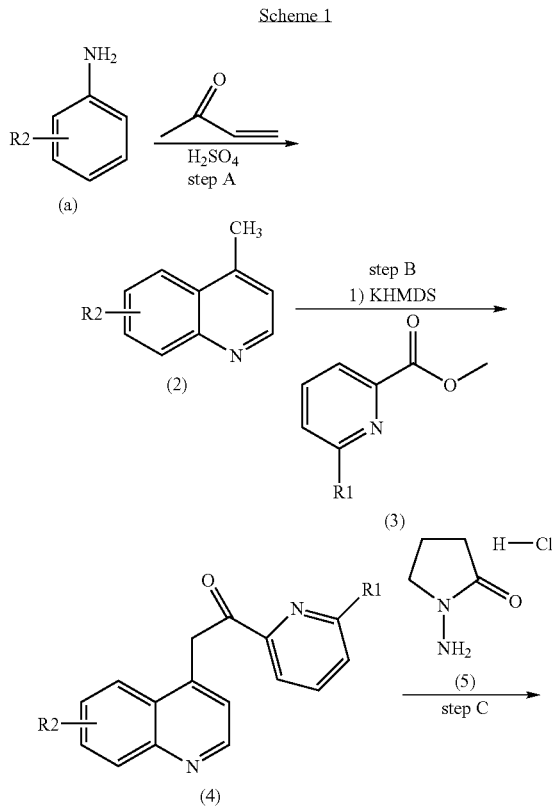

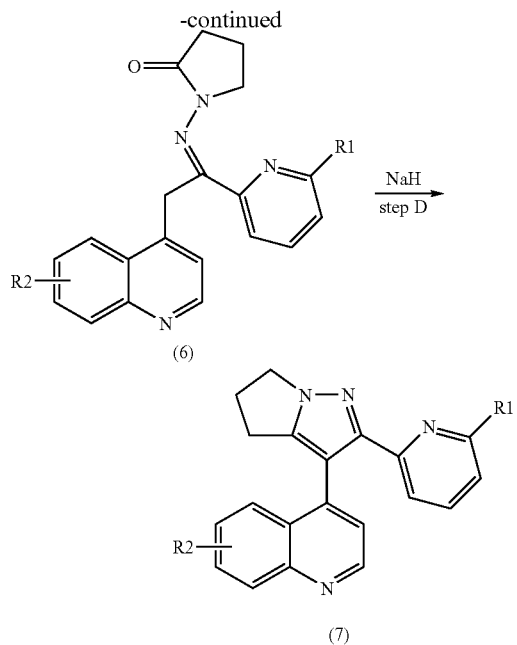

Preparation 1

1-Aminopyrrolidin-2-one Hydrochloride

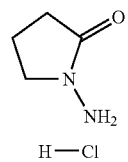

4-Chlorobutyryl chloride (57 mL, 510 mmol) is added to a solution of benzophenone hydrazone (100 g, 510 mmol) and pyridine (41 mL, 510 mmol) in anhydrous $CH_2Cl_2$ (520 mL) under nitrogen at a rate that maintained a gentle reflux throughout the addition. The mixture is stirred for 0.5 h and poured into water (1 L). The layers are separated and the organic layer is washed with brine, dried ($Na_2SO_4$), filtered, and concentrated in vacuo to yield 4-chloro-butyric acid benzhydrylidene-hydrazide as a residue.

MS ES+ m/e 301.1 (M+1).

This residue is dissolved in THF (1.5 L), and the solution cooled in an ice-water bath, treated with portions of NaH (60% suspended in mineral oil, 20 g, 498 mmol) and stirred for 1 h. To the mixture is added saturated aqueous $NH_4Cl$ solution (1 L) and EtOAc (1 L). The layers are separated and the organic solution washed with brine, dried ($Na_2SO_4$), filtered and concentrated in vacuo to yield 1-(benzhydrylideneamino)pyrrolidin-2-one as a residue.

$^1$H NMR ($CDCl_3$): δ 7.58-7.62 (m, 2H), 7.39-7.46 (m, 4H), 7.29-7.36 (m, 4H) 3.31 (t, J=7 Hz, 2H), 2.32 (t, J=7 Hz, 2H), 1.91 (quintet, J=7 Hz, 2H); MS ES+ m/e 265.1 (M+1).

This residue is suspended in water (3 L), treated with concentrated HCl solution (80 mL), and heated to reflux for 1.5 h. The reaction is cooled to RT and extracted twice with $CH_2Cl_2$. The aqueous portion is concentrated in vacuo followed by azeotropic removal of water with three portions of absolute ethanol and three portions of toluene to yield the title compound, 56 g (81%), as a white solid.

$^1$H NMR (DMSO-d$_6$): δ 3.58 (t, J=7 Hz, 2H), 2.33 (t, J=7 Hz, 2H), 2.04 (quintet, J=7 Hz, 2H), TOF MS ES$^+$ exact mass calculated for C$_4$H$_8$N$_2$ (M+): m/z=100.0637. Found: 100.0641.

Preparation 2

6-Methylpyridine-2-carboxylic Acid Methyl Ester

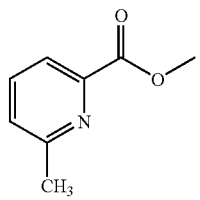

To a suspension of 6-methyl-pyridine-2-carboxylic Acid (10 g, 72.9 mmol) in CH$_2$Cl$_2$ (200 mL) cooled to 0° C. is added MeOH (10 mL), 4-dimethylaminopyridine (11.6 g, 94.8 mmol), and EDC (18.2 g, 94.8 mmol). The mixture is stirred at RT for 6 h, washed with water and brine, and dried over Na$_2$SO$_4$. The mixture is filtered and concentrated in vacuo and the residue is chromatographed on silica gel (50% EtOAc/Hexanes) to yield the title compound, 9.66 g (92%), as a colorless liquid.

$^1$H NMR (CDCl$_3$) δ 7.93-7.88 (m, 1H), 7.75-7.7 (m, 1H), 7.35-7.3 (m, 1H), 4.00 (s, 3H), 2.60 (s, 3H).

Preparation 3

7-Bromo-4-methylquinoline

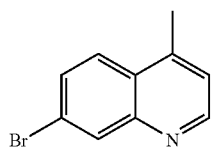

H$_2$SO$_4$ (14.4 mL, 270 mmol) is added to a solution of 3-bromoaniline (Aldrich, 30.0 g, 174 mmol) in 1,4-dioxane (1 L) at RT. The mixture is heated to reflux and treated with methyl vinyl ketone (Aldrich, 19.5 mL, 270 mmol) in 1,4-dioxane (50 mL) dropwise over 3 h. Heating is continued for 1 h after the addition, followed by removal of the solvent in vacuo. The residue is dissolved in water (100 mL), neutralized with Na$_2$CO$_3$ and extracted with CH$_2$Cl$_2$. The combined organic extracts are washed with water and brine, dried (Na$_2$SO$_4$) and filtered. The filtrate is concentrated, and the residue chromatographed on silica gel (Biotage, eluting with 20% EtOAc/Hexanes) to give the title compound, 15.0 g (43%), as a brownish solid.

$^1$H NMR (CDCl$_3$) δ 8.80-8.75 (m, 1H), 8.30 (s, 1H), 7.90-7.85 (m, 1H), 7.70-7.65 (m, 1H), 7.25-7.20 (m, 1H), 2.65 (s, 3H).

Preparation 4

2-(7-Bromoquinolin-4-yl)-1-(6-methylpyridin-2-yl) ethanone

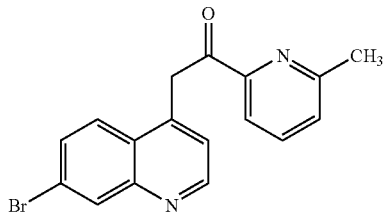

7-Bromo-4-methyl-quinoline (2.75 g, 12.4 mmol) is dissolved in THF (33 mL), cooled to −78° C., treated with KHMDS solution (Aldrich, 0.5 M in toluene, 29.8 mL, 14.9 mmol) and stirred for 40 min. The mixture is treated with the product of Preparation 2 (2.44 g, 16.1 mmol) and stirred for 2 h, and then warmed to RT for 2 h. After adding saturated NH$_4$Cl solution (5 mL), the mixture is concentrated in vacuo. The residue is chromatographed on silica gel (eluting with 50% EtOAc/Hexanes) to give the title compound, 2.3 g (66%), as a yellow solid.

$^1$H NMR (CDCl$_3$) δ 8.85 (m, 1H), 8.30 (s, 1H), 8.00-7.60 (m, 4H), 7.45-7.35 (m, 2H), 5.05 (s, 2H), 2.65 (s, 3H).

The following compound is prepared by the previous method (4):

| PREP# | Product Name | Physical Data |
| --- | --- | --- |
| 5 | 2-(7-Bromoquinolin-4-yl)-1-pyridin-2-yl-ethanone | $^1$H NMR (CDCl$_3$) δ 8.85 (m, 1H), 8.30 (s, 1H), 8.00-7.60 (m, 4H), 7.45-7.35 (m, 3H), 5.05 (s, 2H) |

Preparation 6

1-[2-(7-Bromoquinolin-4-yl)-1-(6-methylpyridin-2-yl)-ethylideneamino]pyrrolidin-2-one

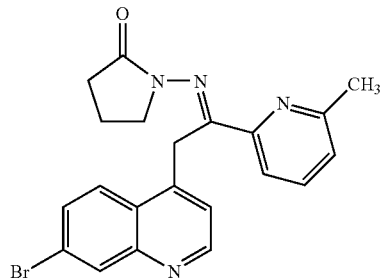

The product of Preparation 4 (1.3 g, 1.47 mmol), the product of Preparation 1 (0.315 g, 2.31 mmol) and pyridine (1.47 mL) are dissolved in EtOH (6 mL) and stirred for 18 h. The mixture is concentrated to dryness and the residue chromatographed on silica gel (90% EtOAc/Hexanes) to give the title compound, 1.2 g (75%), as a yellow foam.

$^1$H NMR (CDCl$_3$) δ 8.80-8.75 (m, 1H), 7.95-7.85 (m, 2H), 7.70-7.60 (m, 1H), 7.45-7.20 (m, 4H), 4.90 (s, 2H), 3.10-3.00 (m, 2H), 2.20-2.15 (m, 2H), 1.48-1.35 (m, 2H).

The following compound is prepared by the previous method (6):

| Prep# | Product Name | Physical Data |
|---|---|---|
| 7 | 1-[2-(7-Brom-quinolin-4-yl)-1-pyridin-2-yl-ethylideneamino]-pyrrolidin-2-one | $^1$H NMR (CDCl$_3$) δ 8.72 (d, J = 4.5 Hz, 1H), 8.60 (d, J = 4.5 Hz, 1H), 8.30 (d, J = 2.0 Hz, 1H), 8.15 (dd, J = 7.8, 1.0 Hz, 1H), 7.95 (d, J = 9.0 Hz, 1H), 7.80 (dt, J = 2.0, 7.8 Hz, 1H), 7.58 (dd, J = 2.0, 9.0 Hz, 1H), 7.40 (dd, J = 4.5, 7.8 Hz, 1H), 7.20 (m, 1H), 4.90 (s, 2H), 3.10 (t, J = 6.8 Hz, 2H), 2.22 (t, J = 6.8 Hz, 2H), 1.44 (q, J = 6.8 Hz, 2H) |

Preparation 8

7-Bromo-4-[2-(6-methylpyridin-2-yl)-5,6-dihydro-4H-pyrrolo[1,2-b]pyrazol-3-yl]quinoline

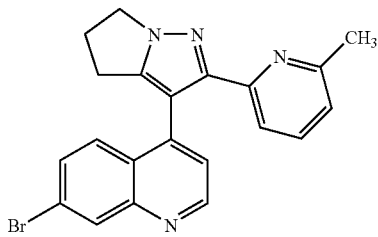

The product of Preparation 6 (0.21 g, 0.58 mmol) is dissolved in DMF (4 mL) and NaH (60% in mineral oil, 0.033 g, 0.87 mmol) is added at RT under nitrogen. After stirring for 10 min, the mixture is heated to 80° C. overnight, then cooled to RT. Saturated NH$_4$Cl solution (0.5 mL) is added and after stirring for 10 min, the mixture is concentrated in vacuo. Chromatography of the yellow residue on silica gel (50% EtOAc/Hexanes) provides the title compound, 0.13 g (65%), as a yellow foam.

$^1$H NMR (CDCl$_3$) δ 8.90-8.88 (m, 1H), 7.55-7.50 (m, 1H), 7.30-7.15 (m, 4H), 7.05-7.00 (m, 1H), 6.90-6.88 (m, 1H), 4.35-4.25 (m, 2H), 2.85-2.60 (m, 4H), 2.40 (s, 3H).

MS (M+1) 405/407.

The following compound is prepared by the previous method (8):

| Prep# | Product Name | Physical Data |
|---|---|---|
| 9 | 7-Bromo-4-(2-pyridin-2-yl)-5,6-dihydro-4H-pyrrolo[1,2-b]pyrazol-3-yl]quinoline | mp 214-216° C.; MS ES$^+$ m/e 391 (M + 1), 393 (M + 3) |

Scheme 2

Synthesis of 2-Pyridin-2-yl-5,6-dihydro-4H-pyrrolo[1,2-b]pyrazole-3-boronic acid Scheme 2 depicts an alternative route for the preparation of the dihydropyrrolopyrazole central structure, beginning with step E. In step E, ethyl picolinylacetate (Formula 8) is reacted with 1-aminopyrrolidione hydrochloride (Formula 9) to yield an imine. The picolinate may be substituted at the 6-position of the nitrogen heterocycle. Typically, the reaction is conducted in a suitable solvent such as ethanol, N-methylpyrrolidinone or pyridine, with pyridine being the preferred solvent. The reaction is carried out at temperatures of about 60° C. to ambient for 4-24 hours. The products can be isolated and purified by techniques described above. Step F, as described above, depicts the cyclization of a compound of Formula 10 to give an optionally substituted compound of Formula 11. Typically, the appropriate compound of Formula 10 is reacted with a suitable base that can form the anion of the hydrazone, cesium carbonate being the preferred base in a suitable solvent, preferably N,N-dimethylformamide, at 100° C. The ethyl ester of the pendant carboxylate on the resultant dihydropyrrolopyrazole Formula 11 is removed as in Step G by ethanolic base hydrolysis with gentle heating under standard conditions. Following isolation of the carboxylic acid (Formula 12), the acid may be converted to a halide of Formula 13, preferably a bromide, as in Step H with N-halosuccinimide in the presence of a weak base such as sodium bicarbonate in a suitable solvent such as DMF, at room temperature. The use of N-bromosuccinimide as the halogenating reagent is shown. Step I depicts the transformation of the halide of Formula 13 to a boronic acid of Formula 14, by treatment of the halide with a strong base such as n-butyllithium at −78° C., followed by quenching of the intermediate carbanions with a source of boron, such as triisopropyl borate. The boronic acid may be liberated from the boronic ester upon workup with aqueous ammonium chloride. This transformation is well known and appreciated in the art (Larock, R. C., *Comprehensive Organic Transformations*, $2^{nd}$ Ed., copyright 1999, John Wiley & Sons, pp 741-742). The boronic acid or boronic ester of Formula 14 may subsequently be used as a leaving group in combination with a substituted aryl- or heteroarylhalide in the presence of a suitable palladium catalyst, preferably tetrakis(triphenylphosphine)palladium (0), and a suitable base such as potassium carbonate to further give compounds of Formula (I) (Suzuki reaction see: Miyaura, N.; Yanagi, T.; Suzuki, A. The Palladium-Catalyzed Cross Coupling Reaction of Phenylboronic Acid with Haloarenes in the Presence of Bases. *Synth. Commun.,* 1981, 513-518).

Scheme 2

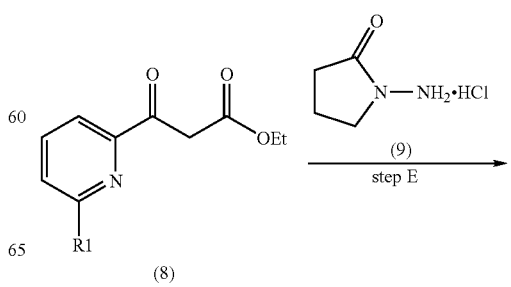

(8)

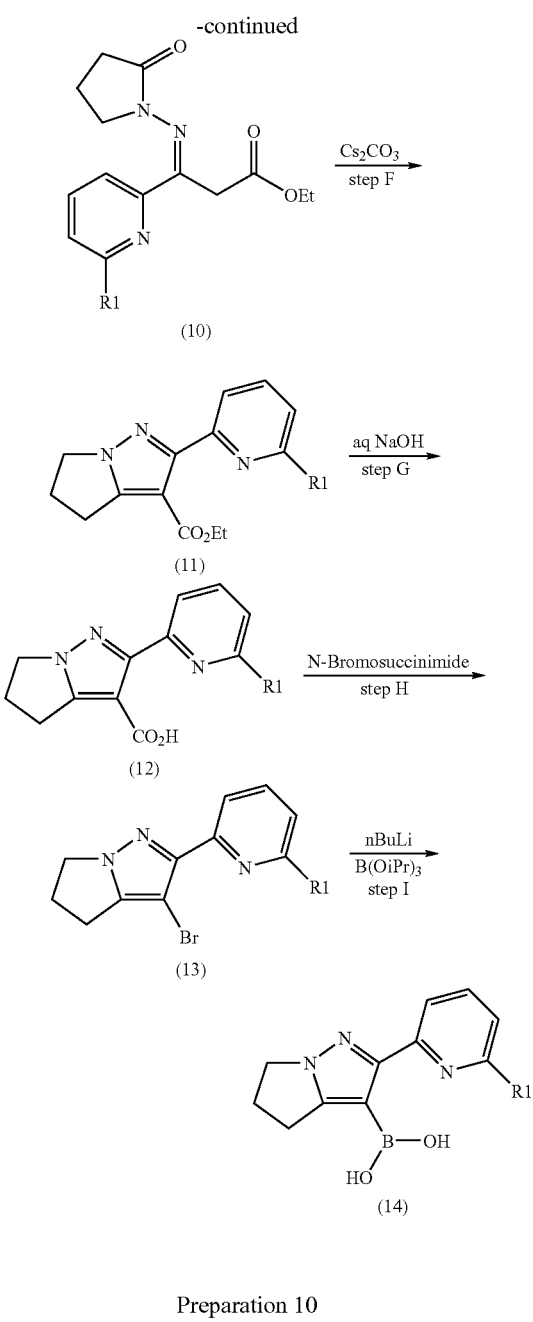

Ethyl picolinoylacetate (4.7 g, 24.3 mmol) and the product of Preparation 1 (5.0 g, 36.5 mmol) are mixed in 10 mL of pyridine. The reaction mixture is stirred overnight at RT and then evaporated to a solid mass. The crude mixture is purified by MPLC on silica gel (40% EtOAc/Hexanes) to give the title compound, 6.63 g (95%), as a liquid. MS ES⁺ m/e 276.1 (M+1).

The following compound is prepared by the previous method utilizing Ethyl 6-Methylpicolinoylacetate (Ref 1)(10):

| Prep# | Product Name | Physical Data |
|---|---|---|
| 11 | 3-(6-Methylpyridin-2-yl)-3-(2-oxo-pyrrolidin-1-ylimino)-propionic Acid Ethyl Ester | MS ES⁺ m/e 290.3 (M + 1) |

Preparation 12

2-Pyridin-2-yl-5,6-dihydro-4H-pyrrolo[1,2-b]pyrazole-3-carboxylic Acid Ethyl Ester 200 mL of DMF is added to the product of Preparation 10 (8.2 g, 30 mmol) and Cs₂CO₃ (19.5 g, 60 mmol). After stirring for 30 min at RT under nitrogen, the reaction mixture is heated at 100° C. for 8 h, cooled to RT, diluted with EtOAc (300 mL) and extracted with saturated NaHCO₃. The organic phase is separated and the aqueous phase is extracted 2 times with 50 mL portions of EtOAc. The combined organic extracts are washed with saturated brine, dried (Na₂SO₄), filtered, and evaporated to yield the title compound, 6.64 g (86%), as cream-colored solid. MS ES⁺ m/e 258.0 (M+1).

Preparation 10

3-(2-Oxo-pyrrolidin-1-yl-imino)-3-pyridin-2-yl-propionic Acid Ethyl Ester

The following compound is prepared by the previous method (12):

| Prep# | Product Name | Physical Data |
|---|---|---|
| 13 | (6-Methyl-pyridin-2-yl)-5,6-dihydro-4H-pyrrolo[1,2-b]pyrazole-3-carboxylic Acid Ethyl Ester | MS ES⁺ m/e 272.0 (M + 1) |

Preparation 14

2-Pyridin-2-yl-5,6-dihydro-4H-pyrrolo[1,2-b]pyrazole-3-carboxylic Acid

The product from Preparation 12 (6.54 g, 25.4 mmol) is dissolved in EtOH (10 mL) and NaOH (2 N, 20 mL) and heated to reflux for 3 h. The reaction is then cooled to RT and concentrated to remove the EtOH. The pH of the aqueous solution is adjusted to 6-7 by the addition of 1N HCl solution. The precipitated solid is filtered, washed with $Et_2O$ and dried to yield the title compound, 4.9 g (85%), as a white solid. MS $ES^+$ m/e 230.0 (M+1).

The following compound is prepared by the previous method (14):

| Prep# | Product Name | Physical Data |
|---|---|---|
| 15 | 2-(6-Methyl-pyridin-2-yl)-5,6-dihydro-4H-pyrrolo[1,2-b]pyrazole-3-carboxylic Acid | MS $ES^+$ m/e 244.0 (M + 1) |

Preparation 16

3-Bromo-2-pyridin-2-yl-5,6-dihydro-4H-pyrrolo[1,2-b]pyrazole

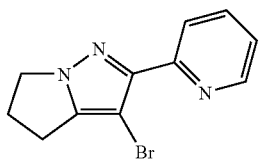

The product from Preparation 14 (2.0 g, 8.7 mmol), $NaHCO_3$ (3.3 g, 38.4 mmol) and N-bromosuccinimide (1.7 g, 9.6 mmol) are dissolved in 50 mL of DMF and are stirred at room temperature for 2 h. The crude mixture is diluted with 50 mL of water and 100 mL of EtOAc. The EtOAc layer is separated, extracted with saturated brine, dried ($Na_2SO_4$), filtered, and evaporated to a solid mass. The crude product is purified by MPLC on silica gel (50% EtOAc/Hexanes) to yield the title compound, 1.62 g (70%), as a cream-colored solid. MS $ES^+$ m/e 265.9 (M+1).

The following compound is prepared by the previous method (16):

| Prep# | Product Name | Physical Data |
|---|---|---|
| 17 | 3-Bromo-2-(6-methyl-pyridin-2-yl)-5,6-dihydro-4H-pyrrolo[1,2-b]pyrazole | MS $ES^+$ m/e 279.0 (M + 1) |

Preparation 18

2-Pyridin-2-yl-5,6-dihydro-4H-pyrrolo[1,2-b]pyrazole-3-boronic acid

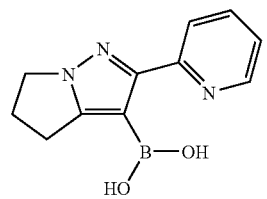

The product from Preparation 16 (0.8 g, 3 mmol) is dissolved in 10 mL of THF at −78° C. n-BuLi (4.7 mL, 7.6 mmol) in hexanes is added dropwise to the reaction mixture while maintaining the temperature between −65 and −70° C. After the addition is complete, the reaction mixture is stirred at −78° C. for 10 min, and $B(OiPr)_3$ (3.5 mL, 15 mmol) is added dropwise while maintaining the temperature between −65 and −70° C. The mixture is allowed to warm to RT and stirred for an additional 3 h. 10 mL of saturated $NH_4Cl$ is added and the reaction mixture stirred for 2 h. The organic phase is separated and the aqueous phase is extracted 3 times with 30 mL portions of $CHCl_3$. The combined organic extracts are washed with saturated brine, dried ($Na_2SO_4$), filtered, and evaporated to a solid mass. The crude solid is purified by MPLC on silica gel using a linear gradient of 50% EtOAc/Hexanes to 80% EtOAc/Hexanes over 50 min. The chromatographed product is crystallized from $Et_2O$/Hexanes to yield the title compound, 0.528 g (77%), as white solid. MS ES+ m/e 229.9 (M+1).

The following compound is prepared by the previous method (18):

| Prep# | Product Name | Physical Data |
|---|---|---|
| 19 | 2-(6-Methyl-pyridin-2-yl)-5,6-dihydro-4H-pyrrolo[1,2-b]pyrazole-3-boronic acid | MS $ES^+$ m/e 244.3 (M + 1) |

Scheme 3

Alternate synthesis of 5,6-dihydro-4H-pyrrolo[1,2-b]pyrazole derivatives

Scheme 3 depicts the preparation of the compounds of Formula I through a route which differs from Scheme 1. In Scheme 3, a 4-haloheterocycle of Formula 17a, 17b is prepared in two steps from a precursor 4-hydroxyheterocycle by conversion first to a triflate as in Step J. The triflate (Formula 16) is prepared by reaction of the 4-hydroxyquinoline with trifluoromethanesulfonic anhydride in the presence of a polar, basic solvent such as pyridine at 0° C. Treatment of the triflate with a halide salt such as potassium iodide (Step K) or lithium bromide (Step L) provides the 4-iodo (Formula 17a) or 4-bromoheterocycle (Formula 17b), respectively. These halogenations require a polar solvent such as dimethylformamide or acetonitrile and temperatures ranging from RT to 100° C. The haloheterocycle can be coupled to a pyrrolopyrazole boronic acid of Formula 14 (Step M) in the presence of a palladium catalyst, preferably tris(dibenzylidineacetone)dipalladium (0) (Pd$_2$(dba)$_3$), with a suitable base such as potassium carbonate. An additional ligand for the palladium, such as triphenylphosphine, may be used. All of the reagents are combined in a suitable solvent, typically dioxane, and stirred at reflux temperature. All products (Formula 18) can be isolated and purified by silica gel chromatography (MPLC), reverse phase HPLC, or trituration of solid as described above.

R' and R": alkyl, aryl, heterocycle, or halogen or together form an aromatic or heterocyclic ring Preparation 20

Trifluoromethanesulfonic Acid 7-bromo-quinolin-4-yl Ester

7-Bromo-quinolin-4-ol (Ref. 2)(0.8 g, 3.6 mmol) is dissolved in 10 mL of pyridine at 0° C. under nitrogen. Trifluoromethanesulfonic anhydride (1.3 mL, 4.3 mmol) is added dropwise to the reaction mixture while maintaining the temperature at 0° C. After the addition is complete, the reaction mixture is stirred at 0° C. for 2 h, warmed to room temperature and evaporated to a slurry. The crude mixture is diluted with 20 mL of water and 50 mL of EtOAc. The EtOAc layer is separated, extracted with saturated brine, dried over anhydrous Na$_2$SO$_4$, filtered, and evaporated to a solid mass. The crude product is purified by MPLC on silica gel (30% EtOAc/Hexanes) to yield the title compound, 0.82 g (63%), as white solid. MS ES$^+$ m/e 355.9, 357.9 (M+1).

Preparation 21

7-Bromo-4-iodoquinoline

The product of Preparation 20 (0.2 g, 0.56 mmol) and KI (0.93 g, 5.6 mmol) are dissolved in 10 mL of DMF and the mixture is heated at 100° C. for 8 h under nitrogen, then cooled to room temperature, diluted with EtOAc (30 mL) and extracted with saturated NaHCO$_3$. The organic phase is separated and the aqueous phase is extracted 2 times with 10 mL portions of EtOAc. The combined organic extracts are washed with saturated brine, dried (Na$_2$SO$_4$), filtered, and evaporated to a solid mass. The crude product is purified by MPLC on silica gel (25% EtOAc/Hexanes) to yield the title compound, 0.08 g (44%), as white solid. MS ES+ m/e 335.9 (M+1).

Preparation 22

4,7-Dibromoquinoline

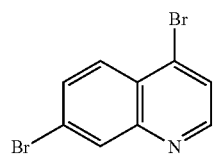

The product of Preparation 20 (3.15 g, 8.8 mmol) and LiBr (7.7 g, 88.5 mmol) are dissolved in 100 mL of $CH_3CN$ and the mixture is heated at 55° C. for 8 h under nitrogen. The reaction mixture is cooled to RT and evaporated to a slurry. The crude mixture is diluted with EtOAc (30 mL) and washed with saturated $NaHCO_3$ solution. The organic phase is separated and extracted with saturated brine, dried ($Na_2SO_4$), filtered, and evaporated to a solid mass. The crude product is purified by MPLC on silica gel (25% EtOAc/Hexanes) to yield the title compound, 1.9 g (75%), as white solid. MS ES+ m/e 287.8 (M+1).

Preparation 23

7-Bromo-4-(2-pyridin-2-yl-5,6-dihydro-4H-pyrrolo[1,2 b]pyrazol-3-yl)quinoline

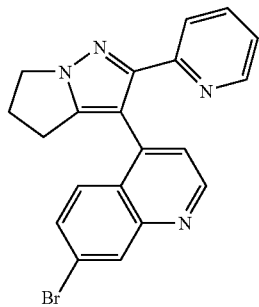

The product of Preparation 21 (0.05 g, 0.15 mmol), the product of Preparation 18 (0.034 g, 0.15 mmol) and 0.7 mL of 2M $K_2CO_3$ are mixed in 2 mL of dioxane. The mixture is degassed and flushed with nitrogen several times. Tris(dibenzylideneacetone) dipalladium (0) (0.004 g, 0.0045 mmol) and triphenylphosphine (0.002 g, 0.009 mmol) are added, and the reaction mixture degassed and flushed with nitrogen again. The mixture is heated to reflux at 115° C. for 4 h under nitrogen. The reaction mixture is cooled and diluted with water (2 mL) and EtOAc (4 mL). The organic layer is separated and extracted with saturated brine, dried over anhydrous $Na_2SO_4$, filtered, and evaporated to a solid mass. The crude product is purified by MPLC on silica gel (70% EtOAc/Hexanes) to yield the title compound, 0.045 g (77%), as white solid. MS ES+ m/e 391.1, 393.1 (M+1).

The following compound is prepared by the previous method (23):

| Prep# | Product Name | Physical Data |
|---|---|---|
| 24 | 7-Bromo-4-[2-(6-methylpyridin-2-yl)-5,6-dihydro-4H-pyrrolo[1,2-b]pyrazol-3-yl]quinoline | MS ES+ m/e 405.0, 407.0 (M + 1) |

Preparation of Final Products:

Scheme 4

Synthesis of 7-Substituted Quinoline Derivatives

Scheme 4 elaborates substitution of the C-7 position of the 7-bromoquinoline of Formula 19. A representative transformation is seen in Step N, in which a metal-nucleophile, such as trialkylstannyls, or boranes with a suitable base such as potassium carbonate, sodium alkoxides (sodium methoxide, or sodium ethoxide) or potassium alkoxides (potassium methoxide, or potassium ethoxide) can be used with a palladium catalyst, previously described, preferably tris(dibenzylidineacetone)dipalladium (0) ($Pd_2(dba)_3$). An additional ligand for the palladium, such as triphenylphosphine, may be used. The stannyl or boronic acid reagents may be aromatic with one or more substituents or variously substituted heteroaromatics. Protecting groups may be required on the O, N, or S-containing functional groups. In addition, organozinc reagents may also be employed to effect the net displacement of the halide at the C-7 position by an alkyl group. All of the reagents are combined in a suitable solvent, typically dioxane, isopropyl alcohol, tetrahydrofuran, toluene or ethylene glycol dimethyl ether, stirred at temperatures from room temperature to reflux. The coupling of arylhalides with metalloaromatics and metallo-alkyls by similar methods has been reviewed in the literature (Stanforth, S. P. *Tetrahedron*, 1998, 54, 263-303). The product of Formula 20 may require an additional synthetic step to remove a group such as t-butoxycarbonyl or trimethylsilyl, by treatment with trifluoroacetic acid or tetra-n-butylammonium fluoride, respectively. Such deprotection conditions are well known in the art. (Greene, T. W.; Wuts, P. G. M. *Protective Groups in Organic Synthesis* (3rd ed.); Wiley: New York, 1999.) All products can be isolated and purified by silica gel chromatography (MPLC), reverse phase HPLC, or trituration of solid as described above.

Scheme 4

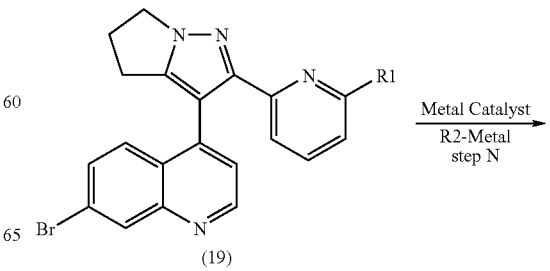

-continued

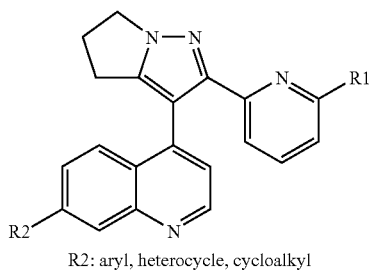

R2: aryl, heterocycle, cycloalkyl (20)

EXAMPLE 1

4-(2-Pyridin-2-yl-5,6-dihydro-4H-pyrrolo[1,2-b]pyrazol-3-yl)-7-thiophen-2-yl-quinoline Trifluoroacetic Acid

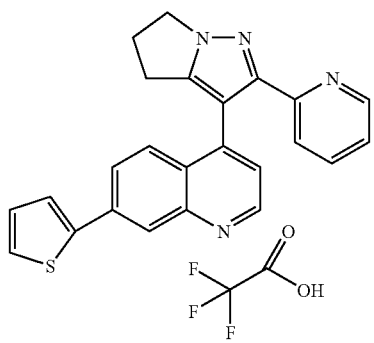

Into a 10 mL round bottom flask is placed the product of Preparation 9 (0.0782 g, 0.2 mmol), thiophene-2-boronic acid (0.0512 g, 0.4 mL), 2 mL isopropanol, and 1 mL 2M $K_2CO_3$. A reflux condenser is situated, and the mixture is evacuated and flushed with nitrogen several times. Tetrakis(triphenylphosphine)Pd(0) (0.0069 g, 0.006 mmol) is added. Evacuation and flushing with nitrogen is repeated and mixture is heated in oil bath at 80° C. for 5 h. The reaction mixture is cooled, diluted with 2 mL water and 4 mL EtOAc, and agitated. The water layer is removed, 2 mL water is added, and the extraction procedure repeated. The organic layer is eluted over 1 g silica gel cartridge with 25 mL MeOH containing one drop concentrated $NH_4OH$. The MeOH solution is evaporated under reduced pressure. The residue is dissolved in 20 mL EtOH and evaporated again. Purified product is isolated as a free base by trituration with DMSO and drying at high vacuum. The product TFA salt (53.2 mg, 43% yield) is obtained by freeze drying appropriate fractions (based on LC/MS analysis) from reverse phase HPLC using Waters Symmetry C18 column with a gradient of 10 to 70% B in A, where A is water containing 0.1% TFA and B is $CH_3CN$ containing 0.1% TFA.

MS ES+ m/e 395 (M+1 of free base)

This method of Example 1 is used to prepare the following compound:

| Example # | Product Name | Physical Data |
|---|---|---|
| 2 | 7-(4-methylthiophen-2-yl)-4-(2-pyridin-2-yl-5,6-dihydro-4H-pyrrolo[1,2-b]pyrazol-3-yl)quinoline Trifluoroacetic Acid | MS ES+ m/e 409 (M + 1) |

EXAMPLE 3

N-{4-[4-Pyridin-2-yl-5,6-dihydro-4H-pyrrolo[1,2-b]pyrazol-3-yl)-quinolin-7-yl]phenyl}acetamide Trifluoroacetic Acid

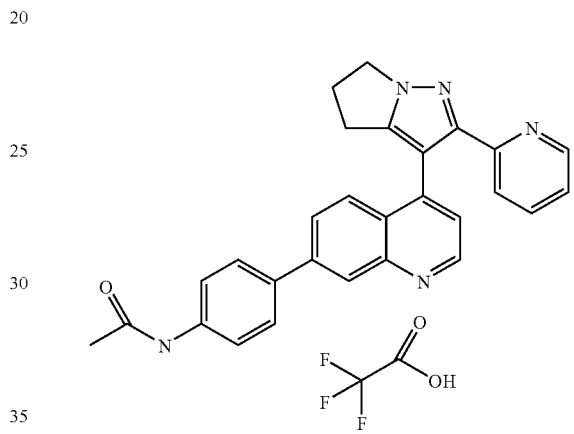

Into a 10 mL round bottom is placed the product of Preparation 9 (0.0782 g, 0.2 mmol), N-[4-(4,4,5,5-tetramethyl-[1,3,2]dioxaborolan-2-yl)phenyl]acetamide (0.104 g, 0.4 mmol), 2 mL dioxane, and 1 mL 2M $K_2CO_3$. The mixture is heated in oil bath at 110° C. for few minutes to dissolve organic reagents. A reflux condenser is positioned and the mixture is evacuated and purged with nitrogen several times. To the mixture is added $Pd_2(dba)_3$ (0.007 g, 0.006 mmol) and triphenylphosphine (0.007 g, 0.024 mmol) and the evacuating and purging with nitrogen repeated. The reaction mixture is heated in an oil bath at 110° C. for 3 h. The mixture is cooled, extracted, and purified as in Example 1 to give the titled product (0.095 g, 70% yield).

MS ES+ 446 (M+1)

Using the methods of the previous Examples 1 and 3, changing only the workup procedure to isolate the crude product from the aqueous layer by precipitation with dilute HCl when there is an acidic functionality situated on the aryl ring of the boronic acid, the following compounds are prepared:

| Ex. # | Product Name | Physical Data |
|---|---|---|
| 4 | 7-Phenyl-4-(2-pyridin-2-yl-5,6-dihydro-4H-pyrrolo[1,2-b]pyrazol-3-yl)quinoline Trifluoroacetic Acid | MS ES+ 389 (M + 1) |
| 5 | 2-[4-(2-pyridin-2-yl-5,6-dihydro-4H-pyrrolo[pyrazol-3-yl)quinolin-7-yl]phenol Trifluoroacetic Acid | MS ES+ 405 (M + 1) |

-continued

| Ex. # | Product Name | Physical Data |
|---|---|---|
| 6 | 3-[4-(2-Pyridin-2-yl-5,6-dihydro-4H-pyrrolo[1,2-b]pyrazol-3-yl)quinolin-7-yl]phenol Trifluoroacetic Acid | MS ES+ 405 (M + 1) |
| 7 | 4-[4-(2-Pyridin-2-yl-5,6-dihydro-4H-pyrrolo[1,2-b]pyrazol-3-yl)quinolin-7-yl]phenol Trifluoroacetic Acid | MS ES+ 405 (M + 1) |
| 8 | 2-[4-(2-Pyridin-2-yl-5,6-dihydro-4H-pyrrolo[1,2-b]pyrazol-3-yl)quinolin-7-yl]phenylamine Ditrifluoroacetic Acid | MS ES+ 404 (M + 1) |
| 9 | 3-[4-(2-Pyridin-2-yl-5,6-dihydro-4H-pyrrolo[pyrazol-3-yl)quinolin-7-yl]phenylamine Ditrifluoroacetic Acid | MS ES+ 404 (M + 1) |
| 10 | 4-[4-(2-Pyridin-2-yl-5,6-dihydro-4H-pyrrolo[1,2-b]pyrazol-3-yl)phenylamine Ditrifluoroacetic Acid | MS ES+ 404 (M + 1) |
| 11 | 7-(3-Chlorophenyl)-4-(2-Pyridin-2-yl-5,6-dihydro-4H-pyrrolo[1,2-b]pyrazol-3-yl)quinoline Trifluoroacetic Acid | MS ES+ 423 (M + 1) |
| 12 | 7-(4-Chlorophenyl)-4-(2-Pyridin-2-yl-5,6-dihydro-4H-pyrrolo[1,2-b]pyrazol-3-yl)quinoline Trifluoroacetic Acid | MS ES+ 423 (M + 1) |
| 13 | 7-(3-Nitrophenyl)-4-(2-pyridin-2-yl-5,6-dihydro-4H-pyrrolo[1,2-b]pyrazol-3-yl)quinoline Trifluoroacetic Acid | MS ES+ 434 (M + 1) |
| 14 | 7-(4-Nitrophenyl)-4-(2-pyridin-2-yl-5,6-dihydro-4H-pyrrolo[1,2-b]pyrazol-3-yl)quinoline Trifluoroacetic Acid | MS ES+ 434 (M + 1) |
| 15 | N-{3-[4-(2-Pyridin-2-yl-5,6-dihydro-4H-pyrrolo[1,2-b]pyrazol-3-yl)-quinolin-7-yl]-phenyl}methanesulfomamide Trifluoroacetic Acid | MS ES+ 482 (M + 1) |
| 16 | N-{4-[4-(2-Pyridin-2-yl-5,6-dihydro-4H-pyrrolo[1,2-b]pyrazol-3-yl)quinolin-7-yl]phenyl}methanesulfonamide Trifluoroacetic Acid | MS ES+ 482 (M + 1) |
| 17 | 7-(2-Ethoxyphenyl)-4-(2-pyridin-2-yl-5,6-dihydro-4H-pyrrolo[1,2-b]pyrazol-3-yl)quinoline Trifluoroacetic Acid | MS ES+ 433 (M + 1) |
| 18 | 7-(3-Ethoxyphenyl)-4-(2-pyridin-2-yl-5,6-dihydro-4H-pyrrolo[1,2-b]pyrazol-3-yl)quinoline Trifluoroacetic Acid | MS ES+ 433 (M + 1) |
| 19 | 7-(4-Ethoxyphenyl)-4-(2-pyridin-2-yl-5,6-dihydro-4H-pyrrolo[1,2-b]pyrazol-3-yl)quinoline Trifluoroacetic Acid | MS ES+ 433 (M + 1) |
| 20 | 7-(4-Methoxyphenyl)-4-(2-pyridin-2-yl-5,6-dihydro-4H-pyrrolo[1,2-b]pyrazol-3-yl)quinoline Trifluoroacetic Acid | MS ES+ 419 (M + 1) |
| 21 | 7-(4-Fluoro-3-methylphenyl)-4-(2-pyridin-2-yl-5,5-dihydro-4H-pyrrolo[1,2-b]pyrazol-3-yl)quinoline Trifluoroacetic Acid | MS ES+ 421 (M + 1) |
| 22 | 7-(4-Fluoro-2-methylphenyl)-4-(2-pyridin-2-yl-5,6-dihydro-4H-pyrrolo[1,2-b]pyrazol-3-yl)quinoline Trifluoroacetic Acid | MS ES+ 421 (M + 1) |
| 23 | 7-(4-Bromophenyl)-4-(2-pyridin-2-yl-5,6-dihydro-4H-pyrrolo[1,2-b]pyrazol-3-yl)quinoline Trifluoroacetic Acid | MS ES+ 468 (M + 1) |
| 24 | 7-(4-Ethylsulfanylphenyl)-4-(2-pyridin-2-yl-5,6-dihydro-4H-pyrrolo[1,2-b]pyrazol-3-yl)quinoline Trifluoroacetic Acid | MS ES+ 449 (M + 1) |
| 25 | 7-(4-Methylsulfanylphenyl)-4-(2-pyridin-2-yl-5,6-dihydro-4H-pyrrolo[1,2-b]pyrazol-3-yl)quinoline Trifluoroacetic Acid | MS ES+ 435 (M + 1) |
| 26 | 4-[4-(2-Pyridin-2-yl-5,6-dihydro-4H-pyrrolo[1,2-b]pyrazol-3-yl)quinolin-7-yl]benzonitrile Trifluroacetic Acid | MS ES+ 414 (M + 1) |
| 27 | 7-(1H-Indol-5-yl)-4-(2-pyridin-2-yl-5,6-dihydro-4H-pyrrolo[1,2-b]pyrazol-3-yl)quinoline Ditrifluoroacetic Acid | MS ES+ 428 (M + 1) |
| 28 | 1-{4-[4-(2-Pyridin-2-yl-5,6-dihydro-4H-pyrrolo[1,2-b]pyrazol-3-yl)quinolin-7-yl]phenyl}ethanone Trifluoroacetic Acid | MS ES+ 431 (M + 1) |
| 29 | 2-[4-(2-Pyridin-2-yl-5,6-dihydro-4H-pyrrolo[1,2-b]pyrazol-3-yl)quinolin-7-yl]phenyl}benzamide Trifluoroacetic Acid | MS ES+ 432 (M + 1) |
| 30 | 3-{4-[4-(2-Pyridin-2-yl-5,6-dihydro-4H-pyrrolo[1,2-b]pyrazol-3-yl)quinolin-7-yl]phenyl}propionic Acid Trifluoroacetic Acid | MS ES+ 461 (M + 1) |
| 31 | 7-(3,5-Dichlorophenyl)-4-(2-Pyridin-2-yl-5,6-dihydro-4H-pyrrolo[1,2-b]pyrazol-3-yl)quinoline Trifluoroacetic Acid | MS ES+ 433 (M + 1) |
| 32 | 7-(4-Methoxy-3-methylphenyl)-4-(2-Pyridin-2-yl-5,6-dihydro-4H-pyrrolo[1,2-b]pyrazol-3-yl)quinoline Trifluoroacetic Acid | MS ES+ 433 (M + 1) |
| 33 | 2-Methyl-5-[4-(2-Pyridin-2-yl-5,6-dihydro-4H-pyrrolo[1,2-b]pyrazol-3-yl)quinolin-7-yl]phenylamine Ditrifluoroacetic Acid | MS ES+ 418 (M + 1) |
| 34 | 7-Pyridin-4-yl-4-(2-pyridin-2-yl-5,6-dihydro-4H-pyrrolo[1,2-b]pyrazol-3-yl)quinoline Ditrifluoroacetic Acid | MS ES+ 390 (M + 1) |
| 35 | 7-Pyridin-3-yl-4-(2-pyridin-2-yl-5,6-dihydro-4H-pyrrolo[1,2-b]pyrazol-3-yl)quinoline Ditrifluoroacetic Acid | MS ES+ 390 (M + 1) |
| 36 | 7-(2-Nitrophenyl)-4-(2-pyridin-2-yl-5,6-dihydro-4H-pyrrolo[1,2-b]pyrazol-3-yl)quinoline Trifluoroacetic Acid | MS ES+ 434 (M + 1) |
| 37 | N-{3-[4-(2-pyridin-2-yl-5,6-dihydro-4H-pyrrolo[1,2-b]pyrazol-3-yl)quinolin-7-yl]phenyl}-acetamide Trifluoroacetic Acid | MS ES+ 446 (M + 1) |
| 38 | 7-(4-Methanesulfinylphenyl)-4-(2-pyridin-2-yl-5,6-dihydro-4H-pyrrolo[1,2-b]pyrazol-3-yl)quinoline Trifluoroacetic Acid | MS ES+ 451 (M + 1) |
| 40 | 7-Benzo[1,3]dioxol-5-yl-4-(2-pyridin-2-yl-5,6-dihydro-4H-pyrrolo[1,2-b]pyrazol-3-yl)quinoline Trifluoroacetic Acid | MS ES+ 433 (M + 1) |
| 41 | 4-[4-(2-pyridin-2-yl-5,6-dihydro-4H-pyrrolo[1,2-b]pyrazol-3-yl)quinolin-7-yl]benzoic Acid Trifluoroacetic Acid | MS ES+ 433 (M + 1) |
| 42 | 7-(3,5-Bis-trifluromethylphenyl)-4-(2-pyridin-2-yl-5,6-dihydro-4H-pyrrolo[1,2-b]pyrazol-3-yl)quinoline Trifluoroacetic Acid | MS ES+ 525 (M + 1) |
| 43 | 3-[4-(2-pyridin-2-yl-5,6-dihydro-4H-pyrrolo[1,2-b]pyrazol-3-yl)quinolin-7-yl]benzoic Acid Trifluoroacetic Acid | MS ES+ 433 (M + 1) |
| 44 | 2-[4-(2-pyridin-2-yl-5,6-dihydro-4H-pyrrolo[1,2-b]pyrazol-3-yl)quinolin-7-yl]benzoic Acid Trifluoroacetic Acid | MS ES+ 433 (M + 1) |
| 45 | 7-(4-Isobutylphenyl)-4-(2-pyridin-2-yl-5,6-dihydro-4H-pyrrolo[1,2-b]pyrazol-3-yl)quinoline Trifluoroacetic Acid | MS ES+ 445 (M + 1) |
| 46 | {4-[4-(2-pyridin-2-yl-5,6-dihydro-4H-pyrrolo[1,2-b]pyrazol-3-yl)quinolin-7-yl]phenoxy}acetic Acid Trifluoroacetic Acid | MS ES+ 463 (M + 1) |
| 47 | 7-Benzo[b]thiophen-2-yl-4-(2-pyridin-2-yl-5,6-dihydro-4H-pyrrolo[1,2-b]pyrazol-3-yl)quinoline Trifluoroacetic Acid | MS ES+ 445 (M + 1) |
| 48 | 7-Benzofuran-2-yl-4-(2-pyridin-2-yl-5,6-dihydro-4H-pyrrolo[1,2-b]pyrazol-3-yl)quinoline Trifluoroacetic Acid | MS ES+ 429 (M + 1) |
| 49 | 7-(3-Nitrophenyl)-4-(2-pyridin-2-yl-5,6-dihydro-4H-pyrrolo[1,2-b]pyrazol-3-yl)quinoline Trifluoroacetic Acid | MS ES+ 320 (M + 1) |
| 50 | 4-(2-pyridin-2-yl-5,6-dihydro-4H-pyrrolo[1,2-b]pyrazol-3-yl)-7-thiophen-3-yl-quinoline Trifluoroacetic Acid | MS ES+ 395 (M + 1) |
| 51 | 7-Furan-4-yl-4-(2-pyridin-2-yl-5,6-dihydro-4H-pyrrolo[1,2-b]pyrazol-3-yl)quinoline Trifluoroacetic Acid | MS ES+ 379 (M + 1) |
| 52 | 7-(4-Methyl-3-nitro-phenyl)-4-(2-pyridin-2-yl-5,6-dihydro-4H-pyrrolo[1,2-b]pyrazol-3-yl)-quinoline Trifluoroacetic Acid | MS ES+ 462 (M + 1) |
| 53 | 7-(4-Cyclohexyl-phenyl)-4-(2-pyridin-2-yl-5,6-dihydro-4H-pyrrolo[1,2-b]pyrazol-3-yl)-quinoline Trifluoroacetic Acid | MS ES+ 471 (M + 1) |

-continued

| Ex. # | Product Name | Physical Data |
|---|---|---|
| 54 | 7-(4-Benzo[b]thiophen-3-yl-phenyl)-4-(2-pyridin-2-yl-5,6-dihydro-4H-pyrrolo[1,2-b]pyrazol-3-yl)-quinoline Trifluoroacetic Acid | MS ES+ 445 (M + 1) |

EXAMPLE 55

7-(3,4-Dichlorophenyl)-4-(2-pyridin-2-yl-5,6-dihydro-4H-pyrrolo[1,2-b]pyrazol-3-yl)-quinoline

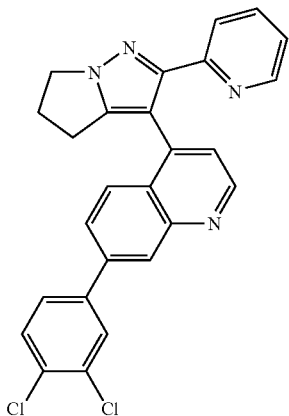

The product of Preparation 9 (0.035 g, 0.089 mmol), 3,4-dichlorophenylboronic acid (0.02 g, 0.11 mmol) and 0.3 mL 2M K$_2$CO$_3$ are mixed in 2 mL of dioxane. The mixture is degassed and flushed with nitrogen several times. Tris(dibenzylideneacetone) dipalladium (0) (0.003 g, 0.003 mmol) and triphenylphosphine (0.002 g, 0.005 mmol) are added, degassed and flushed with nitrogen. The mixture is heated to reflux at 115° C. for 4 h under nitrogen. The reaction mixture is cooled, diluted with water (2 mL) and EtOAc (4 mL). The organic layer is separated and extracted with saturated brine, dried (Na$_2$SO$_4$), filtered, evaporated to a solid mass. The crude is purified by MPLC on silica gel (70% EtOAc/Hexanes, 1% MeOH) to yield the title compound, 0.034 g (83%), as a cream-colored solid. MS ES+ m/e 457.1 (M+1).

Using the method of Example 55, changing only the procedure to isolate the crude zwitterionic product from the aqueous layer by precipitation with dilute HCl when there is an acidic functionality situated on the aryl ring of the boronic acid, the following compounds are made.

| Example # | Product Name | Physical Data |
|---|---|---|
| 56 | 4-[4-(2-Pyridin-2-yl-5,6-dihydro-4H-pyrrolo[1,2-b]pyrazol-3-yl)-quinolin-7-yl]-benzoic acid | MS ES+ m/e 433.1 (M + 1) |
| 57 | 4-{4-[2-(6-Methyl-pyridin-2-yl)-5,6-dihydro-4H-pyrrolo[1,2-b]pyrazol-3-yl]-quinolin-7-yl}-benzoic acid | MS ES+ m/e 447.1 (M + 1) |
| 58 | 3-(4-{4-[2-(6-Methyl-pyridin-2-yl)-5,6-dihydro-4H-pyrrolo[1,2-b]pyrazol-3-yl]-quinolin-7-yl}-phenyl)-propionic acid | MS ES+ m/e 475.1 (M + 1) |

EXAMPLE 59

7-(4-Fluoro-phenyl)-4-[2-(6-methyl-pyridin-2-yl)-5,6-dihydro-4H-pyrrolo[1,2-b]pyrazol-3-yl]-quinoline

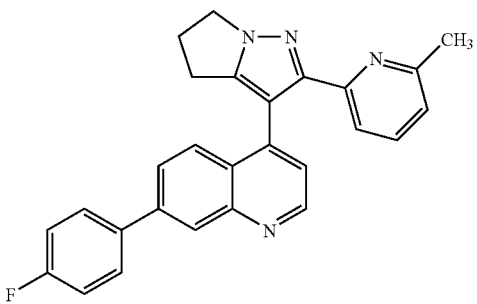

The product of Preparation 8 (0.080 g, 0.20 mmol) and 4-fluorophenylboronic acid (0.053 g, 0.40 mmol) are dissolved in DME/2M K$_2$CO$_3$ (1:1, 2.0 mL) for 20 min. Pd$_2$(dba)$_3$ (0.006 g, 0.006 mmol) and triphenylphosphine (0.006 g, 0.024 mmol) are added, and nitrogen is bubbled through for another 10 min. The mixture is heated to 80° C. for 48 h. The solvent is evaporated and the residue chromatographed on silica gel (eluting with 2% MeOH in CH$_2$Cl$_2$) to give the title compound, 0.070 g, 81%, as a yellow solid.

$^1$H NMR (CDCl$_3$) δ 8.88 (d, 1H, J=4.4 Hz), 8.29 (d, 1H, J=2.0 Hz), 7.83 (d, 1H, 8.8 Hz), 7.72-7.67 (m, 2H), 7.57 (dd, 1H, J=2.0, 8.8 Hz), 7.30-7.26 (m, 2H), 7.20-7.15 (m, 2H), 6.99 (d, 1H, J=7.8 Hz), 6.91 (d, 1H, J=7.8 Hz), 4.37 (t, 2H, J=7.2 Hz), 2.88 (t, 2H, J=7.2 Hz), 2.71 (q, 2H, J=7.2 Hz), 2.34 (s, 3H). MS (M+1) 421.

Using the method of the previous Example 59, the following compounds are prepared. In some cases the crude product was further purified by a preparative HPLC (Waters Symmetry Prep™ C18, 7 um, WAT066245, 19×300 mm column, eluted with a gradient solution system of 90:10 (0.2% TFA in H$_2$O)/(0.2% TFA in CH$_3$CN) to 10:90 (0.2% TFA in H$_2$O)/(0.2% TFA in CH$_3$CN)).

| Example # | Product Name | Physical data |
|---|---|---|
| 60 | 7-(4-Methoxy-phenyl)-4-[2-(6-methyl-pyridin-2-yl)-5,6-dihydro-4H-pyrrolo[1,2-b]pyrazol-3-yl]-quinoline | MS (M + 1) 433. |
| 61 | 7-Phenyl-4-[2-(6-methyl-pyridin-2-yl)-5,6-dihydro-4H-pyrrolo[1,2-b]pyrazol-3-yl]-quinoline Trifluoroacetic Acid | MS (M + 1) 403. |
| 62 | 4-[2-(6-Methyl-pyridin-2-yl)-5,6-dihydro-4H-pyrrolo[1,2-b]pyrazol-3-yl]-7-thiophen-2-yl-quinoline Trifluoroacetic Acid | MS (M + 1) 409. |
| 63 | 4-[2-(6-Methyl-pyridin-2-yl)-5,6-dihydro-4H-pyrrolo[1,2-b]pyrazol-3-yl]-7-(3-nitro-phenyl)quinoline | MS (M + 1) 448. |
| 64 | 7-(4-Chloro-phenyl)-4-[2-(6-methyl-pyridin-2-yl)-5,6-dihydro-4H-pyrrolo[1,2-b]pyrazol-3-yl]-quinoline | MS (M + 1) 437. |

EXAMPLE 65

7-Furan-2-yl-4-(2-Pyridin-2-yl-5,6-dihydro-4H-pyrrolo[1,2-b]pyrazol-3-yl)quinoline Trifluoroacetic Acid

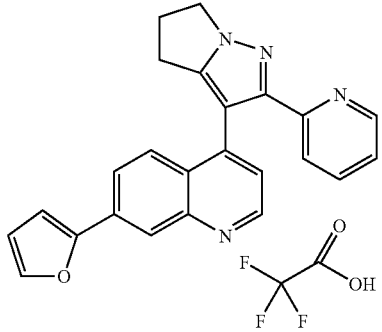

The product of Preparation 9 (0.782 g, 0.2 mmol) is placed into a 10 mL roundbottom flask and toluene (2 mL) is added. A condenser is positioned, and the mixture is evacuated and purged with nitrogen several times. To the mixture is added tribut-1-furan-2-yl-stannane (0.143 g, 0.4 mmol). The mixture evacuated and purged with nitrogen several times and then refluxed 3.5 h in an oil bath. The reaction mixture is cooled and diluted with EtOAc (3 mL) and eluted over a 1 g silica gel cartridge, ishing with MeOH (20 mL). The solvent is removed under vacuum. Purified product (63 mg, 64%) is obtained by freeze drying appropriate fractions (based on MS analysis) from reverse phase HPLC using Waters Symmetry C18 column with a gradient of 10 to 70% B in A, where A is water containing 0.1% TFA and B is $CH_3CN$ containing 0.1% TFA.

MS ES+ 379 (M+1)

Using the method of Example 65, the following compounds are prepared:

| Example # | Product Name | Physical Data |
|---|---|---|
| 66 | 4-(2-Pyridin-2-yl-5,6-dihydro-4H-pyrrolo[1,2-b]pyrazol-3-yl)-7-thiazol-2-yl-quinoline Trifluoroacetic Acid | MS ES+ 396 (M + 1) |
| 67 | 7-Pyrazin-2-yl-4-(2-Pyridin-2-yl-5,6-dihydro-4H-pyrrolo[1,2-b]pyrazol-3-yl)quinoline Ditrifluoroacetic Acid | MS ES+ 391 (M + 1) |
| 68 | 7-Pyridin-2-yl-4-(2-Pyridin-2-yl-5,6-dihydro-4H-pyrrolo[1,2-b]pyrazol-3-yl)quinoline Ditrifluoroacetic Acid | MS ES+ 390 (M + 1) |

EXAMPLE 69

4-(2-pyridin-2-yl-5,6-dihydro-4H-pyrrolo[1,2-b]pyrazol-3-yl)-7-(1H-pyrrol-2-yl)quinoline Ditrifluoroacetic Acid

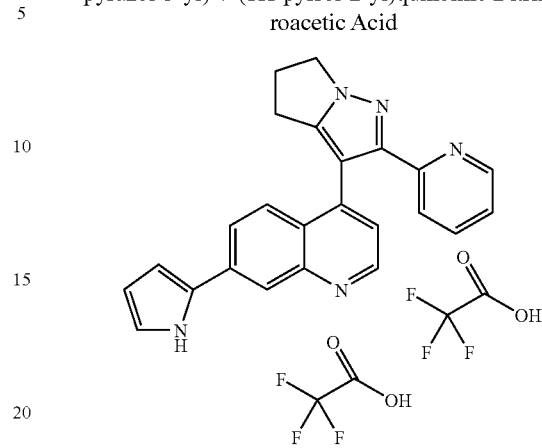

The cross coupling of 1-(t-butoxycarbonyl)pyrrole-2-boronic acid (0.168 g, 0.8 mmol) with the product of Preparation 9 (0.156 g, 0.4 mmol) is done as in Example 3. The crude product is then dissolved in 2 mL $CH_2Cl_2$ and treated with 2 mL of TFA for 16 h. The mixture is evaporated under reduced pressure, and purified product (72.2 mg, 37%) is obtained from reverse phase chromatography as described in Example 65.

MS ES+ 378 (M+1 for free base)

Using the method of Example 69, involving t-boc-protected heterocycles, the following compound is prepared:

| Example # | Product Name | Physical Chemistry |
|---|---|---|
| 70 | 7-(1H-Indol-2-yl)-4-(2-pyridin-2-yl-5,6-dihydro-4H-pyrrolo[1,2-b]pyrazol-3-yl)quinoline Ditrifluoroacetic Acid | MS ES+ 428 (M + 1) |

EXAMPLE 71

4-(2-pyridin-2-yl-5,6-dihydro-4H-pyrrolo[1,2-b]pyrazol-3-yl)-7-(1H-pyrrol-3-yl)quinoline Ditrifluoroacetic Acid

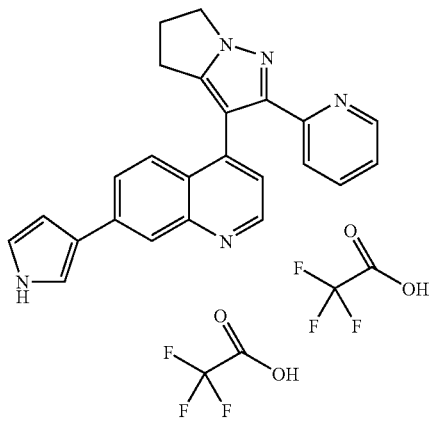

The cross coupling of 1-(triisopropylsilyl)pyrrole-3-boronic acid (0.214 g, 0.8 mmol) with the product of Preparation 9 (0.156 g, 0.4 mmol) is done as in Example 69. The crude product is then dissolved in 5 mL THF and treated with 2 mL of 0.5M tetrabutylammonium fluoride for 3 h. The mixture is diluted with 15 mL of EtOAc and washed with water (75 mL). The organic layer is dried (MgSO$_4$) and evaporated under reduced pressure. Purified product (78.4 mg, 40%) is obtained from reverse phase chromatography as described in Example 65.

MS ES$^+$ 378 (M+1)

EXAMPLE 72

7-Cyclohexyl-4-(2-pyridin-2-yl-5,6-dihydro-4H-pyrrolo[1,2-b]pyrazol-3-yl)quinoline Trifluoroacetic Acid

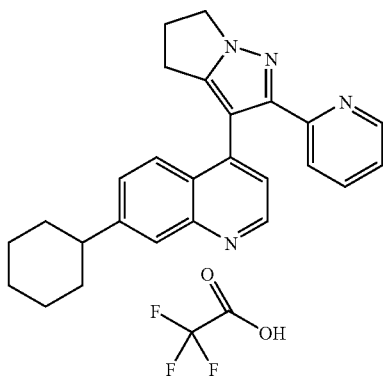

The cross coupling of cyclohexylzinc bromide (0.8 mL of 0.5M soln. in THF, 0.4 mmol)—which replaces the boronic acid—with the product of Preparation 9 (0.0782 g, 0.2 mmol) is done according to Example 3. Purified product (10 mg) is obtained from reverse phase chromatography as described in Example 65.

MS ES$^+$ 395 (M+1 for free base)

Scheme 5

Synthesis of 7-aryl/heteroaryl quinoline compounds via 7-boronate intermediate

Scheme 5 demonstrates an alternative means of attaching various aryl rings and heterocycles at the C-7 position of the 7-bromoquinoline of Formula 19. Step O illustrates that the bromide can be converted to a boronic ester of Formula 21 that can then be coupled to aryl-, heterocyclic- or alkylbromides in metal-catalyzed reactions to provide C-7 substituted quinoline compounds of Formula 20. The conversion of the heteroaryl bromide (Formula 19) is accomplished by treatment with bis(pinacolato)diboron and KOAc in a polar, high boiling solvent such as DMSO. A palladium catalyst, preferably 1,1'-bis(diphenylphosphino)ferrocene palladium (II) chloride complex with dichloromethane (PdCl$_2$(dppf)) is preferred in the reaction. The preparation of a boronate from a halide in this manner has been reported in the literature (Ishiyama, T.; Murata, M.; Miyaura, N. *J. Org. Chem.* 1995, 60, 7508-7510.).

The boronate (Formula 21) is coupled (step P) to an aryl- or heterocyclic halide with a suitable base such as potassium carbonate, sodium alkoxides (sodium methoxide, or sodium ethoxide) or potassium alkoxides (potassium methoxide, or potassium ethoxide) in combination with a palladium catalyst, as previously described, preferably tris(dibenzylidineacetone)dipalladium (0) (Pd$_2$(dba)$_3$). An additional ligand for the palladium, such as triphenylphosphine, may be used. All of the reagents are combined in a suitable solvent, typically dioxane, isopropyl alcohol, tetrahydrofuran, toluene or ethylene glycol dimethyl ether, stirred at temperatures from room temperature to reflux. The product of Formula 20 may require an additional deprotection step to remove a group such as t-butoxycarbonyl or trimethylsilyl, by treatment with trifluoroacetic acid or tetra-n-butylammonium fluoride, respectively. All products can be isolated and purified by silica gel chromatography (MPLC), reverse phase HPLC, or trituration of solid as described above.

Scheme 5

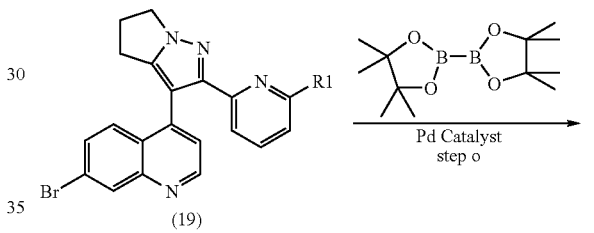

(19)

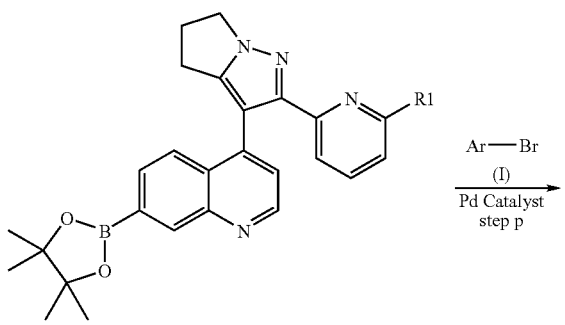

(21)

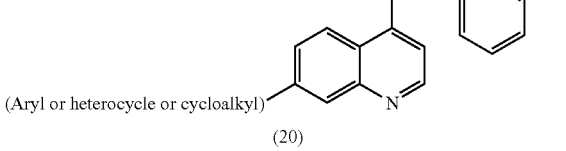

(20)

Preparation 25

4-(2-Pyridin-2-yl-5,6-dihydro-4H-pyrrolo[1,2-b]pyrazol-3-yl)-7-[4-(4,4,5,5-tetramethyl-[1,3,2]dioxaborolan-2-yl)phenyl]quinoline

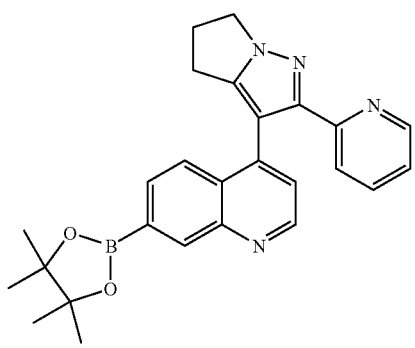

Into a 50 ml round bottom is placed the product of Preparation 9 (2.35 g, 6 mmol), bis(pinacolato) diboron (3.05 g, 12 mmol), anhydrous KOAc (2.96 g, 30 mmol), and DMSO (18 mL). The mixture is heated for a few minutes in an oil bath at 110° C. and then evacuated and purged with nitrogen several times. To the mixture is added $PdCl_2(dppf)$ (0.263 g, 0.36 mmol), and the evacuation and purging repeated. The mixture is heated under nitrogen 20 h, allowed to cool, and then poured into 100 mL of water to obtain a precipitate. The precipitate is collected, washed with water, and dried under vacuum at 60° C., to give 2.02 g (77%) of title compound, which is sufficiently pure to use in coupling reactions.

MS $ES^+$ 439 (M+1)

EXAMPLE 73

2-{4-[4-(2-Pyridin-2-yl-5,6-dihydro-4H-pyrrolo[1,2-b]pyrazol-3-yl)quinolin-yl]phenoxy}ethanol Trifluoroacetic Acid

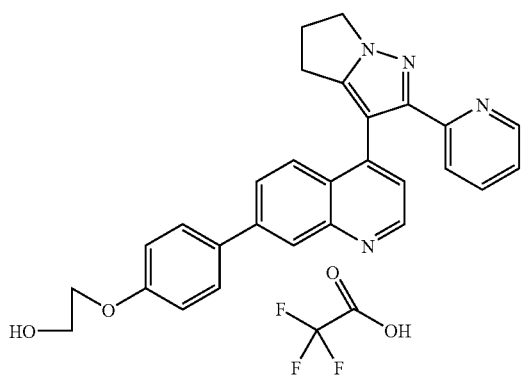

Into a 10 mL round bottom is placed the product of Preparation 25 (0.0876 g, 0.2 mmol), 2-(4-bromophenoxy)ethanol (0.087 g, 0.4 mmol), dioxane (2 mL), and 2M $K_2CO_3$ (1 mL). A condenser is situated, and the mixture is evacuated and purged with nitrogen several times. To the mixture is added $Pd_2(dba)_3$ (0.007 g, 0.006 mmol) and triphenylphosphine (0.007 g, 0.024 mmol). The mixture is evacuated and purged with nitrogen several times and then heated 5 h at gentle reflux. The mixture is cooled, diluted with EtOAc (3 mL), and the organic layer eluted over a 1 g silica gel cartridge, washing with EtOH (20 mL). The solution is evaporated under reduced pressure. Purified product (29.2 mg, 32%) is obtained by freeze drying appropriate fractions (based on MS analysis) from reverse phase HPLC using Waters Symmetry C18 column with a gradient of 10 to 70% B in A, where A is water containing 0.1% TFA and B is $CH_3CN$ containing 0.1% TFA.

MS $ES^+$ 449 (M+1)

Using the method of Example 73, changing only the workup procedure to isolate the crude product from the aqueous layer by precipitation or evaporation after treatment with dilute HCl when there is an acidic functionality situated on the aryl ring of the aryl bromide coupling partner, the following compounds are prepared:

| Example # | Product Name | Physical Data |
|---|---|---|
| 74 | {4-[4-(2-pyridin-2-yl-5,6-dihydro-4H-pyrrolo[1,2-b]pyrazol-3-yl)quinolin-7-yl]phenyl}acetic Acid Trifluoroacetic Acid | MS $ES^+$ 447 (M + 1) |
| 75 | 7-(4-Methanesulfonylphenyl)-4-(2-pyridin-2-yl-5,6-dihydro-4H-pyrrolo[1,2-b]pyrazol-3-yl)quinoline Trifluoroacetic Acid | MS $ES^+$ 467 (M + 1) |
| 76 | 2-{4-[4-(2-pyridin-2-yl-5,6-dihydro-4H-pyrrolo[1,2-b]pyrazol-3-yl)quinolin-7-yl]phenyl}ethylamine Ditrifluoroacetic Acid | MS $ES^+$ 432 (M + 1) |
| 77 | 4-(2-pyridin-2-yl-5,6-dihydro-4H-pyrrolo[1,2-b]pyrazol-3-yl)-7-p-tolylquinoline Trifluoroacetic Acid | MS $ES^+$ 403 (M + 1) |
| 78 | 2-Fluoro-4-[4-(2-pyridin-2-yl-5,6-dihydro-4H-pyrrolo[1,2-b]pyrazol-3-yl)quinolin-7-yl]phenylamine Ditrifluoroacetic Acid | MS $ES^+$ 422 (M + 1) |
| 79 | 5-[4-(2-Pyridin-2-yl-5,6-dihydro-4H-pyrrolo[1,2-b]pyrazol-3-yl)quinolin-7-yl]isophthalic Acid Trifluoroacetic Acid | MS $ES^+$ 477 (M + 1) |
| 80 | 5-[4-(2-Pyridin-2-yl-5,6-dihydro-4H-pyrrolo[1,2-b]pyrazol-3-yl)quinolin-7-yl]isophthalic Acid Dimethyl Ester Trifluoroacetic Acid | MS $ES^+$ 505 (M + 1) |
| 81 | 7-(2,2-Dioxy-2,3-dihydro-1H-2$\lambda^6$-benzo[c]thiophen-5-yl-4-(2-Pyridin-2-yl-5,6-dihydro-4H-pyrrolo[1,2-b]pyrazol-3-yl)quinoline Trifluoroacetic Acid | MS $ES^+$ 479 (M + 1) |
| 82 | 6-[4-(2-Pyridin-2-yl-5,6-dihydro-4H-pyrrolo[1,2-b]pyrazol-3-yl)quinolin-7-yl]pyridine-2-carboxylic Acid Tris-trifluoroacetic Acid | MS $ES^+$ 434 (M + 1) |
| 83 | 7-(5-Fluoropyridin-2-yl)-4-(2-Pyridin-2-yl-5,6-dihydro-4H-pyrrolo[1,2-b]pyrazol-3-yl)quinoline Ditrifluoroacetic Acid | MS $ES^+$ 408 (M + 1) |
| 84 | 7-(6-Methoxypyridazin-3-yl)-4-(2-Pyridin-2-yl-5,6-dihydro-4H-pyrrolo[1,2-b]pyrazol-3-yl)quinoline Difluoroacetic Acid | MS $ES^+$ 421 (M + 1) |
| 85 | 4-(2-Pyridin-2-yl-5,6-dihydro-4H-pyrrolo[1,2-b]pyrazol-3-yl)-7-pyrimidin-2-yl-quinoline Difluoroacetic Acid | MS $ES^+$ 391 (M + 1) |
| 86 | 4-{4-[4-(2-Pyridin-2-yl-5,6-dihydro-4H-pyrrolo[1,2-b]pyrazol-3-yl)quinolin-7-yl]phenyl}butyramide Trifluoroacetic Acid | MS $ES^+$ 474 (M + 1) |
| 87 | 7-(1H-Benzoimdazol-2-yl)-4-(2-pyridin-2-yl-5,6-dihydro-4H-pyrrolo[1,2-b]pyrazol-3-yl)quinoline Difluoroacetic Acid | MS $ES^+$ 429 (M + 1) |

53

-continued

| Example # | Product Name | Physical Data |
|---|---|---|
| 88 | 4-(2-pyridin-2-yl-5,6-dihydro-4H-pyrrolo[1,2-b]pyrazol-3-yl)-7-pyrimidin-5-yl-quinoline Difluoroacetic Acid | MS ES+ 391 (M + 1) |
| 89 | 5-[4-(2-pyridin-2-yl-5,6-dihydro-4H-pyrrolo[1,2-b]pyrazol-3-yl)-7-pyrimidin-5-yl-quinolin-7-yl]pyrimidin-2-ylamine Difluoroacetic Acid | MS ES+ 406 (M + 1) |
| 90 | 2-Chloro-4-[4-(2-pyridin-2-yl-5,6-dihydro-4H-pyrrolo[1,2-b]pyrazol-3-yl)-quinolin-7-yl]-phenylamine Ditrifluoroacetic Acid | MS ES+ 438.1 (M + 1) |
| 91 | 2-Chloro-6-fluoro-4-[4-(2-pyridin-2-yl-5,6-dihydro-4H-pyrrolo[1,2-b]pyrazol-3-yl)-quinolin-7-yl]-phenol Trifluoroacetic Acid | MS ES+ 457.3 (M + 1) |
| 92 | 5-[4-(2-Pyridin-2-yl-5,6-dihydro-4H-pyrrolo[1,2-b]pyrazol-3-yl)-quinolin-7-yl]-thiophene-2-sulfonic acid amide Trifluoroacetic Acid | MS ES+ 474.1 (M + 1) |
| 93 | 2,3-Difluoro-5-[4-(2-pyridin-2-yl-5,6-dihydro-4H-pyrrolo[1,2-b]pyrazol-3-yl)-quinolin-7-yl]-phenol Trifluoroacetic Acid | MS ES+ 441.1 (M + 1) |

EXAMPLE 94

6-[4-(2-Pyridin-2-yl-5,6-dihydro-4H-pyrrolo[1,2-b]pyrazol-3-yl)-quinolin-7-yl]-benzothiazol-2-yl amine Tris trifluoroacetic Acid

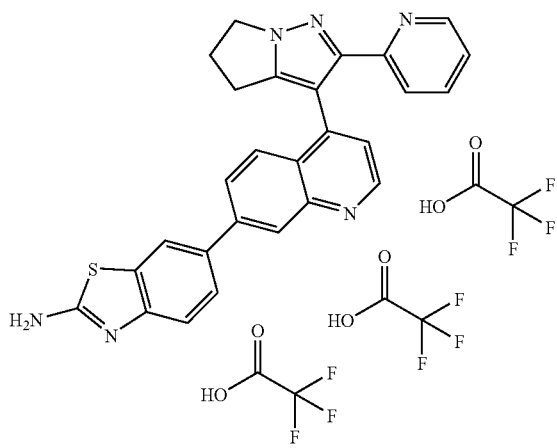

The desired product is synthesized in a manner similar to Example 73 with the exception that 0.1 mmol of bromide reagent is used and that the workup did not include the use of a silica gel column prior to preparative reversed phase chromatography to yield 21 mg (36%) of a yellow solid.

MS ES+ 461.1 (M+1 for free base)

EXAMPLE 95

4-[4-(2-Pyridin-2-yl-5,6-dihydro-4H-pyrrolo[1,2-b]pyrazol-3-yl)-quinolin-7-yl]-benzenesulfonamide

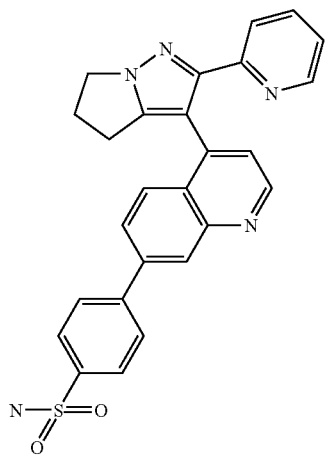

The product from Preparation 9 (0.08 g, 0.2 mmol), Bis(pinacolato)diboron (0.1 g, 0.4 mmol) and anhydrous KOAc (0.098 g, 1 mmol) are mixed in DMSO (1 mL). The mixture is degassed and flushed with nitrogen several times. To the mixture is added $PdCl_2$(dppf) (0.009 g, 0.012 mmol) and the degassing and purging are repeated. The mixture is heated under nitrogen for 8 h, allowed to cool and then 4-bromobenzenesulfonamide (0.071 g, 0.3 mmol), 0.5 mL 2M $K_2CO_3$ and 1 mL of dioxane are added. The degassing and purging are repeated. To the mixture is added palladium (II) acetate (0.003 g, 0.012 mmol) and triphenylphosphine (0.006 g, 0.024 mmol), and the reaction is degassed and flushed with nitrogen for the final time. The mixture is heated to reflux at 115° C. for 2 h under nitrogen. The reaction mixture is cooled, diluted with water (2 mL) and $CHCl_3$ (10 mL). The organic layer is separated and extracted with saturated brine, dried ($Na_2SO_4$), filtered, evaporated to a solid mass. The crude product is purified by MPLC on silica gel (80% EtOAc/Hexanes, 2% MeOH) to yield the title compound, 60 mg (64%), as an oil. MS ES+ m/e 468.2 (M+1).

The following compounds are prepared utilizing the method of Example 95:

| Example # | Product Name | Physical Data |
|---|---|---|
| 96 | 3-[4-(2-Pyridin-2-yl-5,6-dihydro-4H-pyrrolo[1,2-b]pyrazol-3-yl)-quinolin-7-yl]-benzenesulfonamide | MS ES+ m/e 468.2 (M + 1) |
| 97 | 2-[4-(2-Pyridin-2-yl-5,6-dihydro-4H-pyrrolo[1,2-b]pyrazol-3-yl)-quinolin-7-yl]-benzenesulfonamide | MS ES+ m/e 468.2 (M + 1) |

Scheme 6

Preparation of Compounds Having Substituents Attached to 7-Position Through N-Linkage Scheme 6 (Step Q) depicts the modification of the 7-position of the quinoline by attachment of a nitrogen heterocycle, either aromatic or alkyl, to form a carbon-nitrogen bond to provide compounds of Formula 22. This transformation requires a base, preferably potassium tert-butoxide, a high boiling polar solvent such as dimethylsulfoxide, and a metal catalyst, preferably copper (O). The reaction is conducted at high temperatures, up to 200° C., and following workup, the products are purified by reverse phase HPLC. Copper-catalyzed nucleophilic substitutions of aryl halides have been reviewed by Lindley (See: Lindley, J. *Tetrahedron* 1984, 40, 1433-1456). Step Q can also be accomplished by palladium catalysis, preferably tris(dibenzylideneacetone) dipalladium (0) ($Pd_2(dba)_3$), with heterocyclicamines such as piperidine, piperazine, morpholine, or thiomorpholine. An alkoxide base, for example, sodium tert-butoxide, as well as 18-crown-6 and 2-(di-t-butylphosphino)biphenyl (BINAP) are also preferred for the transformation. The preferred solvent is tetrahydrofuran. The palladium-catalyzed method has been described by Wolfe and Buchwald (Wolfe, J. P.; Buchwald, S. L. *J. Org. Chem.* 1997, 62, 6066-6068).

Scheme 6

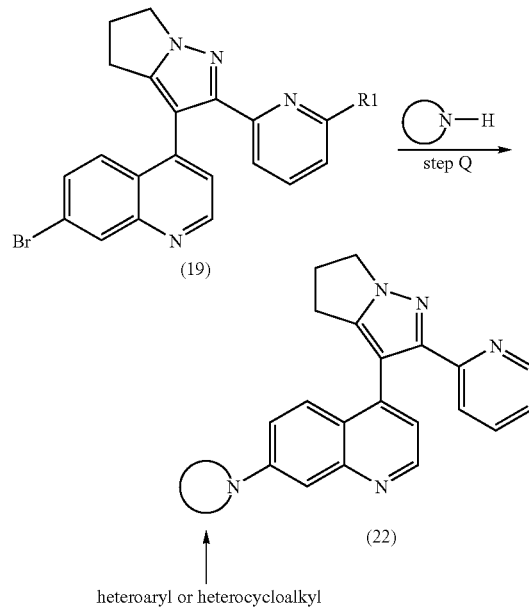

EXAMPLE 98

7-Imidazol-1-yl-4-(2-pyridin-2-yl-5,6-dihydro-4H-pyrrolo[1,2-b]pyrazol-3-yl)quinoline Ditrifluoroacetic Acid

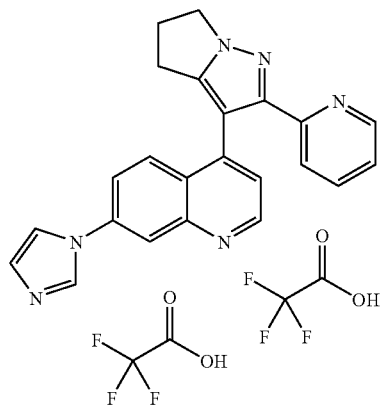

Into a dry 25 mL glass pressure tube fitted with teflon screw cap is placed the product of Preparation 9 (0.0782 g, 0.2 mmol), potassium tert-butoxide (0.045 g, 0.4 mmol), DMSO (0.25 mL), and copper powder (8 mg). The mixture is heated and stirred in an oil bath 200° C. for 3 h. The reaction mixture is allowed to cool, and then quenched with 4 mL water, followed by 4 mL EtOAc. The mixture is agitated, and the organic layer is removed and eluted over a 1 g silica gel cartridge with MeOH containing a drop of conc $NH_4OH$. The solvent is removed under vacuum. Purified product 36.3 mg (37%) is obtained by freeze drying appropriate fractions (based on MS analysis) from reverse phase HPLC using Waters Symmetry C18 column with a gradient of 10 to 70% B in A, where A is water containing 0.1% TFA and B is $CH_3CN$ containing 0.1% TFA.

MS ES+ m/e 379 (M+1)

Using the method of Example 98, the following compounds are prepared:

| Example # | Product Name | Physical Data |
|---|---|---|
| 99 | 4-(2-Pyridin-2-yl-5,6-dihydro-4H-pyrrolo[1,2-b]pyrazol-3-yl)-7-[1,2,4]triazol-1-yl-quinoline ditrifluoroacetic Acid | MS ES+ 380 (M + 1) |
| 100 | 7-Pyrazol-1-yl-4-(2-pyridin-2-yl-5,6-dihydro-4H-pyrrolo[1,2-b]pyrazol-3-yl)quinoline Trifluoroacetic Acid | MS ES+ 379 (M + 1) |
| 101 | 4-(2-pyridin-2-yl-5,6-dihydro-4H-pyrrolo[1,2-b]pyrazol-3-yl-)-7-[1,2,3]triazol-1-yl-quinoline ditrifluoroacetic Acid | MS ES+ 380 (M + 1) |

EXAMPLE 102

4-[4-(2-Pyridin-2-yl-5,6-dihydro-4H-pyrrolo[1,2-b]pyrazol-3-yl)-quinolin-7-yl]-piperazine-1-carboxylic Acid tert-Butyl Ester

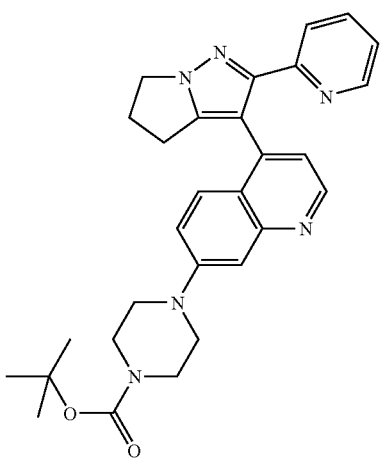

The product of Preparation 9 (0.1 g, 0.25 mmol), piperazine-1-carboxylic acid tert-butyl ester (0.07 g, 0.375 mmol), sodium tert-butoxide (0.072 g, 0.75 mmol) and 18-crown-6 (0.08 g, 0.3 mmol) are dissolved in 10 mL of dry THF. The mixture is degassed and flushed with nitrogen several times. Tris(dibenzylideneacetone) dipalladium (0) (0.014 g, 0.015 mmol) and 2-(di-t-butylphosphino)biphenyl (0.009 g, 0.03 mmol) are added, followed by degassing and flushing with nitrogen. The mixture is stirred at RT for 8 h under nitrogen. The crude mixture is diluted with EtOAc (20 mL) and extracted with saturated NaHCO$_3$. The organic phase is separated and washed with saturated brine, dried (Na$_2$SO$_4$), filtered, and evaporated to a solid mass. The crude product is purified by MPLC on silica gel (80% EtOAc/Hexanes, 1% MeOH) to yield the title compound, 0.079 g (64%), as a yellow solid. MS ES+ m/e 497.3 (M+1).

Using the method of Example 102, the following compounds are prepared:

| Example # | Product Name | Physical Data |
|---|---|---|
| 103 | 7-Piperidin-1-yl-4-(2-pyridin-2-yl-5,6-dihydro-4H-pyrrolo[1,2-b]pyrazol-3-yl)-quinoline | MS ES+ m/e 396.3 (M + 1) |
| 104 | 7-(1,1-Dioxo-1λ$^6$-thiomorph-olin-4-yl)-4-(2-pyridin-2-yl-5,6-dihydro-4H-pyrrolo[1,2-b]pyrazol-3-yl)-quinoline | MS ES+ m/e 446.2 (M + 1) |

Scheme 7

Preparation of Derivatives of Cross Coupling Products

Compounds of the type Formula 23 represent aryl, heteroaryl, or heterocycloalkyl derivatives that possess a group "X" which can be further manipulated to a group "Y" (Formula 24), as indicated by step R. The variety of such "X" groups may include, but are not limited to, carboxylic acids and alcohols. Carboxylic acids may be converted to carboxylic esters by any of a number of methods, including mineral acid catalysis (H$_2$SO$_4$ or HCl) in an alcohol solvent at temperatures from ambient to reflux. This reaction is well-known and appreciated in the art (see: Furniss, B. S.; Hannaford, A. J.; Smith, P. W. G.; Tatchell, A. R. *Vogel's Textbook of Practical Organic Chemistry* (5$^{th}$ ed.); Longman, Essex, 1989; p 1077-1079). Primary amides may be prepared from the carboxylic acids as well, via an intermediate acid chloride that is obtained by treatment with either oxalyl chloride or thionyl chloride. The intermediate acid chloride is reacted with a source of ammonia, such as gaseous NH$_3$ or ammonium hydroxide, to yield the amide. The conversion of amines to amides by acylation is well known and appreciated in the art (Larock, R. C., *Comprehensive Organic Transformations*; VCH: New York, 1984; p 979). In addition, substituted secondary and tertiary amides are obtained from the carboxylic acids by reaction with a coupling reagent such as HBTU in the presence of an amine base such as diisopropylethylamine, in a suitable solvent, preferably dimethylformamide, or dichloromethane, or tetrahydrofuran. The coupling reaction of carboxylic acids with amines in such a manner has been more generally described by Bodanszky (Bodanszky, M.; Bodanszky, A. *The Practice of Peptide Synthesis*; Springer Verlag: New York, 1984).

The alkylation of a phenolic "X" takes advantage of the reactivity of the functional group as a nucleophile through treatment with an electrophile possessing a good leaving group (for example, triflate, iodide, bromide, or chloride). A base such as potassium carbonate, sodium hydride, or an anhydrous alkoxide can be used to deprotonate the phenol and increase its nucleophilicity, in a suitable polar aprotic solvent, for example tetrahydrofuran, dimethylformamide, dioxane. These reactions are performed at temperatures ranging from ambient to reflux.

All products can be isolated and purified by silica gel chromatography (MPLC), reverse phase HPLC, or trituration of solid as described above.

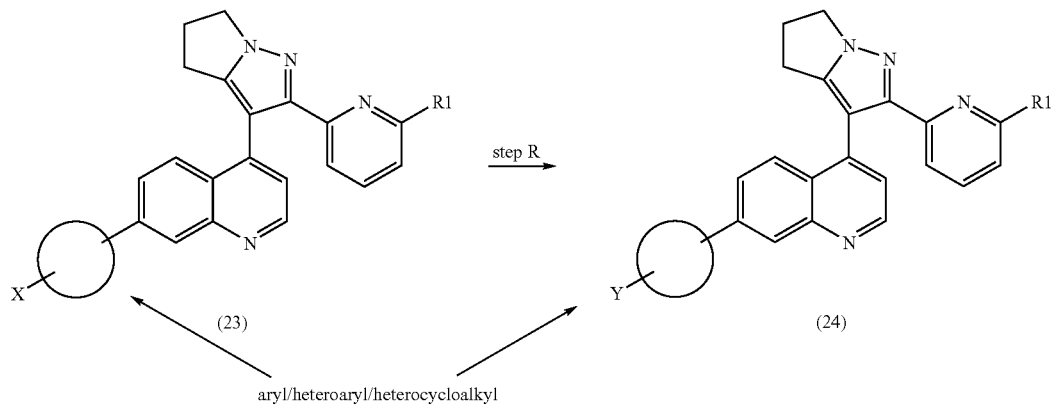

Scheme 7 aryl/heteroaryl/heterocycloalkyl

EXAMPLE 106

3-{4-[4-(2-pyridin-2-yl-5,6-dihydro-4H-pyrrolo[1,2-b]pyrazol-3-yl-)quinolin-7-yl]phenyl}propionic Acid Methyl Ester

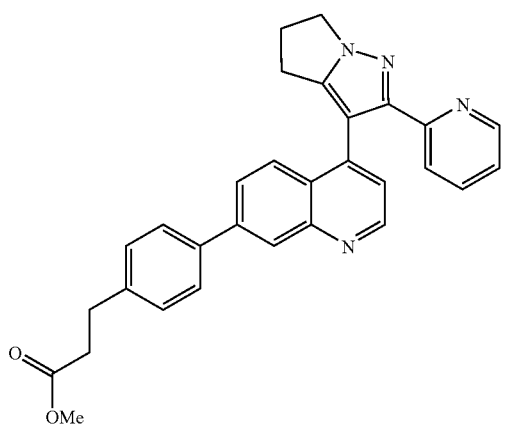

Into a 100 mL roundbottom flask is placed 3-{4-[4-(2-pyridin-2-yl-5,6-dihydro-4H-pyrrolo[1,2-b]pyrazol-3-yl)quinolin-7-yl]phenyl}propionic Acid (Example 30 before reverse phase purification) (160 mg, 0.35 mmol), 20 mL of MeOH, and 1.5 mL of conc HCl solution. The mixture is refluxed 3 h, and solvent removed under reduced pressure. The product is partitioned between CH₂Cl₂ (20 mL) and saturated K₂CO₃ solution. The organic layer is collected and dried (MgSO₄) and concentrated under vacuum. The title compound, 88.4 mg (54%), is crystallized from a concentrated CH₂Cl₂-Hexanes mixture.

MS ES⁺ 475 (M+1)

EXAMPLE 107

3-{4-[4-(2-Pyridin-2-yl-5,6-dihydro-4H-pyrrolo[1,2-b]pyrazol-3-yl)quinolin-7-yl]phenyl}propionamide

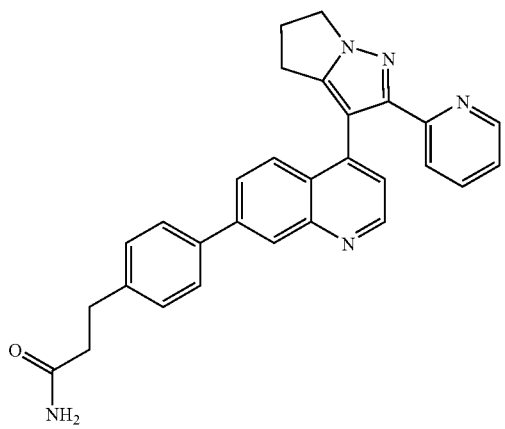

Into a 100 mL roundbottom is placed 3-{4-[4-(2-Pyridin-2-yl-5,6-dihydro-4H-pyrrolo[1,2-b]pyrazol-3-yl)quinolin-7-yl]phenyl}propionic Acid (Example 30 before reverse phase purification) (170 mg, 0.37 mmol), MeOH (20 mL), and LiOH—H₂O (9.7 mg, 0.41 mmol). The mixture is stirred 5 min, and the solvent is removed under vacuum. The product is suspended in CH₃CN (20 mL) and CH₂Cl₂ (20 mL), 5 drops DMF are added, and oxalyl chloride (0.10 mL, 1.18 mmol) is added. The mixture is stirred 1 h, solvent is removed under vacuum, and the residue redissolved in 15 mL of THF. To the solution is added concentrated NH₄OH (30 mL), and the mixture is stirred 16 h. Most of the THF is removed under vacuum, producing a precipitate, which is collected, washed with water, and dried at 60° C. under vacuum to give the title compound, 74 mg (44%).

MS ES⁺ 460 (M+1)

EXAMPLE 108

Dimethyl-(2-{4-[4-(2-Pyridin-2-yl-5,6-dihydro-4H-pyrrolo[1,2-b]pyrazol-3-yl)quinolin-7-yl]phenoxy}ethyl)amine Ditrifluoroacetic Acid

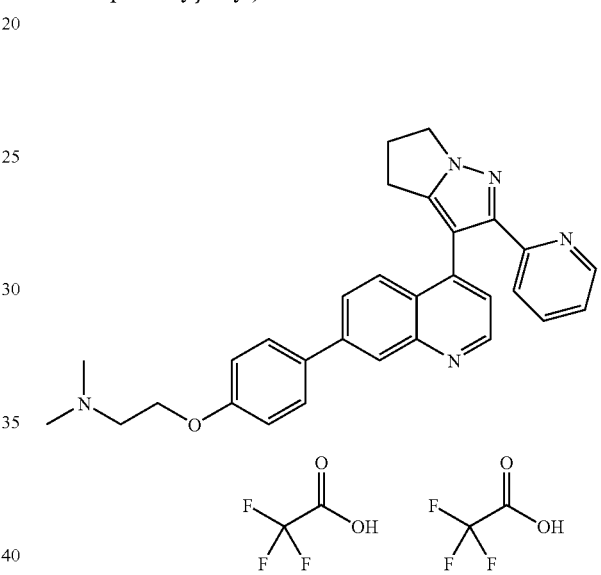

Into a glass pressure tube fitted with Teflon screw cap and magnetic bar is placed 4-[4-(2-Pyridin-2-yl-5,6-dihydro-4H-pyrrolo[1,2-b]pyrazol-3-yl)quinolin-7-yl]phenol (Example 7, before reverse phase HPLC), (0.121 g, 0.3 mmol), K₂CO₃ (0.124 g, 0.9 mmol), 2-dimethyaminoethyl chloride hydrochloride (0.048 g, 0.33 mmol), DMF (2 mL), acetone (2 mL), dioxane (2 mL), and Et₃N (2 mL). The cap is positioned, and mixture heated in oil bath at 60° C. for 16 h. Most of the solvent is removed under vacuum, and the residue is triturated with 15 mL of saturated K₂CO₃ solution, giving 127 mg of the crude titled compound as a free base. The purified product 169 mg, (80%) is obtained by freeze drying appropriate fractions (based on MS analysis) from reverse phase HPLC using Waters Symmetry C18 column with a gradient of 10 to 70% B in A, where A is water containing 0.1% TFA and B is CH₃CN containing 0.1% TFA.

MS ES+ m/e 476 (M+1)

Using the method of Example 108, considering that in some preparations no reverse phase purification is necessary and in some instances the halogen reagent required no Et₃N for forming the free base, the following compounds are synthesized:

| Example # | Product Name | Physical Data |
|---|---|---|
| 109 | 7-[4-(2-Morpholin-4-yl-ethoxy)phenyl]-4-(2-Pyridin-2-yl-5,6-dihydro-4H-pyrrolo[1,2-b]pyrazol-3-yl)quinoline Ditrifluoroacetic Acid | MS ES+ 518 (M + 1) |
| 110 | 7-[4-(2-Piperidin-1-yl-ethoxy)phenyl]-4-(2-Pyridin-2-yl-5,6-dihydro-4H-pyrrolo[1,2-b]pyrazol-3-yl)quinoline Ditrifluoroacetic Acid | MS ES+ 516 (M + 1) |
| 111 | 4-(2-Pyridin-2-yl-5,6-dihydro-4H-pyrrolo[1,2-b]pyrazol-3-yl)-7-[4-(2-pyrrolidin-1-yl-ethoxy)phenyl] quinoline Ditrifluoroacetic Acid | MS ES+ 502 (M + 1) |
| 112 | 7-[4-(3-Piperdin-1-yl-propoxy)phenyl]-4-(2-Pyridin-2-yl-5,6-dihydro-4H-pyrrolo[1,2-b]pyrazol-3-yl)quinoline Ditrifluoroacetic Acid | MS ES+ 530 (M + 1) |
| 113 | Dimethyl-(3-{4-[4-(2-Pyridin-2-yl-5,6-dihydro-4H-pyrrolo[1,2-b]pyrazol-3-yl)quinolin-7-yl]phenoxy}propyl)amine Ditrifluoroacetic Acid | MS ES+ 490 (M + 1) |
| 114 | 7-[4-(3-Morpholin-4-yl-propoxy)phenyl]-4-(2-Pyridin-2-yl-5,6-dihydro-4H-pyrrolo[1,2-b]pyrazol-3-yl)quinoline Ditrifluoroacetic Acid | MS ES+ 532 (M + 1) |
| 115 | 4-(2-Pyridin-2-yl-5,6-dihydro-4H-pyrrolo[1,2-b]pyrazol-3-yl)-7-[4-(3-pyrrolidin-1-yl-propoxy)phenyl] quinoline Ditrifluoroacetic Acid | MS ES+ 516 (M + 1) |
| 117 | 2-{4-[4-(2-Pyridin-2-yl-5,6-dihydro-4H-pyrrolo[1,2-b]pyrazol-3-yl)quinolin-7-yl]phenoxy}acetamide Trifluoroacetic Acid | MS ES+ 462 (M + 1) |
| 118 | 7-[4-(2-Methoxyethoxy)phenyl-4-(2-Pyridin-2-yl-5,6-dihydro-4H-pyrrolo[1,2-b]pyrazol-3-yl)quinoline Trifluoroacetic Acid | MS ES+ 463 (M + 1) |
| 119 | 7-[4-(2-Fluoroethoxy)phenyl]-4-(2-pyridin-2-yl-5,6-dihydro-4H-pyrrolo[1,2-b]pyrazol-3-yl)quinoline Trifluoroacetic Acid | MS ES+ 451 (M + 1) |

EXAMPLE 120

4-(2-Pyridin-2-yl-5,6-dihydro-4H-pyrrolo[1,2-b]pyrazol-3-yl)-7-[4-(2,2,2-trifluoroethoxy)phenyl) quinoline Trifluoroacetic Acid

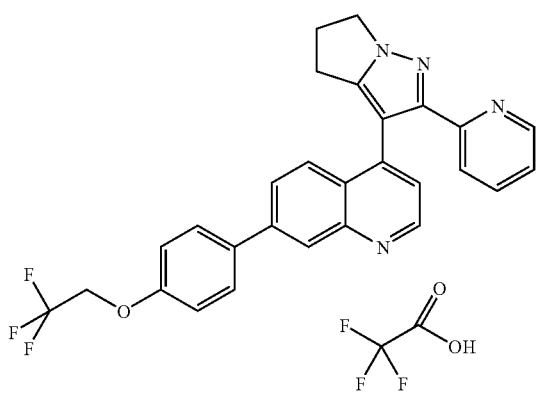

Into a 25 mL glass pressure tube fitted with Teflon screw cap and magnetic bar is placed 4-[4-(2-pyridin-2-yl-5,6-dihydro-4H-pyrrolo[1,2-b]pyrazol-3-yl)quinolin-7-yl]phenol (Example 7 before reverse phase HPLC purification); 0.100 g, 0.25 mmol), DMF (2 mL), trifluoro-methanesulfonic acid 2,2,2-trifluoroethyl ester (0.064 g 0.275 mmol), and 60% NaH (11 mg, 0.275 mmol). The cap is positioned, and mixture heated in oil bath at 70° C. for 16 h. The reaction is quenched with 15 mL water, giving 67 mg of precipitate as the title compound as a free base. The purified product, 36.4 mg (24%), is obtained by freeze drying appropriate fractions (based on MS analysis) from reverse phase HPLC using Waters Symmetry C18 column with a gradient of 10 to 70% B in A, where A is water containing 0.1% TFA and B is $CH_3CN$ containing 0.1% TFA.

MS ES+ 487 (M+1)

EXAMPLE 121

(2-{4-[4-(2-Pyridin-2-yl-5,6-dihydro-4H-pyrrolo[1,2-b]pyrazol-3-yl)-quinolin-7-yl]-benzoylamino}-ethyl)-carbamic Acid tert-Butyl Ester

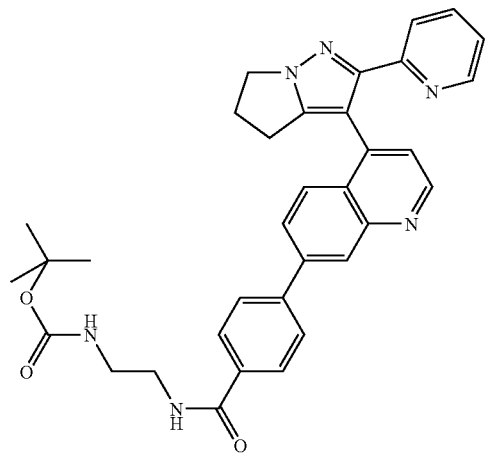

4-[4-(2-Pyridin-2-yl-5,6-dihydro-4H-pyrrolo[1,2-b]pyrazol-3-yl)-quinolin-7-yl]-benzoic acid (Example 41 before reverse phase chromatography, 0.08 g, 0.185 mmol), (2-aminoethyl)-carbamic acid tert-butyl ester (0.036 g, 0.2 mmol), N—N-Diisopropylethylamine (0.08 mL, 0.46 mmol) and HBTU (0.076 g, 0.2 mmol) are mixed in 10 mL of DMF and stirred at RT for 8 h under nitrogen. The crude mixture is diluted with EtOAc (30 mL) and extracted with saturated $NaHCO_3$. The organic phase is separated and washed with saturated brine, dried ($Na_2SO_4$), filtered, evaporated to a solid mass. The crude product is purified by MPLC on silica gel (80% EtOAc/Hexanes, 1% MeOH) to yield the title compound, 0.059 g (56%), as white solid.

MS ES+ m/e 575.3 (M+1).

Using the method of Example 121, the following compounds are synthesized:

| Example # | Product Name | Physical Data |
|---|---|---|
| 122 | Piperidin-1-yl-{4-[4-(2-pyridin-2-yl-5,6-dihydro-4H-pyrrolo[1,2-b]pyrazol-3-yl)-quinolin-7-yl]-phenyl}-methanone | MS ES+ m/e 500.3 (M + 1) |
| 123 | {4-[4-(2-Pyridin-2-yl-5,6-dihydro-4H-pyrrolo[1,2-b]pyrazol-3-yl)-quinolin-7-yl]-phenyl}-thiomorpholin-4-yl-methanone | MS ES+ m/e 518.2 (M + 1) |
| 124 | Morpholin-4-yl-{4-[4-(2-pyridin-2-yl-5,6-dihydro-4H-pyrrolo[1,2-b]pyrazol-3-yl)-quinolin-7-yl]-phenyl}-methanone | MS ES+ m/e 502.3 (M + 1) |

-continued

| Example # | Product Name | Physical Data |
|---|---|---|
| 125 | N-Carbamoylmethyl-4-[4-(2-pyridin-2-yl-5,6-dihydro-4H-pyrrolo[1,2-b]pyrazol-3-yl)-quinolin-7-yl]-benzamide | MS ES+ m/e 489.2 (M + 1) |
| 126 | N-(2-Isopropylamino-ethyl)-4-[4-(2-pyridin-2-yl-5,6-dihydro-4H-pyrrolo[1,2-b]pyrazol-3-yl)-quinolin-7-yl]-benzamide | MS ES+ m/e 517.3 (M + 1) |
| 127 | (rac) N-(2-tert-Butylsulfanyl-ethyl)-4-[4-(2-pyridin-2-yl-5,6-dihydro-4H-pyrrolo[1,2-b]pyrazol-3-yl)-quinolin-7-yl]-benzamide | MS ES+ m/e 548.3 (M + 1) |
| 128 | 3-{4-[4-(2-Pyridin-2-yl-5,6-dihydro-4H-pyrrolo[1,2-b]pyrazol-3-yl)-quinolin-7-yl]-benzoylamino}-propionic Acid Ethyl Ester | MS ES+ m/e 532.3 (M + 1) |
| 129 | (rac)-N-(1,1-Dioxo-tetrahydro-1$\lambda^6$-thiophen-3-yl)-4-[4-(2-pyridin-2-yl-5,6-dihydro-4H-pyrrolo[1,2-b]pyrazol-3-yl)-quinolin-7-yl]-benzamide | MS ES+ m/e 550.2 (M + 1) |
| 130 | 3-{4-[4-(2-Pyridin-2-yl-5,6-dihydro-4H-pyrrolo[1,2-b]pyrazol-3-yl)-quinolin-7-yl]-benzoylamino}-piperidine-1-carboxylic Acid tert-Butyl Ester | MS ES+ m/e 615.3 (M + 1) |
| 131 | 6-tert-Butoxycarbonylamino-2(S)-{4-[4-(2-pyridin-2-yl-5,6-dihydro-4H-pyrrolo[1,2-b]pyrazol-3-yl)-quinolin-7-yl]-benzoylamino}-hexanoic acid tert-butyl ester | MS ES+ m/e 717.4 (M + 1) |
| 132 | N-(2-Morpholin-4-yl-ethyl)-4-[4-(2-pyridin-2-yl-5,6-dihydro-4H-pyrrolo[1,2-b]pyrazol-3-yl)-quinolin-7-yl]-benzamide | MS ES+ m/e 545.3 (M + 1) |
| 133 | (1,1-Dioxo-1$\lambda^6$-thiomorpholin-4-yl)-{4-[4-(2-pyridin-2-yl-5,6-dihydro-4H-pyrrolo[1,2-b]pyrazol-3-yl)-quinolin-7-yl]-phenyl}-methanone | MS ES+ m/e 550.2 (M + 1) |
| 134 | 3-Methylsulfanyl-2(S)-{4-[4-(2-pyridin-2-yl-5,6-dihydro-4H-pyrrolo[1,2-b]pyrazol-3-yl)-quinolin-7-yl]-benzoylamino}-propionic Acid tert-Butyl Ester | MS ES+ m/e 606.3 (M + 1) |
| 135 | 2(S)-{4-[4-(2-Pyridin-2-yl-5,6-dihydro-4H-pyrrolo[1,2-b]pyrazol-3-yl)-quinolin-7-yl]-benzoylamino}-pentanedioic Acid Di-tert-Butyl Ester | MS ES+ m/e 674.3 (M + 1) |
| 136 | N,N-Dimethyl-4-[4-(2-pyridin-2-yl-5,6-dihydro-4H-pyrrolo[1,2-b]pyrazol-3-yl)-quinolin-7-yl]-benzamide | MS ES+ m/e 460.2 (M + 1) |
| 137 | 3-{4-[4-(2-Pyridin-2-yl-5,6-dihydro-4H-pyrrolo[1,2-b]pyrazol-3-yl)-quinolin-7-yl]-benzoylamino}-propionic Acid tert-Butyl Ester | MS ES+ m/e 560.2 (M + 1) |
| 138 | N-Methyl-4-[4-(2-pyridin-2-yl-5,6-dihydro-4H-pyrrolo[1,2-b]pyrazol-3-yl)-quinolin-7-yl]-benzamide | MS ES+ m/e 446.1 (M + 1) |
| 139 | N-(2-Methanesulfonyl-ethyl)-4-[4-(2-pyridin-2-yl-5,6-dihydro-4H-pyrrolo[1,2-b]pyrazol-3-yl)-quinolin-7-yl]-benzamide | MS ES+ m/e 538.4 (M + 1) |

EXAMPLE 140

N-Dimethylaminomethylene-4-[4-(2-pyridin-2-yl-5,6-dihydro-4H-pyrrolo[1,2-b]pyrazol-3-yl)-quinolin-7-yl]-benzamide

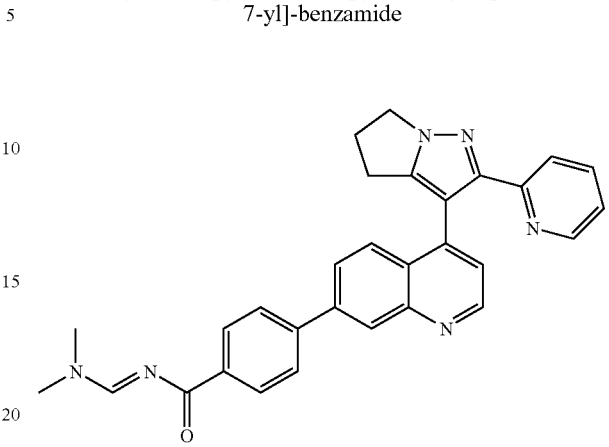

To a solution of 4-[4-(2-Pyridin-2-yl-5,6-dihydro-4H-pyrrolo[1,2-b]pyrazol-3-yl)-quinolin-7-yl]-benzoic acid (Example 41 before reverse phase chromatography, 0.05 g, 0.12 mmol) in 5 mL of $CH_2Cl_2$, 0.5 mL of DMF is added and the mixture is cooled to 0° C. Oxalyl chloride (0.11 mL, 1.2 mmol) is added dropwise to the mixture while maintaining the temperature at 0° C. The reaction is stirred at RT for 8 h under nitrogen and evaporated to an oil. The crude is dissolved in 10 mL of $CH_2Cl_2$ and saturated with dry $NH_3$ gas. The mixture is then stirred at RT for 2 h under nitrogen and evaporated to a solid mass. The crude product is purified by MPLC on silica gel (80% EtOAc/Hexanes, 1% MeOH) to yield the title compound, 0.02 g (39%), as white solid. MS ES+ m/e 487.2 (M+1).

EXAMPLE 141

4-[4-(2-Pyridin-2-yl-5,6-dihydro-4H-pyrrolo[1,2-b]pyrazol-3-yl)-quinolin-7-yl]-benzamide

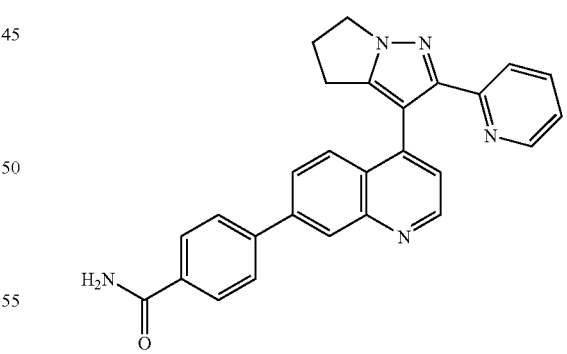

To a solution of 4-[4-(2-pyridin-2-yl-5,6-dihydro-4H-pyrrolo[1,2-b]pyrazol-3-yl)-quinolin-7-yl]-benzoic acid (Example 41 before reverse phase chromatography, 0.05 g, 0.12 mmol) in 5 mL of $CH_2Cl_2$, thionyl chloride (0.11 mL, 1.2 mmol) is added dropwise while maintaining the temperature at 0° C. The reaction is stirred at RT for 8 h under nitrogen and evaporated to an oil. The crude product is dissolved in 10 mL of $CH_2Cl_2$ and saturated with dry $NH_3$ gas. The reaction is then stirred at ambient temperature for 2 h under nitrogen and evaporated to a solid mass. The crude product is crystallized from MeOH/Et$_2$O to yield the title compound, 0.045 g (87%), as white solid. MS ES+ m/e 432.1 (M+1).

EXAMPLE 142

N-(2-Aminoethyl)-4-[4-(2-pyridin-2-yl-5,6-dihydro-4H-pyrrolo[1,2-b]pyrazol-3-yl)-quinolin-7-yl]-benzamide, Ditrifluoroacetic Acid Salt

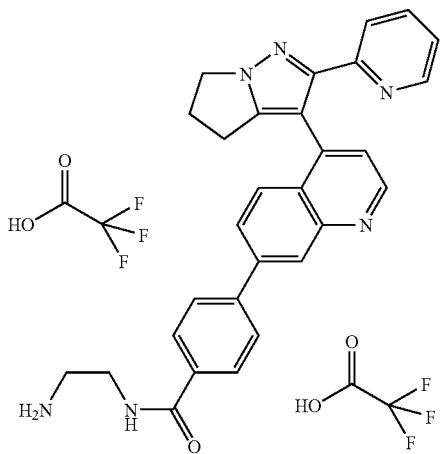

To a solution of (2-{4-[4-(2-Pyridin-2-yl-5,6-dihydro-4H-pyrrolo[1,2-b]pyrazol-3-yl)-quinolin-7-yl]-benzoylamino}-ethyl)-carbamic acid tert-butyl ester (Example 121, 0.03 g, 0.05 mmol) in 2 mL of CH$_2$Cl$_2$ is added 2 mL of trifluoroacetic acid. The reaction mixture is stirred at RT for 30 min, evaporated to an oil and titurated with Et$_2$O to yield the title compound, 0.02 g (70%), as white solid. MS ES+ m/e 475.3 (M+1).

Using the method of Example 142, the following compounds are prepared:

| Example # | Product Name | Physical Data |
|---|---|---|
| 143 | 6-Amino-2(S)-{4-[4-(2-pyridin-2-yl-5,6-dihydro-4H-pyrrolo[1,2-b]pyrazol-3-yl)-quinolin-7-yl]-benzoylamino}-hexanoic acid, Ditrifluoroacetic Acid Salt | MS ES+ m/e 561.3 (M + 1) |
| 145 | 3-Methylsulfanyl-2(S)-{4-[4-(2-pyridin-2-yl-5,6-dihydro-4H-pyrrolo[1,2-b]pyrazol-3-yl)-quinolin-7-yl]-benzoylamino}-propionic Acid Trifluoroacetic Acid Salt | MS ES+ m/e 550.3 (M + 1) |
| 146 | 2(S)-{4-[4-(2-Pyridin-2-yl-5,6-dihydro-4H-pyrrolo[1,2-b]pyrazol-3-yl)-quinolin-7-yl]-benzoylamino}-pentanedioic Acid Trifluoroacetic Acid Salt | MS ES+ m/e 562.1 (M + 1) |
| 147 | 3-{4-[4-(2-Pyridin-2-yl-5,6-dihydro-4H-pyrrolo[1,2-b]pyrazol-3-yl)-quinolin-7-yl]-benzoylamino}-propionic Acid Trifluoroacetic Acid Salt | MS ES+ m/e 504.2 (M + 1) |

REFERENCES

1. Smith, D. L.; McCloskey J. A.; *J. Org. Chem.* 43, 2087-2088, 1978
2. Price, C. C.; and Roberts, R. M., J. Am. Chem. Soc. 68, 1204 (1946); Surrey, A. R.; Hammer, H. F., J. Am. Chem. Soc., 68,113 (1946)

Determination of Biological Activity

To demonstrate that compounds of the present invention have affinity for MLK-7 and the capacity to modulate kinase activity, in vitro and whole cell kinase assays are performed. All ligands, radioligands, solvents, and reagents employed in the binding assays are readily available from commercial sources, or can be readily synthesized by the ordinarily skilled artisan.

In Vitro Assay of Purified Mixed Lineage Kinase 7 (MLK-7) Activity:

Briefly, recombinant glutathione-s-transferase (GST) tagged MLK-7 is expressed in Sf9 cells using a recombinant baculovirus created using baculovirus transfer vector pVL1392 modified to contain a GST and histidine tag. The recombinant protein is purified over a glutathione column and subsequently used for in vitro kinase assays with myelin basic protein (MBP) as the substrate for phosphorylation. The in vitro kinase reaction is run with recombinant MLK-7 at 1 nm and various concentrations of test compound in a reaction mixture containing 2 mM DTT, 30 uM ATP, 5 mM MgCl2, 5 uM MBP, 4% DMSO, 5 uCi 33P in 44 mM HEPES, (pH 7.4). The reaction is carried out for 2 hours at room temperature and then stopped by the addition of phosphoric acid to 5.5%. The phosphorylated MBP is collected on a filter and radioactivity associated with the membrane measured using a scintillation counter. Inhibitors are identified by the ability to reduce the transfer of radioactive phosphate from ATP to MBP compared to controls run without test compound.

IC$_{50}$ values, defined as the concentration of test compound required to decrease the transfer of radioactive phosphate from ATP to MBP by 50%, are then determined. Ki values (which refers to the dissociation constant of an enzyme-antagonist complex and serves as an index of ligand binding) for each respective test compound can also be calculated by application of the Cheng-Prusoff equation as described in Cheng et al., Relationship Between The Inhibition Constant (Ki) and The Concentration of Inhibitor Which Causes 50% Inhibition (IC$_{50}$) of an Enzymatic Reaction, Biochem. Pharmacol., 22: 3099-31088; (1973).

Representative compounds of the present invention have an IC50 in the MLK-7 kinase assay of ≦10,000 nM Table I (see infra.) provides IC50 data from the afore mentioned MLK-7 kinase assay for a representative sample of the exemplified compounds of the present invention.

Whole Cell Assays of MLK-7 Activity:

Mammalian expression vectors containing either MLK-7 or JNK cDNA are co-transfected into Cos cells DMEM supplemented with 5% fetal calf serum and 0.1 mg·ml ampicillin. The cDNA is expressed for 24 hours at which time media is aspirated and replaced with media containing the selected concentration of test compound. After 5 hours of incubation, cells are lysed and analysed for phospho-JNK (pJNK) levels using the pJNK luminex assay according to the manufacturers instruction (BioRad). MLK-7 inhibitors are evaluated based on the ability to reduce pJNK levels in the Cos cells compared to control samples incubated in the absence of test compound.

Test compounds may also be evaluated for the ability to inhibit phospho-p38 formation in cardiac myocytes. Primary cardiac myocytes are collected by trypsin digestion of neonatal rat heart tissue. The cells incubated in Dulbecco's modified Eagles' medium DMEM/F12 (1:1 v/v) supplemented with 2 g/L bovine serum albumin, 3 mM MEM sodium pyruvic acid, 15 mM HEPES, 100 µg/mL ampicillin, 1 µg/mL transferrin, 10 ng/mL sodium selenite, and 1 µg/mL insulin are infected with recombinant adenovirus expressing MLK- 7. After 48 hours of expression, the media is collected and replaced with media containing a selected concentration of test compound and incubation is continued for 5 hours. Media is removed, cells are lysed and analysed for phospho-p38 levels using the phospho-p38 luminex assay according to the manufacturers instruction (BioRad). MLK-7 inhibitors are evaluated based on the ability to reduce phospho-p38 levels in cardiac myocytes compared to control samples incubated in the absence of test compound.

In vitro and cell based kinase assay protocols for MLK-7, similar to those described above, can be readily designed by the ordinarily skilled artisan. Bloem et al., *J. Mol. Cell. Cardiol.*; 33: 1739-1750, (2001) provides a detailed description of the amino acid sequence of MLK-7 and various in vitro and whole cell assays of MLK-7 activity as well as a description of functional assays of gene expression and protein synthesis that may be used to assess the ability of the present compounds to treat CHF. In addition, U.S. Pat. No. 6,146,832 provides a detailed description of the isolation of the cDNA encoding MLK-7 (designated therein as CSAPK 2), expression of recombinant MLK-7 (CSAPK2) protein in bacterial cells and expression of recombinant MLK-7.

TABLE I

MLK-7 Binding Assay Values

| Example No. | MLK7 IC50 |
| --- | --- |
| 145 | +++ |
| 146 | +++ |
| 147 | +++ |
| 59 | +++ |
| 60 | +++ |
| 63 | +++ |
| 61 | +++ |
| 62 | +++ |
| 64 | ++ |
| 20 | +++ |
| 21 | ++ |
| 11 | +++ |
| 12 | +++ |
| 25 | ++ |
| 27 | +++ |
| 14 | +++ |
| 16 | +++ |
| 19 | +++ |
| 18 | +++ |
| 49 | +++ |
| 23 | +++ |
| 31 | ++ |
| 9 | +++ |
| 2 | +++ |
| 4 | +++ |
| 8 | ++ |
| 7 | +++ |
| 10 | +++ |
| 34 | +++ |
| 22 | ++ |
| 26 | +++ |
| 15 | +++ |
| 35 | +++ |
| 32 | ++ |
| 24 | ++ |
| 6 | +++ |
| 5 | ++ |
| 33 | +++ |
| 29 | + |
| 30 | +++ |
| 3 | +++ |
| 28 | +++ |
| 17 | + |
| 21 | ++ |
| 36 | ++ |
| 37 | +++ |
| 38 | +++ |

TABLE I-continued

MLK-7 Binding Assay Values

| Example No. | MLK7 IC50 |
| --- | --- |
| 52 | +++ |
| 53 | + |
| 47 | ++ |
| 40 | +++ |
| 48 | +++ |
| 65 | +++ |
| 41 | +++ |
| 42 | + |
| 50 | +++ |
| 69 | +++ |
| 54 | ++ |
| 70 | +++ |
| 71 | +++ |
| 66 | +++ |
| 68 | +++ |
| 43 | +++ |
| 44 | + |
| 99 | ++ |
| 100 | +++ |
| 98 | ++ |
| 102 | + |
| 103 | ++ |
| 55 | ++ |
| 51 | +++ |
| 89 | ++ |
| 67 | ++ |
| 88 | ++ |
| 101 | ++ |
| 45 | ++ |
| 85 | ++ |
| 75 | +++ |
| 84 | +++ |
| 95 | +++ |
| 96 | +++ |
| 117 | +++ |
| 118 | +++ |
| 119 | +++ |
| 120 | +++ |
| 121 | +++ |
| 138 | +++ |
| 122 | +++ |
| 56 | +++ |
| 123 | +++ |
| 97 | ++ |
| 124 | +++ |
| 125 | +++ |
| 126 | +++ |
| 127 | ++ |
| 128 | +++ |
| 139 | +++ |
| 129 | +++ |
| 140 | +++ |
| 130 | +++ |
| 106 | +++ |
| 107 | +++ |
| 104 | + |
| 108 | +++ |
| 109 | +++ |
| 110 | +++ |
| 141 | +++ |
| 46 | +++ |
| 113 | +++ |
| 111 | +++ |
| 112 | +++ |
| 131 | ++ |
| 132 | +++ |
| 133 | +++ |
| 86 | +++ |
| 74 | +++ |
| 73 | +++ |
| 76 | +++ |
| 77 | +++ |
| 87 | +++ |
| 114 | +++ |
| 115 | +++ |

TABLE I-continued

MLK-7 Binding Assay Values

| Example No. | MLK7 IC50 |
|---|---|
| 82 | +++ |
| 78 | +++ |
| 79 | + |
| 80 | + |
| 83 | + |
| 81 | +++ |
| 134 | ++ |
| 57 | +++ |
| 143 | +++ |
| 58 | +++ |
| 94 | +++ |
| 90 | +++ |
| 91 | +++ |
| 92 | +++ |
| 136 | +++ |
| 137 | +++ |
| 135 | ++ |
| 93 | +++ |
| 72 | + |

Legend:
"+" represents a value of ≦10,000 nM
"++" represents a value of ≦1,000 nM
"+++" represents a value of ≦100 nM
"--" indicates the value was not determined

What is claimed is:

1. A compound of the formula:

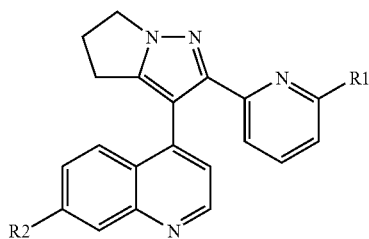

Formula I wherein,
R1 represents hydrogen, halo, or (C1-C4)alkyl; and
R2 represents:
(a) aryl;
(b) aryl optionally substituted one to three times with a substituent independently selected from the group consisting of:
(i) halo,
(ii) amino,
(iii) nitro,
(iv) hydroxy,
(v) cyano,
(vi) $(C_1-C_4)$alkyl,
(vii) $(C_1-C_4)$alkoxy,
(viii) hydroxy$(C_1-C_4)$alkyl,
(ix) amino$(C_1-C_4)$alkyl
(x) hydroxy$(C_1-C_4)$alkoxy,
(xi) halo$(C_1-C_4)$alkoxy,
(xii) $(C_1-C_4)$alkoxy$(C_1-C_4)$alkoxy,
(xiii) trifluoromethyl,
(xiv) difluoromethyl,
(xv) trifluoromethoxy,
(xvi) difluoromethoxy,
(xvii) $(C_3-C_7)$cylcoalkyl,
(xviii) $COR^3$,
(xix) $(C_1-C_4)$alkyl-COR4,
(xx) amino$(C_1-C_4)$alkyl-COR4,
(xxi) hydroxy$(C_1-C_4)$alkyl-COR4
(xxii) $(C_1-C_4)$alkoxy-COR5,
(xxiii) —C(NH$_2$)=N—OH
(xxiv) $NHSO_2R^6$,
(xxv) $SO_2R^7$,
(xxvi) $NHCOR^8$,
(xxvii) $SOR^9$,
(xxviii) $SR^{10}$,
(xxix) $CONHR^{11}$,
(xxx) $O-(CH_2)q-NR^{12}R^{13}$, wherein q represents 1-4,
(xxxi) tetrazole,
(xxxii) methyltetrazole, and
(xxxiii) $CONCH-NR^{15}R^{16}$
(c) thiophen-2-yl, thiophen-3-yl, pyridin-4-yl, pyridin-3-yl, furan-3-yl, furan-2-yl, thiazol-2-yl, pyrazin-2-yl, pyridin-2-yl, 1H-pyrrol-2-yl, 1H-pyrrol-3-yl, pyrimidin-2-yl, pyrimidin-5-yl, imidazol-1-yl, [1,2,4]triazol-1-yl, pyrazol-1-yl, [1,2,3]triazol-1-yl, piperidin-1-yl, 1,1-Dioxo-1λ6-thiomorph-olin-4-yl, piperazin-1-yl, 4-methylthiophen-2-yl, 6-carboxypyridin-2-yl, 5-fluoropyridin-2-yl, 6-methoxypyridazin-3-yl, 2-aminopyrimidin-5-yl, 5-aminosulfonyl thiophen-2-yl, or 4-tert-butoxycarbonyl piperazin-1-yl;
(d) benzofused heterocycle;
(e) benzofused heterocycle optionally substituted one or two times with a substituent independently selected from the group consisting of:
(i) halo,
(ii) amino,
(iii) $(C_1-C_4)$alkyl,
(iv) $(C_1-C_4)$alkoxy, and
(v) $(C_1-C_4)$alkylcarbonyl, or
(f) $(C_3-C_7)$cylcoalkyl;
$R^3$ represents independently at each occurrence amino, hydroxy, $(C_1-C_4)$alkyl, $(C_1-C_4)$alkoxy, NH—$(C_1-C_4)$alkylamine, N,N—$(C_1-C_4)$dialkylamine, or a heterocycle selected from the group consisting of:

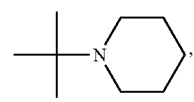

(a)

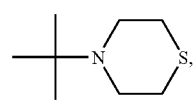

(b)

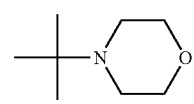

(c)

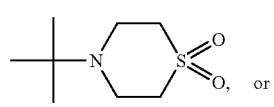

(d)

or

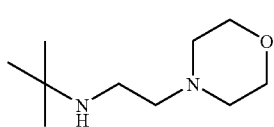

(e)

$R^4$ and $R^5$ represent independently at each occurrence amino, hydroxy, $(C_1-C_4)$alkyl, or $(C_1-C_4)$alkoxy;

$R^6$ and $R^7$ represent independently at each occurrence amino or (C1-C4)alkyl;

$R^8$ represents independently at each occurrence amino, $(C_1-C_4)$alkyl, or $(C_1-C_4)$alkoxy;

$R^9$ and $R^{10}$ represent independently at each occurrence (C1-C4)alkyl;

$R^{11}$ represents independently at each occurrence (C1-C4) alkyl or a substituent selected from the group consisting of:

(a) —$(CH_2)_n$—X—Y
(b) —$CH(COR^{14})$—$(CH_2)_m$—X'—Y'

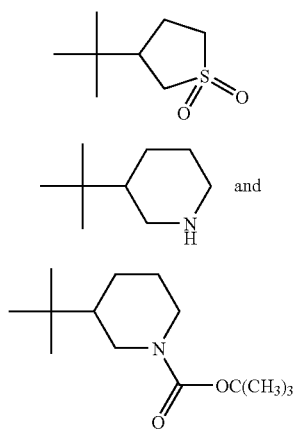

wherein,
n and m each independently represent 0-4;
X and X' represent independently at each occurrence —CO—, —$CH_2$—, —NH—, —S—, or —$SO_2$—; and
Y and Y' represent independently at each occurrence amino, hydroxy, $(C_1-C_4)$alkyl, $(C_1-C_4)$alkoxy, $(C_1-C_4)$alkoxycarbonyl, NH—$(C_1-C_4)$alkylamine, or N,N—$(C_1-C_4)$dialkylamine,
provided that where X or X' represents S, then Y or Y' is not amino or hydroxy;
$R^{12}$ and $R^{13}$ represent independently at each occurrence hydrogen or $(C_1-C_4)$alkyl, or $R^{12}$ and $R^{13}$ together with the nitrogen atom to which they are attached form a piperidino, pyrrolidino, morpholino or a methylpiperazino group;
$R^{14}$ represents independently at each occurrence hydroxy, amino, or $(C_1-C_4)$alkoxy; and
$R^{15}$ and $R^{16}$ each represent independently at each occurrence hydrogen or $(C_1-C_4)$alkyl,
or a pharmaceutically acceptable salt thereof.

2. The compound according to claim 1 wherein R1 represents hydrogen or $(C_1-C_4)$alkyl.

3. The compound according to claim 2 wherein R1 represents hydrogen or methyl.

4. The compound according to claim 1 wherein R2 represents
(a) phenyl;
(b) phenyl optionally substituted one to three times with a substituent independently selected from the group consisting of:
(i) halo,
(ii) amino,
(iii) nitro,
(iv) hydroxy,
(v) cyano,
(vi) $(C_1-C_4)$alkyl,
(vii) $(C_1-C_4)$alkoxy,
(viii) amino$(C_1-C_4)$alkyl
(ix) hydroxy$(C_1-C_4)$alkoxy,
(x) halo$(C_1-C_4)$alkoxy,
(xi) $(C_1-C_4)$alkoxy$(C_1-C_4)$alkoxy,
(xii) trifluoromethyl,
(xiii) $(C_3-C_7)$cylcoalkyl,
(xiv) $COR^3$,
(xv) $(C_1-C_4)$alkyl-COR4,
(xvi) $(C_1-C_4)$alkoxy-COR5,
(xvii) $NHSO_2R^6$,
(xviii) $SO_2R^7$,
(xix) $NHCOR^8$,
(xx) $SOR^9$,
(xxi) $SR^{10}$,
(xxii) $CONHR^{11}$, and
(xxiii) O—$(CH_2)_q$-$NR^{12}R^{13}$, wherein q represents 1-4;
(c) thiophen-2-yl, thiophen-3-yl, pyridin-4-yl, pyridin-3-yl, furan-3-yl, furan-2-yl, thiazol-2-yl, pyrazin-2-yl, pyridin-2-yl, 1H-pyrrol-2-yl, 1H-pyrrol-3-yl, pyrimidin-2-yl, pyrimidin-5-yl, imidazol-1-yl, [1,2,4]triazol-1-yl, pyrazol-1-yl, [1,2,3]triazol-1-yl, piperidin-1-yl, 1,1-Dioxo-1λ6-thiomorph-olin-4-yl, piperazin-1-yl, 4-methylthiophen-2-yl, 6-carboxypyridin-2-yl, 5-fluoropyridin-2-yl, 6-methoxypyridazin-3-yl, 2-aminopyrimidin-5-yl, 5-aminosulfonyl thiophen-2-yl, or 4-tert-butoxycarbonyl piperazin-1-yl;
(d) benzofused heterocycle;
(e) benzofused heterocycle optionally substituted one or two times with a substituent independently selected from the group consisting of:
(vi) halo,
(vii) amino,
(viii) $(C_1-C_4)$alkyl,
(ix) $(C_1-C_4)$alkoxy, and
(x) $(C_1-C_4)$alkylcarbonyl, or
(f) $(C_3-C_7)$cycloalkyl.

5. The compound according to claim 4 wherein R2 represents
(a) phenyl;
(b) phenyl optionally substituted one to three times with a substituent independently selected from the group consisting of:
(i) fluoro, bromo, or chloro,
(ii) amino,
(iii) nitro,
(iv) hydroxy,
(v) cyano,
(vi) methyl, ethyl, propyl, butyl, i-butyl,
(vii) methoxy or ethoxy,
(viii) aminomethyl or aminoethyl,
(ix) hydroxy methoxy or hydroxy ethoxy,
(x) 2-fluoro ethoxy or 2-trifluoro ethoxy,
(xi) methoxy ethoxy,
(xii) trifluoromethyl,
(xiii) cyclohexyl,
(xiv) $COR^3$, wherein $R^3$ represents amino, hydroxy, $(C_1-C_4)$alkyl, $(C_1-C_4)$alkoxy, N,N—$(C_1-C_4)$dialkylamine,
or a heterocycle selected from the group consisting of:

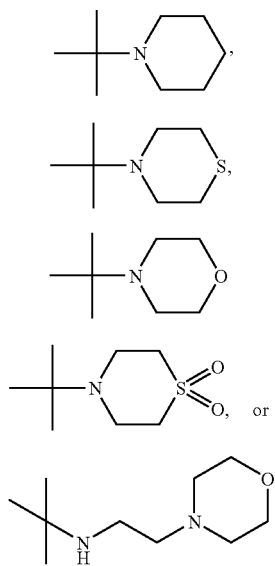

(i)

(ii)

(iii)

(iv)

(v)

(xv) (C$_1$-C$_4$)alkyl-COR4, wherein R4 represents hydroxy, amino, or (C1-C4)alkoxy,
(xvi) (C$_1$-C$_4$)alkoxy-COR5, wherein R5 represents hydroxy or amino,
(xvii) NHSO$_2$R$^6$, wherein R6 represents (C1-C4)alkyl,
(xviii) SO$_2$R$^7$, wherein R7 represents amino or (C1-C4)alkyl,
(xix) NHCOR$^8$, wherein R8 represents methyl,
(xx) SOR$^9$, wherein R9 represents methyl,
(xxi) SR$^{10}$, wherein R10 represents methyl or ethyl,
(xxii) CONHR$^{11}$, wherein R11 represents —(CH$_2$)n-X—Y, where n=0-2, X represents —S—, —CH$_2$—, —(CH$_2$)$_2$—, —NH—, —CO—, or —SO$_2$—, and Y represents amino, (C1-C4)alkyl, (C1-C4)alkoxycarbonyl, or NH—(C1-C4)alkylamine; or wherein R11 represents CH(COR14)—(CH$_2$)m-X'—Y" where R14 represents hydroxy or (C1-C4)alkoxy, m=0-4, X' represents —S—, —CH$_2$—, —NH—, or —CO—, and Y' represents amino, hydroxy, (C1-C4)alkyl, or (C1-C4)alkoxycarbonyl; or wherein R11 represents a group selected from the following:

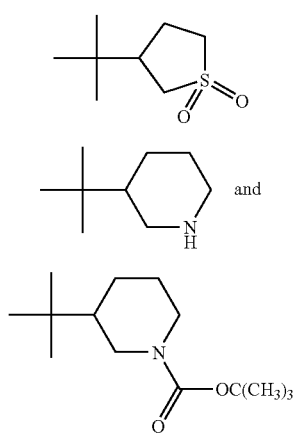

(a)

(b) and (c)

(xxiii) O—(CH$_2$)q-NR$^{12}$R$^{13}$, wherein q represents 1-3, R12 and R13 independently represent hydrogen or methyl or R12 and R13 together with the nitrogen to which they are attached form a piperidino, pyrrolidino, morpholino or a methylpiperazino group;

(c) thiophen-2-yl, thiophen-3-yl, pyridin-4-yl, pyridin-3-yl, furan-3-yl, furan-2-yl, thiazol-2-yl, pyrazin-2-yl, pyridin-2-yl, 1H-pyrrol-2-yl, 1H-pyrrol-3-yl, pyrimidin-2-yl, pyrimidin-5-yl, imidazol-1-yl, [1,2,4]triazol-1-yl, pyrazol-1-yl, [1,2,3]triazol-1-yl, piperidin-1-yl, 1,1-Dioxo-1λ6-thiomorph-olin-4-yl, piperazin-1-yl, 4-methylthiophen-2-yl, 6-carboxypyridin-2-yl, 5-fluoropyridin-2-yl, 6-methoxypyridazin-3-yl, 2-aminopyrimidin-5-yl, 5-aminosulfonyl thiophen-2-yl, or 4-tert-butoxycarbonyl piperazin-1-yl;

(d) benzofused heterocycle;

(e) benzofused heterocycle optionally substituted one or two times with a substituent independently selected from the group consisting of:
(i) amino or
(ii) methyl; or (f) (C$_3$-C$_7$)cycloalky.

6. The compound according to claim 5 wherein R2 represents phenyl or phenyl optionally substituted one to three times with a substituent independently selected from the group consisting of:

(i) fluoro, bromo, or chloro,
(ii) amino,
(iii) nitro,
(iv) hydroxy,
(v) cyano,
(vi) methyl, ethyl, propyl, butyl, i-butyl,
(vii) methoxy or ethoxy,
(viii) aminomethyl or aminoethyl,
(ix) hydroxy methoxy or hydroxy ethoxy,
(x) 2-fluoro ethoxy or 2-trifluoro ethoxy,
(xi) methoxy ethoxy,
(xii) trifluoromethyl,
(xiii) cyclohexyl,
(xiv) COR$^3$, wherein R3 represents amino, hydroxy, (C1-C4)alkyl, (C1-C4)alkoxy, N,N—(C$_1$-C$_4$)dialkylamine, or a heterocycle selected from the group consisting of:

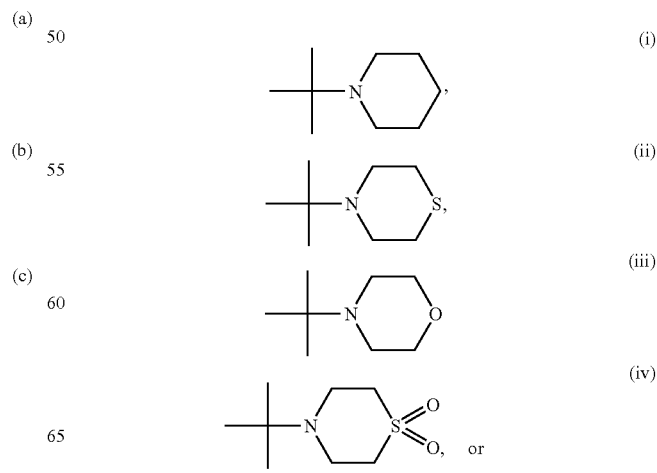

(i)

(ii)

(iii)

(iv)

-continued (v)

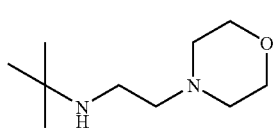

(xv) (C₁-C₄)alkyl-COR4, wherein R4 represents hydroxy, amino, or (C1-C4)alkoxy,
(xvi) (C₁-C₄)alkoxy-COR5, wherein R5 represents hydroxy or amino,
(xvii) NHSO$_2$R$^6$, wherein R6 represents (C1-C4)alkyl,
(xviii) SO$_2$R$^7$, wherein R7 represents amino or (C1-C4)alkyl,
(xix) NHCOR$^8$, wherein R8 represents methyl,
(xx) SOR$^9$, wherein R9 represents methyl,
(xxi) SR$^{10}$, wherein R10 represents methyl or ethyl,
(xxii) CONHR$^{11}$, wherein R11 represents —(CH$_2$)n-X—Y, where n=0-2, X represents —S—, —CH$_2$—, —(CH$_2$)$_2$—, —NH—, —CO—, or —SO$_2$—, and Y represents amino, (C1-C4)alkyl, (C1-C4)alkoxycarbonyl, or NH—(C1-C4)alkylamine; or wherein R11 represents CH(COR14)—(CH$_2$)m-X'—Y" where R14 represents hydroxy or (C1-C4)alkoxy, m=0-4, X' represents —S—, —CH$_2$—, —NH—, or —CO—, and Y' represents amino, hydroxy, (C1-C4)alkyl, or (C1-C4)alkoxycarbonyl; or wherein R11 represents a group selected from the following:

(a)

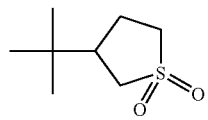

(b)

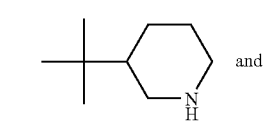

and (c)

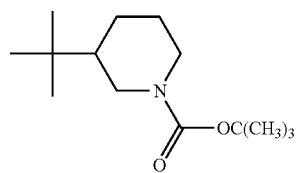

(xxiii) O—(CH$_2$)q-NR$^{12}$R$^{13}$, wherein q represents 1-3, R12 and R13 independently represent hydrogen or methyl or R12 and R13 together with the nitrogen to which they are attached form a piperidino, pyrrolidino, morpholino or a methylpiperazino group.

7. The compound according to claim 5 wherein R2 represents benzimidazole, benzofuran, benzothiophene, benzo[1,3]-dioxolyl, benzothiazole, 2,2-dioxy-2,3-dihydro-I H-2λ$^6$-benzo[c]thiophene, indole; or benzoimidazole, benzofuran, benzothiophene, benzo[1,3]-dioxolyl, benzothiazole, 2,2-dioxy-2,3-dihydro- I H-2λ$^6$-benzo[c]thiophene, or indole optionally substituted one or two times with a substituent independently selected from the group consisting of:
  (i) amino, or
  (ii) methyl.

8. A pharmaceutical composition comprising as an active ingredient a compound according to claim 1 in combination with a pharmaceutically acceptable carrier, diluent or excipient.

\* \* \* \* \*